US007700782B2

(12) United States Patent
Connolly et al.

(10) Patent No.: US 7,700,782 B2
(45) Date of Patent: Apr. 20, 2010

(54) COMPOUNDS 569

(75) Inventors: Stephen Connolly, Loughborough (GB);
Alexander Humphries, Loughborough
(GB); Premji Meghani, Loughborough
(GB)

(73) Assignee: AstraZeneca AB (SE)

( * ) Notice: Subject to any disclaimer, the term of this
patent is extended or adjusted under 35
U.S.C. 154(b) by 0 days.

(21) Appl. No.: 11/959,679

(22) Filed: Dec. 19, 2007

(65) Prior Publication Data
US 2008/0207698 A1 Aug. 28, 2008

(51) Int. Cl.
*A61K 31/428* (2006.01)
*C07D 277/68* (2006.01)
(52) U.S. Cl. ........................ 548/165; 514/369
(58) Field of Classification Search ............ 548/165
See application file for complete search history.

(56) References Cited

U.S. PATENT DOCUMENTS

| 2,653,977 A | 9/1953 | Craig et al. |
| 3,775,477 A | 11/1973 | Diana |
| 4,460,581 A | 7/1984 | Schromm et al. |
| 5,648,370 A | 7/1997 | Bonnert et al. |
| 6,686,353 B1 | 2/2004 | Shiota et al. |
| 2002/0055651 A1 | 5/2002 | Moran et al. |
| 2003/0229058 A1 | 12/2003 | Moran et al. |
| 2008/0207698 A1 | 8/2008 | Connolly et al. |
| 2008/0242649 A1 | 10/2008 | Cadogan et al. |
| 2008/0249145 A1 | 10/2008 | Whittock et al. |
| 2008/0300275 A1 | 12/2008 | Bonnert et al. |
| 2009/0029958 A1 | 1/2009 | Alcaraz et al. |
| 2009/0062259 A1 | 3/2009 | Alcaraz et al. |

FOREIGN PATENT DOCUMENTS

| EP | 0162576 | 11/1985 |
| EP | 0174811 | 3/1986 |
| EP | 0175525 | 3/1986 |
| EP | 0220878 | 5/1987 |
| EP | 0303466 | 2/1989 |
| EP | 0422889 | 4/1991 |
| JP | 2005-187357 | 7/2005 |
| SE | 7415945 | 6/1975 |
| WO | WO 92/08708 | 5/1992 |
| WO | WO 93/23385 | 11/1993 |
| WO | WO 93/24473 | 12/1993 |
| WO | WO 97/10227 | 3/1997 |
| WO | WO 97/23470 | 7/1997 |
| WO | WO 97/44329 | 11/1997 |
| WO | WO 98/38180 | 9/1998 |
| WO | WO 98/45294 | 10/1998 |
| WO | WO 99/36095 | 7/1999 |
| WO | WO 99/64035 | 12/1999 |
| WO | WO 00/75114 | 12/2000 |
| WO | WO 01/11933 | 2/2001 |
| WO | WO 01/12167 | 2/2001 |
| WO | WO 01/12191 | 2/2001 |
| WO | WO 01/12192 | 2/2001 |
| WO | WO 01/42193 | 6/2001 |
| WO | WO 02/06255 | 1/2002 |
| WO | WO 02/076933 | 10/2002 |
| WO | WO 03/024439 | 3/2003 |
| WO | WO 2004/016578 | 2/2004 |
| WO | WO 2004/016601 | 2/2004 |
| WO | WO 2004/039766 | 5/2004 |
| WO | WO 2004/071388 | 8/2004 |
| WO | WO 2004/074276 | 9/2004 |
| WO | WO 2004/089892 | 10/2004 |
| WO | WO 2005/030678 | 4/2005 |
| WO | WO 2005/040103 | 5/2005 |
| WO | WO 2005/044787 | 5/2005 |
| WO | WO 2005/070872 | 8/2005 |
| WO | WO 2005/074924 | 8/2005 |
| WO | WO 2005/092841 | 10/2005 |
| WO | WO 2005/092861 | 10/2005 |
| WO | WO 2005/092870 | 10/2005 |
| WO | WO 2005/110990 | 11/2005 |
| WO | WO 2005/111002 | 11/2005 |
| WO | WO 2005/111004 | 11/2005 |
| WO | WO 2005/121065 | 12/2005 |
| WO | WO 2006/014704 | 2/2006 |
| WO | WO 2006/023457 | 3/2006 |
| WO | WO 2006/023460 | 3/2006 |
| WO | WO 2006/031556 | 3/2006 |
| WO | WO 2006/056471 | 6/2006 |
| WO | WO 2006/074897 | 7/2006 |

(Continued)

OTHER PUBLICATIONS

Austin et al. "QSAR and the Rational Design of Long-Acting Dual $D_2$-Receptor/$\beta_2$-Adrenoceptor Agonists" J. Med. Chem. 2003 46:3210-3220.

(Continued)

*Primary Examiner*—Laura L. Stockton
(74) *Attorney, Agent, or Firm*—Sigh & Richardson P.C.

(57) ABSTRACT

The present invention provides compounds of formula (I)

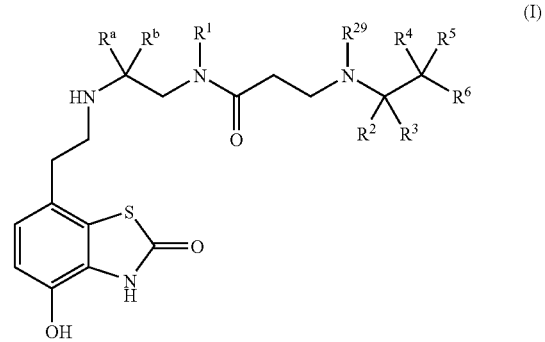

wherein $R^a$, $R^b$, $R^1$, $R^2$, $R^3$, $R^4$, $R^5$, $R^6$ and $R^{29}$ are as defined in the specification, processes for their preparation, pharmaceutical compositions containing them and their use in therapy.

3 Claims, No Drawings

FOREIGN PATENT DOCUMENTS

| | | |
|---|---|---|
| WO | WO 2006/128675 | 12/2006 |
| WO | WO 2007/010356 | 1/2007 |
| WO | WO-2007/018461 A1 * | 2/2007 |
| WO | WO 2007/027133 | 3/2007 |
| WO | WO 2007/027134 | 3/2007 |
| WO | WO 2007/102771 | 9/2007 |
| WO | WO 2007/106016 | 9/2007 |
| WO | WO 2009/037503 | 3/2008 |
| WO | WO 2008/041914 | 4/2008 |
| WO | WO 2008/075025 | 6/2008 |
| WO | WO 2008/075026 | 6/2008 |
| WO | WO 2008/096111 | 8/2008 |
| WO | WO 2008/096112 | 8/2008 |
| WO | WO 2008/096119 | 8/2008 |
| WO | WO 2008/096121 | 8/2008 |
| WO | WO 2008/104776 | 9/2008 |
| WO | WO 2008/104790 | 9/2008 |

OTHER PUBLICATIONS

Berge et al. "Pharmaceutical Salts" J Pharmaceutical Sciences. 1977 66(1) 1-19.

Bonnert et al. "Dual $D_2$-Receptor and $\beta_2$-Adrenoceptor Agonists for the Treatment of Airway Diseases. 1. Discovery and Biological Evaluation of Some 7-(2-Aminoethyl)-4-hydroxybenzothiazol-2(3H)-one Analogues" J Med Chem. 1998 (41) 4915-4917.

Davies et al. "Indacaterol. Asthma Therapy Treatment of COPD $\beta_2$-Adrenoceptor Agonist" Drugs of the Future. 2005 30(12) 1219-1224.

Dougall et al. "Dual dopamine $D_2$ receptor and $\beta_2$-adrenoceptor agonists for the treatment of chronic obstructive pulmonary disease: the pre-clinical rationale" Respir Med (Suppl A). 2003 (97) S3-S7 (Abstract).

Fernandez et al. "Alkaline Hydrolysis of 1,2,3-Trisubstituted Cyclic Amidinium Salts. Kinetic Study of N→N' Acyl Migration in Alkaline Solution in an Ethylenediamine Derivative" J.C.S. Perkin II. 1978 545-550.

Fernández et al. "N→N' Intramolecular Acyl Transfer in Acid Media for Alkylenediamine Derivatives" J.C.S. Perkin II. 1978 550-553.

Norman, "Which of three structures is AZD-3199? WO-2008104790, WO-2008096112 and WO-2008096119" Expert Opin. Ther. Patents. 2009 19(7) 1-7.

Weinstock et al. "Synthesis and Evaluation of Non-Catechol D-1 and D-2 Dopamine Receptor Agonists: Benzimidazol-2-one, Benzoxazol-2-one, and the Highly Potent Benzothiazol-2-one 7 Ethylamines" J Med Chem. 1987 (30) 1166-1176.

Wermuth et al., Handbook of Pharmaceutical salts: properties, selection and use, (2002) pp. 1-7: published by Wiley-VCH Verlag, ISBN: 10-3-906390-26-8.

Wright et al. "The Rearrangement of N-(Methylamino-alkyl)anilides" J Org Chem. 1961 26(6) 2120-2123.

* cited by examiner

COMPOUNDS 569

The present invention relates to benzothiazolone derivatives, processes for their preparation, pharmaceutical compositions containing them and their use in therapy.

Adrenoceptors are a group of G-protein coupled receptors divided into two major sub-families, α and β. These sub-families are further divided into sub-types of which the β sub-family has at least 3 members: β1, β2 and β3. β2 adrenoceptors (henceforth referred to as β2 receptors) are mainly expressed on smooth muscle cells.

Agonism of the β2 receptor on airway smooth muscle produces relaxation and therefore bronchodilatation. Through this mechanism, β2 agonists act as functional antagonists to all bronchoconstrictor substances such as the naturally-occurring histamine and acetylcholine as well as the experimental substances methacholine and carbachol. β2 agonists are widely used to treat airways diseases including asthma and chronic obstructive pulmonary disease (COPD), and this has been extensively reviewed in the literature and incorporated into national guidelines for the treatment of these diseases (British Guideline on the Management of Asthma, NICE guideline No. 12 on the Management of COPD).

β2 agonists are classed either as short-acting or long-acting. Short-acting β2 agonists (SABAs) such as salbutamol have a duration of action of 2-4 hours. They are suitable for rescue medication during a period of acute bronchoconstriction but are not suitable for continuous medication because the beneficial effect of these drugs wears off during the night. Long-acting β2 agonists (LABAs) currently have a duration of action of about 12 hours and are administered twice daily to provide continuous bronchodilatation. They are particularly effective when administered in combination with inhaled corticosteroids. This benefit is not seen when inhaled corticosteroids are combined with SABAs (Kips and Pauwels, *Am. J. Respir. Crit. Care Med.*, 2001, 164, 923-932). LABAs are recommended as add-on therapy to patients already receiving inhaled corticosteroids for asthma to reduce nocturnal awakening and reduce the incidence of exacerbations of the disease. Corticosteroids and LABAs are conveniently co-administered in a single inhaler to improve patient compliance.

There are shortcomings to existing LABAs and there is a need for a new drug in this class. Salmeterol, a commonly used LABA, has a narrow safety margin and side effects related to systemic agonism of β2 receptors (such as tremor, hypokalaemia, tachycardia and hypertension) are common. Salmeterol also has a long onset of action which precludes its use as both a rescue and a maintenance therapy. All current LABAs are administered twice daily and there is a medical need for once daily treatments to improve treatment and patient compliance. Such once daily compounds, co-administered with corticosteroids, will become the mainstay of asthma treatment (Barnes, *Nature Reviews*, 2004, 3, 831-844). The advantages of once-daily bronchodilator treatment in COPD has been demonstrated with tiotropium, a non-selective muscarinic antagonist (Koumis and Samuel, *Clin. Ther.* 2005, 27(4), 377-92). There is, however, a need for a once-daily LABA for the treatment of COPD to avoid the side effects of anti-muscarinics such as tiotropium.

Benzothiazolone derivatives having dual β2 receptor and dopamine (D2) receptor agonist properties are known from WO 92/08708, WO 93/23385, WO 97/10227 and U.S. Pat. No. 5,648,370.

In accordance with the present invention there is therefore provided a compound of formula (I):

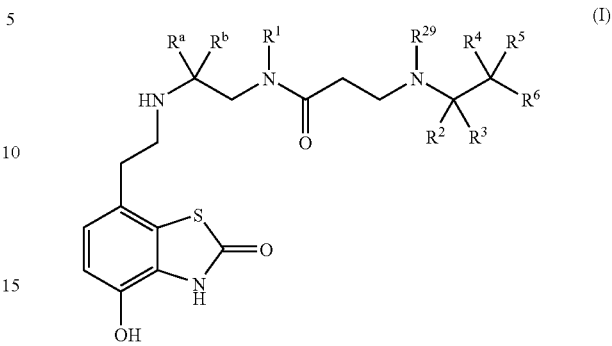

wherein $R^a$ and $R^b$ are, independently, hydrogen or $C_{1-3}$ alkyl; or $R^a$ and $R^b$, together with the carbon to which they are attached, form a cyclopropyl or cyclobutyl ring;

$R^1$ is: an α- or β-branched $C_{3-12}$ alkyl (optionally substituted by halogen, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, OC(O) ($C_{1-6}$ alkyl), $C_{3-12}$ cycloalkyl or $R^{28}$), $CH_2(C_{3-12}$ cycloalkyl) (the cycloalkyl ring being optionally substituted by halogen, $C_{1-6}$ alkyl, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, OC(O)($C_{1-6}$ alkyl), $C_{3-12}$ cycloalkyl or $R^{28}$), $C_{3-12}$ cycloalkyl (optionally substituted by halogen, $C_{1-6}$ alkyl, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, OC(O)($C_{1-6}$ alkyl), $C_{3-12}$ cycloalkyl or $R^{28}$) or $R^{28}$;

$R^6$ is a 5- to 14-membered aromatic or heteroaromatic ring system which is optionally substituted by halogen, hydroxy, carboxyl, $C_{1-6}$ alkyl (optionally substituted by halogen or —$NR^7R^8$), $C_{1-6}$ alkoxy (optionally substituted by halogen or —$NR^9R^{10}$), $C_{3-6}$ cycloalkyl, $C_{1-6}$ alkoxycarbonyl, —$NR^{11}R^{12}$, $C_{1-6}$ alkylcarbonylamino, $C_{1-6}$ alkylsulphonylamino, phenylsulphonylamino, —C(O)$NHR^{13}$, —$SO_2NHR^{14}$, $C_{1-6}$ alkylS(O)$_p$ (optionally substituted by halogen), $C_{2-4}$ alkenyl, $C_{2-4}$ alkynyl, cyano or $C_{0-6}$ alkyl-$R^{15}$, or a phenyl or 5- or 6-membered heteroaromatic ring (each of which is optionally substituted by halogen, trifluoromethyl, hydroxy, $C_{1-6}$ alkyl, $C_{1-6}$ alkoxy or —$NR^{16}R^{17}$); $R^6$ can also be $C_{1-6}$ haloalkyl;

p is 0, 1 or 2;

$R^{13}$ is hydrogen, $C_{1-6}$ alkyl, phenyl-$C_{0-6}$ alkyl or $C_{2-6}$ alkylene-$NR^{18}R^{19}$;

either $R^{18}$ and $R^{19}$ are, independently, hydrogen or $C_{1-6}$ alkyl, or $R^{18}$ and $R^{19}$ together with the nitrogen atom to which they are attached form a 4- to 6-membered saturated heterocyclic ring optionally comprising a further ring heteroatom selected from nitrogen and oxygen;

$R^{14}$ is hydrogen, $C_{1-6}$ alkyl, phenyl-$C_{0-6}$ alkyl or $C_{2-6}$ alkylene-$NR^{20}R^{21}$;

$R^{15}$ is a saturated, 5- or 6-membered nitrogen-containing ring;

$R^2, R^3, R^5, R^7, R^8, R^9, R^{10}, R^{11}, R^{12}, R^{16}, R^{17}, R^{26}, R^{27}$ and $R^{29}$ are, independently, hydrogen or $C_{1-6}$ alkyl;

$R^4$ is hydrogen, hydroxy or $C_{1-6}$ alkyl;

either $R^{20}$ and $R^{21}$ are, independently, hydrogen or $C_{1-6}$ alkyl, or $R^{20}$ and $R^{21}$ together with the nitrogen atom to which they are attached form a 4- to 6-membered saturated heterocyclic ring optionally comprising a further ring heteroatom selected from nitrogen and oxygen;

$R^{28}$ is a 4- to 7-membered heterocyclyl comprising a ring nitrogen (optionally substituted by $C(O)(C_{1-6}$ alkyl)), oxygen or sulphur; the ring $R^{28}$ being optionally substituted by $C_{1-6}$ alkyl, and ring carbon atoms which are not adjacent to a ring heteroatom are optionally substituted by halogen, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{18}R^{19}$, $OC(O)(C_{1-6}$ alkyl) or $C_{3-12}$ cycloalkyl;

or a pharmaceutically acceptable salt thereof.

In the context of the present specification, unless otherwise stated, an alkyl substituent group or an alkyl moiety in a substituent group may be linear or branched. Examples of $C_{1-6}$ alkyl groups/moieties include methyl, ethyl, n-propyl, iso-propyl, n-butyl, iso-butyl, tert-butyl, n-pentyl, n-hexyl and 1-methylpentyl. Similarly, an alkylene group may be linear or branched. Examples of $C_{1-6}$ alkylene groups include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene. The alkyl moieties in a di-$C_{1-6}$ alkylamino, di-$C_{1-6}$ alkylaminocarbonyl or di-$C_{1-6}$ alkylaminosulphonyl substituent group may be the same or different.

Halogen is, for example, fluorine, chlorine or bromine.

Haloalkyl is an alkyl carrying one or more halogen atoms. It is, for example, $CF_3$, $C_2F_5$, $CH_2CF_3$ or $CHF_2$.

Cycloalkyl is a non-aromatic ring that can comprise one, two or three non-aromatic rings, and is, optionally, fused to a benzene ring (for example to form an indanyl, or 1,2,3,4-tetrahydronaphthyl ring). Examples of cycloalkyl include cyclopropyl, cyclobutyl, cyclopentyl, cyclohexyl, cycloheptyl, bicyclo[2.2.1]heptyl, cyclopentenyl, cyclohexenyl or adamantyl.

A 5- or 6-membered heteroaromatic ring is, for example, a 5- or 6-membered ring comprising one, two or three heteroatoms selected from nitrogen, oxygen or sulphur. It is, for example, imidazolyl, pyrazolyl, 1,2,3-triazolyl, 1,2,4-triazolyl, thiazolyl, oxazolyl, isoxazolyl, pyridinyl, pyrimidinyl, pyrazinyl or pyridazinyl.

Phenyl-$C_{0-6}$ alkyl is, for example, phenyl, benzyl, 1-phenyleth-1-yl or 2-phenyleth-2-yl.

A saturated, 5- or 6-membered nitrogen-containing ring is, for example, piperidinyl, morpholinyl, thiomorpholinyl, piperazinyl or pyrrolidinyl.

A 4- to 6-membered saturated heterocyclic ring (formed when $R^{18}$ and $R^{19}$, or $R^{20}$ and $R^{21}$, together with the nitrogen to which they are attached, form a ring) is, for example, tetrahydropyranyl, tetrahydrofuryl, tetrahydrothiopyranyl, piperidinyl, morpholinyl, thiomorpholinyl, piperazinyl or pyrrolidinyl.

The compounds of the invention are selective β2 receptor agonists and possess properties that make them suitable for once-a-day administration. Compounds have been optimised to have appropriate duration in an in vitro guinea pig trachea model, or mammalian model such as a histamine-challenged guinea pig. The compounds also have advantageous pharmokinetic half lives in mammalian systems. In particular, certain compounds of the invention are at least 10-fold more potent at the β2 receptor compared to the α1, β1, or dopamine (D2) receptors. The compounds are also notable for having a fast onset of action that is the time interval between administration of a compound of the invention to a patient and the compound providing symptomatic relief. Onset can be predicted in vitro using isolated trachea from guinea pig or human.

Incorporation of an α- or β-branched alkyl group as $R^1$ advantageously provides increased chemical stability relative to compounds having a straight chain alkyl at this position.

Incorporation of a second amine basic centre in the chain 2 carbon atoms from the amide carbonyl group gives both long in vivo duration (as shown by rat iv pharmacokinetic half-life), and fast onset of action.

A suitable pharmaceutically acceptable salt is, for example, an acid addition salt such as a hydrochloride (for example a monohydrochloride or a dihydrochloride), hydrobromide (for example a monohydrobromide or a dihydrobromide), trifluoroacetate (for example a mono-trifluoroacetate or a di-trifluoroacetate), sulphate, phosphate, acetate, fumarate, maleate, tartrate, lactate, citrate, pyruvate, succinate, oxalate, methanesulphonate or p-toluenesulphonate. Further examples of acid addition salts are: bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate and 2-naphthalenesulphonate. Still further examples of acid addition salts are: D-mandelate, L-mandelate, 2,5-dichlorobenzenesulphonate, cinnamate and benzoate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

In one particular aspect the present invention provides a compound of formula (I) wherein: $R^a$ and $R^b$ are both hydrogen; $R^1$ is: an α- or β-branched $C_{3-12}$ alkyl (optionally substituted by halogen, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, $OC(O)(C_{1-6}$ alkyl), $C_{3-12}$ cycloalkyl or $R^{28}$), $CH_2(C_{3-12}$ cycloalkyl) (the cycloalkyl ring being optionally substituted by halogen, $C_{1-6}$ alkyl, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, $OC(O)(C_{1-6}$ alkyl), $C_{3-12}$ cycloalkyl or $R^{28}$), $C_{3-12}$ cycloalkyl (optionally substituted by halogen, $C_{1-6}$ alkyl, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, $OC(O)(C_{1-6}$ alkyl), $C_{3-12}$ cycloalkyl or $R^{28}$) or $R^{28}$; $R^6$ is a 5- to 14-membered aromatic or heteroaromatic ring system which is optionally substituted by halogen, hydroxy, carboxyl, $C_{1-6}$ alkyl (optionally substituted by halogen or —$NR^7R^8$), $C_{1-6}$ alkoxy (optionally substituted by halogen or —$NR^9R^{10}$), $C_{3-6}$ cycloalkyl, $C_{1-6}$ alkoxycarbonyl, —$NR^{11}R^{12}$, $C_{1-6}$ alkylcarbonylamino, $C_{1-6}$ alkylsulphonylamino, phenylsulphonylamino, —$C(O)NHR^{13}$, —$SO_2NHR^{14}$, $C_{1-6}$ alkylS(O)$_p$ (optionally substituted by halogen), $C_{2-4}$ alkenyl, $C_{2-4}$ alkynyl, cyano or $C_{0-6}$ alkyl-$R^{15}$, or a phenyl or 5- or 6-membered heteroaromatic ring (each of which is optionally substituted by halogen, trifluoromethyl, hydroxy, $C_{1-6}$ alkyl, $C_{1-6}$ alkoxy or —$NR^{16}R^{17}$); p is 0, 1 or 2; $R^{13}$ is hydrogen, $C_{1-6}$ alkyl, phenyl-$C_{0-6}$ alkyl or $C_{2-6}$ alkylene-$NR^{18}R^{19}$; either $R^{18}$ and $R^{19}$ are, independently, hydrogen or $C_{1-6}$ alkyl, or $R^{18}$ and $R^{19}$ together with the nitrogen atom to which they are attached form a 4- to 6-membered saturated heterocyclic ring optionally comprising a further ring heteroatom selected from nitrogen and oxygen; $R^{14}$ is hydrogen, $C_{1-6}$ alkyl, phenyl-$C_{0-6}$ alkyl or $C_{2-6}$ alkylene-$NR^{20}R^{21}$; $R^{15}$ is a saturated, 5- or 6-membered nitrogen-containing ring; $R^2$, $R^3$, $R^4$, $R^5$, $R^7$, $R^8$, $R^9$, $R^{10}$, $R^{11}$, $R^{12}$, $R^{16}$, $R^{17}$, $R^{26}$, $R^{27}$ and $R^{29}$ are, independently, hydrogen or $C_{1-6}$ alkyl; and, either $R^{20}$ and $R^{21}$ are, independently, hydrogen or $C_{1-6}$ alkyl, or $R^{20}$ and $R^{21}$ together with the nitrogen atom to which they are attached form a 4- to 6-membered saturated heterocyclic ring optionally comprising a further ring heteroatom selected from nitrogen and oxygen; $R^{28}$ is a 4- to 7-membered heterocyclyl comprising a ring nitrogen (optionally substituted by $C(O)$ ($C_{1-6}$ alkyl)), oxygen or sulphur; the ring $R^{28}$ being optionally substituted by $C_{1-6}$ alkyl, and ring carbon atoms which are not adjacent to a ring heteroatom are optionally substituted by halogen, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{18}R^{19}$, $OC(O)(C_{1-6}$ alkyl) or $C_{3-12}$ cycloalkyl; or a pharmaceutically acceptable salt thereof.

In another aspect the present invention provides a compound of formula (I) wherein each of $R^2$, $R^3$, $R^4$ and $R^5$ is, independently, hydrogen or $C_{1-4}$ alkyl (for example methyl).

In yet another aspect the present invention provides a compound of formula (I) wherein $R^2$, $R^3$, $R^4$ and $R^5$ are all hydrogen.

In a further aspect the present invention provides a compound of formula (I) wherein $R^{29}$ is hydrogen.

In a still further aspect the present invention provides a compound of formula (I) wherein $R^a$ and $R^b$ are both hydrogen.

In another aspect the present invention provides a compound of formula (I) wherein $R^1$ is $C_{3-6}$ cycloalkyl (optionally substituted by halogen, $C_{1-6}$ alkyl, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, $OC(O)(C_{1-6}$ alkyl), $C_{3-12}$ cycloalkyl or $R^{28}$); $R^{26}$ and $R^{27}$ are, independently, hydrogen or $C_{1-6}$ alkyl; $R^{28}$ is a 4- to 7-membered heterocyclyl comprising a ring nitrogen (optionally substituted by $C(O)(C_{1-6}$ alkyl)), oxygen or sulphur; the ring $R^{28}$ being optionally substituted by $C_{1-6}$ alkyl, and ring carbon atoms which are not adjacent to a ring heteroatom are optionally substituted by halogen, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{18}R^{19}$, $OC(O)(C_{1-6}$ alkyl or $C_{3-12}$ cycloalkyl; and $R^{18}$ and $R^{19}$ are, independently, hydrogen or $C_{1-6}$ alkyl.

In another aspect the present invention provides a compound of formula (I) wherein $R^1$ is $C_{7-12}$ cycloalkyl (optionally substituted by halogen, $C_{1-6}$ alkyl, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{26}R^{27}$, $OC(O)(C_{1-6}$ alkyl), $C_{3-12}$ cycloalkyl or $R^{28}$); $R^{26}$ and $R^{27}$ are, independently, hydrogen or $C_{1-6}$ alkyl; $R^{28}$ is a 4- to 7-membered heterocyclyl comprising a ring nitrogen (optionally substituted by $C(O)(C_{1-6}$ alkyl)), oxygen or sulphur; the ring $R^{28}$ being optionally substituted by $C_{1-6}$ alkyl, and ring carbon atoms which are not adjacent to a ring heteroatom are optionally substituted by halogen, $C_{1-6}$ alkoxy, $C_{1-6}$ alkylthio, $C_{1-6}$ alkylS(O), $C_{1-6}$ alkylS(O)$_2$, $C_{1-6}$ haloalkoxy, hydroxy, $NR^{18}R^{19}$, $OC(O)(C_{1-6}$ alkyl or $C_{3-12}$ cycloalkyl; and $R^{18}$ and $R^{19}$ are, independently, hydrogen or $C_{1-6}$ alkyl.

In another aspect the present invention provides a compound of formula (I) wherein $R^1$ is α- or β-branched $C_{3-6}$ alkyl (such as iso-propyl or $CH_2C(CH_3)_3$).

In a further aspect the present invention provides a compound of formula (I) wherein $R^1$ is iso-propyl or $CH_2C(CH_3)_3$.

In yet another aspect the present invention provides a compound of formula (I) wherein $R^1$ is $C_{5-8}$ cycloalkyl (such as cyclopentyl or cyclohexyl) optionally substituted by halogen (such as fluoro) or $C_{1-4}$ alkyl (such as methyl).

For example $R^1$ is cyclopentyl.

Alternatively, $R^1$ is cyclohexyl (optionally substituted by halogen (such as fluoro; for example to form 4,4-difluorocyclohexyl) or $C_{1-4}$ alkyl (such as methyl)). For example $R^1$ is cyclohexyl.

Alternatively, $R^1$ is cycloheptyl.

In yet another aspect the present invention provides a compound of formula (I) wherein $R^1$ is $C_{4-8}$ cycloalkyl optionally substituted by halogen (such as fluoro), for example $R^1$ is cyclopentyl, cyclohexyl (optionally substituted by halogen, for example fluoro; for example to form 4,4-difluorocyclohexyl) or cycloheptyl.

In a further aspect the present invention provides a compound of formula (I) wherein $R^1$ is $R^{28}$, for example tetrahydropyranyl.

In a still further aspect the present invention provides a compound of formula (I) wherein $R^6$ is a 5- to 14-membered (5-, 6-, 7-, 8-, 9-, 10-, 11-, 12-, 13- or 14-membered) aromatic or heteroaromatic ring system optionally substituted by none, one or more (e.g. none, one, two, three or four) substituents independently selected from halogen (e.g. fluorine, chlorine, bromine or iodine), trifluoromethyl, hydroxyl, carboxyl, $C_{1-6}$, or $C_{1-4}$, or $C_{1-2}$ alkyl (optionally substituted by none, one or more, e.g. none, one or two, —$NR^7R^8$), $C_{1-6}$, or $C_{1-4}$, or $C_{1-2}$ alkoxy (optionally substituted by none, one or more, e.g. none, one or two, —$NR^9R^{10}$), $C_{1-6}$, or $C_{1-4}$, or $C_{1-2}$ alkoxycarbonyl, —$NR^{11}R^{12}$, $C_{1-6}$, or $C_{1-4}$, or $C_{1-2}$ alkylcarbonylamino, $C_{1-6}$, or $C_{1-4}$, or $C_{1-2}$ alkylsulphonylamino, phenylsulphonylamino, —$C(O)NHR^{13}$, —$SO_2NHR^{14}$, $C_{0-6}$, or $C_{0-4}$, or $C_{0-2}$ alkyl-$R^{15}$, and phenyl or 5- or 6-membered heteroaromatic ring (each of which is unsubstituted or substituted by one or more, e.g. one, two, three or four, substituents independently selected from halogen such as fluorine, chlorine, bromine or iodine, trifluoromethyl, hydroxyl, $C_{1-6}$, or $C_{1-4}$, or $C_{1-2}$ alkyl, $C_{1-6}$, or $C_{1-4}$, or $C_{1-2}$ alkoxy and —$NR^{16}R^{17}$).

In a further embodiment of the invention $R^6$ represents a 5- to 14-membered (6-, 7-, 8-, 9-, 10-, 11-, 12-, 13- or 14-membered) aromatic or heteroaromatic ring system optionally substituted by one or more (e.g. one, two, three or four) substituents independently selected from halogen (e.g. fluorine, chlorine, bromine or iodine), trifluoromethyl, hydroxyl, carboxyl, $C_{1-4}$ alkyl (optionally substituted by —$NR^7R^8$), $C_{1-4}$ alkoxy (optionally substituted by —$NR^9R^{10}$), $C_{1-4}$ alkoxycarbonyl, —$NR^{11}R^{12}$, $C_{1-4}$ alkylcarbonylamino, $C_{1-4}$ alkylsulphonylamino, phenylsulphonylamino, —$C(O)NHR^{13}$, —$SO_2NHR^{14}$ and $C_{0-4}$ alkyl-$R^{15}$.

When $R^6$ represents an optionally substituted 5- to 14-membered heteroaromatic ring system, the ring system comprises from 1 to 4 ring heteroatoms independently selected from nitrogen, oxygen and sulphur. Similarly, if a substituent in $R^6$ represents an optionally substituted 5- to 6-membered heteroaromatic ring, the ring comprises from 1 to 4 ring heteroatoms independently selected from nitrogen, oxygen and sulphur.

Examples of 5- to 14-membered (6- to 14-membered) aromatic or heteroaromatic ring systems that may be used, which may be monocyclic or polycyclic (e.g. bicyclic or tricyclic) in which the two or more rings are fused, include one or more (in any combination) of phenyl, naphthyl, pyridinyl, pyridazinyl, pyrimidinyl, pyrazinyl, 1,3,5-triazinyl, 1,2,4-triazinyl, azepinyl, oxepinyl, thiepinyl, indenyl, benzofuranyl, isobenzofuranyl, benzothiophenyl, indolyl, isoindolyl, benzimidazolyl, indazolyl, benzisoxazolyl, benzoxazolyl, benzothiazolyl, quinolinyl, isoquinolinyl, quinazolinyl, quinoxalinyl and dibenzofuranyl. Further examples are 1,3-benzodioxolyl and 2,3-dihydro-1,4-benzodioxoinyl. For example the ring systems include phenyl, pyridinyl, thienyl, benzthiazolyl or benzimidazolyl. For example the ring systems include phenyl, pyridinyl, thienyl or benzimidazolyl.

In a still further aspect the present invention provides a compound of formula (I) wherein $R^6$ is optionally substituted by halogen (for example fluoro or chloro), hydroxy, $C_{1-4}$ alkyl (such as methyl), $C_{1-4}$ alkoxy (such as methoxy), $C_{1-4}$ haloalkoxy (such as $OCHF_2$) or $S(O)_2NH_2$.

In another aspect the present invention provides a compound of formula (I) wherein $R^6$ is phenyl optionally substituted by halogen (for example fluoro, chloro or bromo), hydroxy, $C_{1-4}$ alkyl (such as methyl), $C_{1-4}$ alkoxy (such as methoxy), $CF_3$, $OCF_3$ or $S(O)_2NH_2$.

In a still further aspect the present invention provides a compound of formula (I) wherein $R^6$ is phenyl optionally substituted by halogen (for example fluoro, chloro or bromo), hydroxy, $C_{1-4}$ alkyl (such as methyl), $C_{1-4}$ alkoxy, $CF_3$ or $OCF_3$.

In another aspect the present invention provides a compound of formula (I) wherein $R^6$ is phenyl optionally substituted by fluoro, chloro, $C_{1-4}$ alkyl (such as methyl) or $C_{1-4}$ alkoxy (such as methoxy).

In yet another aspect the present invention provides a compound of formula (I) wherein $R^6$ is phenyl optionally substituted by fluoro or chloro.

In another aspect the present invention provides a compound of formula (I) wherein $R^a$, $R^b$ and $R^{29}$ are all hydrogen; $R^1$ is iso-propyl, $CH_2C(CH_3)_3$, cyclopentyl, cyclohexyl or cycloheptyl {for example $R^1$ is cyclohexyl or cycloheptyl}; $R^2$, $R^3$ and $R^5$ are, independently, hydrogen or $C_{1-4}$ alkyl (for example methyl) {for example $R^2$, $R^3$ and $R^5$ are all hydrogen}; $R^4$ is hydrogen, hydroxy or $C_{1-4}$ alkyl (for example methyl) {for example $R^4$ is hydrogen}; and $R^6$ is phenyl optionally substituted by fluoro, chloro, $C_{1-4}$ alkyl (such as methyl) or $C_{1-4}$ alkoxy (such as methoxy); or a pharmaceutically acceptable salt thereof (for example an acetic acid salt, a hydrobromide salt, a D-mandelate salt or a benzoate salt).

Each of the following compounds is an example of a compound of formula (I):

N-(2-{[2-(4-Hydroxy-2-oxo-2,3-dihydro-1,3-benzothiazol-7-yl)ethyl]amino}ethyl)-N-isopropyl-$N^3$-(2-phenylethyl)-β-alaninamide;

N-Cyclopentyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

$N^3$-[2-(4-Chlorophenyl)ethyl]-N-(2-{[2-(4-hydroxy-2-oxo-2,3-dihydro-1,3-benzothiazol-7-yl)ethyl]amino}ethyl)-N-isopropyl-β-alaninamide;

N-(4,4-Difluorocyclohexyl)-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-(2,2-Dimethylpropyl)-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

$N^3$-[2-(3-Chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

$N^3$-[2-(4-Chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

$N^3$-[2-(3,4-Dichlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

N-(2,2-Dimethylpropyl)-N-(2-{[2-(4-hydroxy-2-oxo-2,3-dihydro-1,3-benzothiazol-7-yl)ethyl]amino}ethyl)-$N^3$-[2-(3-methylphenyl)ethyl]-β-alaninamide;

N-(2,2-Dimethylpropyl)-N-(2-{[2-(4-hydroxy-2-oxo-2,3-dihydro-1,3-benzothiazol-7-yl)ethyl]amino}ethyl)-$N^3$-[(2S)-2-phenylpropyl]-β-alaninamide;

$N^3$-[2-(3-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide;

$N^3$-[2-(4-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[2-(3-methylphenyl)ethyl]-β-alaninamide;

N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Cyclohexyl-$N^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

$N^3$-[2-(2-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[(2S)-2-phenylpropyl]-β-alaninamide;

N-Cyclohexyl-$N^3$-(1,1-dimethyl-2-phenylethyl)-N-(2-{[2-(4-hydroxy-2-oxo-2,3-dihydro-1,3-benzothiazol-7-yl)ethyl]amino}ethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[(2R)-2-phenylpropyl]-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-(2-methyl-2-phenylpropyl)-β-alaninamide;

$N^3$-[2-(3-Chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide;

N-Cycloheptyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-cyclohexyl-$N^3$-[2-(2-fluorophenyl)ethyl]-N-(2-{[2-(4-hydroxy-2-oxo-2,3-dihydro-1,3-benzothiazol-7-yl)ethyl]amino}ethyl)-β-alaninamide;

N-cyclohexyl-N-(2-{[2-(4-hydroxy-2-oxo-2,3-dihydro-1,3-benzothiazol-7-yl)ethyl]amino}ethyl)-$N^3$-[2-(2-methylphenyl)ethyl]-β-alaninamide;

N-cyclohexyl-N-(2-{[2-(4-hydroxy-2-oxo-2,3-dihydro-1,3-benzothiazol-7-yl)ethyl]amino}ethyl)-$N^3$-[2-(4-methylphenyl)ethyl]-β-alaninamide;

N-(2,2-dimethylpropyl)-$N^3$-[2-(2-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(2,2-dimethylpropyl)-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(2,2-dimethylpropyl)-$N^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(2,2-dimethylpropyl)-N-(2-{[2-(4-hydroxy-2-oxo-2,3-dihydro-1,3-benzothiazol-7-yl)ethyl]amino}ethyl)-$N^3$-(2-phenylpropyl)-β-alaninamide;

N-(2,2-dimethylpropyl)-N-(2-{[2-(4-hydroxy-2-oxo-2,3-dihydro-1,3-benzothiazol-7-yl)ethyl]amino}ethyl)-$N^3$-[2-(2-methylphenyl)ethyl]-β-alaninamide;

N-(2,2-dimethylpropyl)-N-(2-{[2-(4-hydroxy-2-oxo-2,3-dihydro-1,3-benzothiazol-7-yl)ethyl]amino}ethyl)-N$^3$-[2-(4-methylphenyl)ethyl]-β-alaninamide;

N$^3$-[2-(2-chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

N$^3$-(1,1-dimethyl-2-phenylethyl)-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

N-(2,2-dimethylpropyl)-N-(2-{[2-(4-hydroxy-2-oxo-2,3-dihydro-1,3-benzothiazol-7-yl)ethyl]amino}ethyl)-N$^3$-(2-methyl-2-phenylpropyl)-β-alaninamide;

N-(2,2-dimethylpropyl)-N-(2-{[2-(4-hydroxy-2-oxo-2,3-dihydro-1,3-benzothiazol-7-yl)ethyl]amino}ethyl)-N$^3$-[2-(5,6,7,8-tetrahydronaphthalen-1-yl)ethyl]-β-alaninamide;

N-(4,4-difluorocyclohexyl)-N$^3$-[2-(2-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(4,4-difluorocyclohexyl)-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(4,4-difluorocyclohexyl)-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(4,4-difluorocyclohexyl)-N-(2-{[2-(4-hydroxy-2-oxo-2,3-dihydro-1,3-benzothiazol-7-yl)ethyl]amino}ethyl)-N$^3$-[2-(2-methylphenyl)ethyl]-β-alaninamide;

N-(4,4-difluorocyclohexyl)-N-(2-{[2-(4-hydroxy-2-oxo-2,3-dihydro-1,3-benzothiazol-7-yl)ethyl]amino}ethyl)-N$^3$-[2-(3-methylphenyl)ethyl]-β-alaninamide;

N-(4,4-difluorocyclohexyl)-N-(2-{[2-(4-hydroxy-2-oxo-2,3-dihydro-1,3-benzothiazol-7-yl)ethyl]amino}ethyl)-N$^3$-[2-(4-methylphenyl)ethyl]-β-alaninamide;

N-(4,4-difluorocyclohexyl)-N-(2-{[2-(4-hydroxy-2-oxo-2,3-dihydro-1,3-benzothiazol-7-yl)ethyl]amino}ethyl)-N$^3$-(2-phenylpropyl)-β-alaninamide;

N$^3$-[2-(2-chlorophenyl)ethyl]-N-(4,4-difluorocyclohexyl)-N-(2-{[2-(4-hydroxy-2-oxo-2,3-dihydro-1,3-benzothiazol-7-yl)ethyl]amino}ethyl)-β-alaninamide;

N$^3$-[2-(3-chlorophenyl)ethyl]-N-(4,4-difluorocyclohexyl)-N-(2-{[2-(4-hydroxy-2-oxo-2,3-dihydro-1,3-benzothiazol-7-yl)ethyl]amino}ethyl)-β-alaninamide;

N$^3$-[2-(4-chlorophenyl)ethyl]-N-(4,4-difluorocyclohexyl)-N-(2-{[2-(4-hydroxy-2-oxo-2,3-dihydro-1,3-benzothiazol-7-yl)ethyl]amino}ethyl)-β-alaninamide;

N-(4,4-difluorocyclohexyl)-N$^3$-(1,1-dimethyl-2-phenylethyl)-N-(2-{[2-(4-hydroxy-2-oxo-2,3-dihydro-1,3-benzothiazol-7-yl)ethyl]amino}ethyl)-β-alaninamide;

N-(4,4-difluorocyclohexyl)-N-(2-{[2-(4-hydroxy-2-oxo-2,3-dihydro-1,3-benzothiazol-7-yl)ethyl]amino}ethyl)-N$^3$-(2-methyl-2-phenylpropyl)-β-alaninamide;

N$^3$-[2-(3,4-dichlorophenyl)ethyl]-N-(4,4-difluorocyclohexyl)-N-(2-{[2-(4-hydroxy-2-oxo-2,3-dihydro-1,3-benzothiazol-7-yl)ethyl]amino}ethyl)-β-alaninamide;

N-(4,4-difluorocyclohexyl)-N-(2-{[2-(4-hydroxy-2-oxo-2,3-dihydro-1,3-benzothiazol-7-yl)ethyl]amino}ethyl)-N$^3$-[2-(5,6,7,8-tetrahydronaphthalen-1-yl)ethyl]-β-alaninamide;

N-(2-{[2-(4-hydroxy-2-oxo-2,3-dihydro-1,3-benzothiazol-7-yl)ethyl]amino}ethyl)-N-isopropyl-N$^3$-[2-(5,6,7,8-tetrahydronaphthalen-1-yl)ethyl]-β-alaninamide;

N$^3$-[2-(3,4-dichlorophenyl)ethyl]-N-(2-{[2-(4-hydroxy-2-oxo-2,3-dihydro-1,3-benzothiazol-7-yl)ethyl]amino}ethyl)-N-isopropyl-β-alaninamide;

N-(2-{[2-(4-hydroxy-2-oxo-2,3-dihydro-1,3-benzothiazol-7-yl)ethyl]amino}ethyl)-N-isopropyl-N$^3$-(2-methyl-2-phenylpropyl)-β-alaninamide;

N$^3$-(1,1-dimethyl-2-phenylethyl)-N-(2-{[2-(4-hydroxy-2-oxo-2,3-dihydro-1,3-benzothiazol-7-yl)ethyl]amino}ethyl)-N-isopropyl-β-alaninamide;

N$^3$-[2-(2-chlorophenyl)ethyl]-N-(2-{[2-(4-hydroxy-2-oxo-2,3-dihydro-1,3-benzothiazol-7-yl)ethyl]amino}ethyl)-N-isopropyl-β-alaninamide;

N$^3$-[2-(3-chlorophenyl)ethyl]-N-(2-{[2-(4-hydroxy-2-oxo-2,3-dihydro-1,3-benzothiazol-7-yl)ethyl]amino}ethyl)-N-isopropyl-β-alaninamide;

N-cyclopentyl-N$^3$-[2-(2-fluorophenyl)ethyl]-N-(2-{[2-(4-hydroxy-2-oxo-2,3-dihydro-1,3-benzothiazol-7-yl)ethyl]amino}ethyl)-β-alaninamide;

N-cyclopentyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-cyclopentyl-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N-cyclopentyl-N-(2-{[2-(4-hydroxy-2-oxo-2,3-dihydro-1,3-benzothiazol-7-yl)ethyl]amino}ethyl)-N$^3$-[2-(2-methylphenyl)ethyl]-β-alaninamide;

N-cyclopentyl-N-(2-{[2-(4-hydroxy-2-oxo-2,3-dihydro-1,3-benzothiazol-7-yl)ethyl]amino}ethyl)-N$^3$-[2-(3-methylphenyl)ethyl]-β-alaninamide;

N-cyclopentyl-N-(2-{[2-(4-hydroxy-2-oxo-2,3-dihydro-1,3-benzothiazol-7-yl)ethyl]amino}ethyl)-N$^3$-[2-(4-methylphenyl)ethyl]-β-alaninamide;

N$^3$-[2-(2-chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide;

N$^3$-[2-(3-chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide;

N$^3$-[2-(4-chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide;

N-cyclopentyl-N-(2-{[2-(4-hydroxy-2-oxo-2,3-dihydro-1,3-benzothiazol-7-yl)ethyl]amino}ethyl)-N$^3$-(2-phenylpropyl)-β-alaninamide;

N-cyclopentyl-N-(2-{[2-(4-hydroxy-2-oxo-2,3-dihydro-1,3-benzothiazol-7-yl)ethyl]amino}ethyl)-N$^3$-(2-methyl-2-phenylpropyl)-β-alaninamide;

N-cyclopentyl-N$^3$-(1,1-dimethyl-2-phenylethyl)-N-(2-{[2-(4-hydroxy-2-oxo-2,3-dihydro-1,3-benzothiazol-7-yl)ethyl]amino}ethyl)-β-alaninamide;

N-cyclopentyl-N$^3$-[2-(3,4-dichlorophenyl)ethyl]-N-(2-{[2-(4-hydroxy-2-oxo-2,3-dihydro-1,3-benzothiazol-7-yl)ethyl]amino}ethyl)-β-alaninamide;

N-cyclopentyl-N-(2-{[2-(4-hydroxy-2-oxo-2,3-dihydro-1,3-benzothiazol-7-yl)ethyl]amino}ethyl)-N$^3$-[2-(5,6,7,8-tetrahydronaphthalen-1-yl)ethyl]-β-alaninamide;

N-cycloheptyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-cycloheptyl-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N$^3$-[2-(3-chlorophenyl)ethyl]-N-cycloheptyl-N-(2-{[2-(4-hydroxy-2-oxo-2,3-dihydro-1,3-benzothiazol-7-yl)ethyl]amino}ethyl)-β-alaninamide;

N-cycloheptyl-N-(2-{[2-(4-hydroxy-2-oxo-2,3-dihydro-1,3-benzothiazol-7-yl)ethyl]amino}ethyl)-N$^3$-[2-(3-hydroxyphenyl)ethyl]-β-alaninamide;

N-cycloheptyl-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N-cycloheptyl-N-(2-{[2-(4-hydroxy-2-oxo-2,3-dihydro-1,3-benzothiazol-7-yl)ethyl]amino}ethyl)-N$^3$-[2-(4-methylphenyl)ethyl]-β-alaninamide;

N$^3$-[2-(4-chlorophenyl)ethyl]-N-cycloheptyl-N-(2-{[2-(4-hydroxy-2-oxo-2,3-dihydro-1,3-benzothiazol-7-yl)ethyl]amino}ethyl)-β-alaninamide;

N-(2-{[2-(4-hydroxy-2-oxo-2,3-dihydro-1,3-benzothiazol-7-yl)ethyl]amino}ethyl)-N$^3$-[2-(2-methylphenyl)ethyl]-N-(tetrahydro-2H-pyran-4-yl)-β-alaninamide;

N$^3$-[2-(3-chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide;

N$^3$-[2-(3,4-dichlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide;

N$^3$-[2-(4-chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide;

N-(2-{[2-(4-hydroxy-2-oxo-2,3-dihydro-1,3-benzothiazol-7-yl)ethyl]amino}ethyl)-N$^3$-[2-(4-methylphenyl)ethyl]-N-(tetrahydro-2H-pyran-4-yl)-β-alaninamide;

N-(2-{[2-(4-hydroxy-2-oxo-2,3-dihydro-1,3-benzothiazol-7-yl)ethyl]amino}ethyl)-N$^3$-[2-(5,6,7,8-tetrahydronaphthalen-1-yl)ethyl]-N-(tetrahydro-2H-pyran-4-yl)-β-alaninamide;

N-(2,3-dihydro-1H-inden-2-yl)-N-(2-{[2-(4-hydroxy-2-oxo-2,3-dihydro-1,3-benzothiazol-7-yl)ethyl]amino}ethyl)-N$^3$-(2-phenylethyl)-β-alaninamide;

N-(2,3-dihydro-1H-inden-2-yl)-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(2,3-dihydro-1H-inden-2-yl)-N-(2-{[2-(4-hydroxy-2-oxo-2,3-dihydro-1,3-benzothiazol-7-yl)ethyl]amino}ethyl)-N$^3$-[2-(3-methylphenyl)ethyl]-β-alaninamide;

N$^3$-[2-(3-chlorophenyl)ethyl]-N-(2,3-dihydro-1H-inden-2-yl)-N-(2-{[2-(4-hydroxy-2-oxo-2,3-dihydro-1,3-benzothiazol-7-yl)ethyl]amino}ethyl)-β-alaninamide;

N-(2,3-dihydro-1H-inden-2-yl)-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(2,3-dihydro-1H-inden-2-yl)-N-(2-{[2-(4-hydroxy-2-oxo-2,3-dihydro-1,3-benzothiazol-7-yl)ethyl]amino}ethyl)-N$^3$-[2-(4-methylphenyl)ethyl]-β-alaninamide;

N$^3$-[2-(4-chlorophenyl)ethyl]-N-(2,3-dihydro-1H-inden-2-yl)-N-(2-{[2-(4-hydroxy-2-oxo-2,3-dihydro-1,3-benzothiazol-7-yl)ethyl]amino}ethyl)-β-alaninamide;

N-(2-{[2-(4-hydroxy-2-oxo-2,3-dihydro-1,3-benzothiazol-7-yl)ethyl]amino}ethyl)-N-(1-isopropyl-2-methylpropyl)-4-[(2-phenylethyl)amino]butanamide;

4-{[2-(3-fluorophenyl)ethyl]amino}-N-(2-{[2-(4-hydroxy-2-oxo-2,3-dihydro-1,3-benzothiazol-7-yl)ethyl]amino}ethyl)-N-(1-isopropyl-2-methylpropyl)butanamide;

N-(2-{[2-(4-hydroxy-2-oxo-2,3-dihydro-1,3-benzothiazol-7-yl)ethyl]amino}ethyl)-N-(1-isopropyl-2-methylpropyl)-4-{[2-(3-methylphenyl)ethyl]amino}butanamide;

4-{[2-(3-chlorophenyl)ethyl]amino}-N-(2-{[2-(4-hydroxy-2-oxo-2,3-dihydro-1,3-benzothiazol-7-yl)ethyl]amino}ethyl)-N-(1-isopropyl-2-methylpropyl)butanamide;

4-{[2-(4-fluorophenyl)ethyl]amino}-N-(2-{[2-(4-hydroxy-2-oxo-2,3-dihydro-1,3-benzothiazol-7-yl)ethyl]amino}ethyl)-N-(1-isopropyl-2-methylpropyl)butanamide;

N-(2-{[2-(4-hydroxy-2-oxo-2,3-dihydro-1,3-benzothiazol-7-yl)ethyl]amino}ethyl)-N-(1-isopropyl-2-methylpropyl)-4-{[2-(4-methylphenyl)ethyl]amino}butanamide;

4-{[2-(4-chlorophenyl)ethyl]amino}-N-(2-{[2-(4-hydroxy-2-oxo-2,3-dihydro-1,3-benzothiazol-7-yl)ethyl]amino}ethyl)-N-(1-isopropyl-2-methylpropyl)butanamide;

N$^3$-[2-(3-chlorophenyl)ethyl]-N-(3-hydroxy-2,2-dimethylpropyl)-N-(2-{[2-(4-hydroxy-2-oxo-2,3-dihydro-1,3-benzothiazol-7-yl)ethyl]amino}ethyl)-β-alaninamide;

N$^3$-[2-(3,4-dichlorophenyl)ethyl]-N-(3-hydroxy-2,2-dimethylpropyl)-N-(2-{[2-(4-hydroxy-2-oxo-2,3-dihydro-1,3-benzothiazol-7-yl)ethyl]amino}ethyl)-β-alaninamide;

N$^3$-[2-(4-chlorophenyl)ethyl]-N-(3-hydroxy-2,2-dimethylpropyl)-N-(2-{[2-(4-hydroxy-2-oxo-2,3-dihydro-1,3-benzothiazol-7-yl)ethyl]amino}ethyl)-β-alaninamide;

N-(3-hydroxy-2,2-dimethylpropyl)-N-(2-{[2-(4-hydroxy-2-oxo-2,3-dihydro-1,3-benzothiazol-7-yl)ethyl]amino}ethyl)-N$^3$-[2-(5,6,7,8-tetrahydronaphthalen-1-yl)ethyl]-β-alaninamide;

N-1-adamantyl-N-(2-{[2-(4-hydroxy-2-oxo-2,3-dihydro-1,3-benzothiazol-7-yl)ethyl]amino}ethyl)-N$^3$-(2-phenylethyl)-β-alaninamide;

N-1-adamantyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-1-adamantyl-N-(2-{[2-(4-hydroxy-2-oxo-2,3-dihydro-1,3-benzothiazol-7-yl)ethyl]amino}ethyl)-N$^3$-[2-(3-methylphenyl)ethyl]-β-alaninamide;

N-1-adamantyl-N-(2-{[2-(4-hydroxy-2-oxo-2,3-dihydro-1,3-benzothiazol-7-yl)ethyl]amino}ethyl)-N$^3$-[2-(3-hydroxyphenyl)ethyl]-β-alaninamide;

N-1-adamantyl-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N-1-adamantyl-N-(2-{[2-(4-hydroxy-2-oxo-2,3-dihydro-1,3-benzothiazol-7-yl)ethyl]amino}ethyl)-N$^3$-[2-(4-methylphenyl)ethyl]-β-alaninamide;

N-(1-adamantylmethyl)-N-(2-{[2-(4-hydroxy-2-oxo-2,3-dihydro-1,3-benzothiazol-7-yl)ethyl]amino}ethyl)-N$^3$-(2-phenylethyl)-β-alaninamide;

N-(1-adamantylmethyl)-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-(1-adamantylmethyl)-N-(2-{[2-(4-hydroxy-2-oxo-2,3-dihydro-1,3-benzothiazol-7-yl)ethyl]amino}ethyl)-N$^3$-[2-(3-hydroxyphenyl)ethyl]-β-alaninamide;

N-(1-adamantylmethyl)-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Benzyl-4-[2-({3-[cycloheptyl(2-{[2-(4-hydroxy-2-oxo-2,3-dihydro-1,3-benzothiazol-7-yl)ethyl]amino}ethyl)amino]-3-oxopropyl}amino)ethyl]benzamide;

N-(2-{[2-(4-Hydroxy-2-oxo-2,3-dihydro-1,3-benzothiazol-7-yl)ethyl]amino}ethyl)-N-[(1R)-1-methylpentyl]-N$^3$-(2-phenylethyl)-β-alaninamide;

N-(2-{[2-(4-Hydroxy-2-oxo-2,3-dihydro-1,3-benzothiazol-7-yl)ethyl]amino}ethyl)-N-[(1S)-1-methylpentyl]-N$^3$-(2-phenylethyl)-β-alaninamide;

N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Cycloheptyl-N-(2-{[2-(4-hydroxy-2-oxo-2,3-dihydro-1,3-benzothiazol-7-yl)ethyl]amino}ethyl)-N$^3$-(2-phenylethyl)-β-alaninamide;

N-Cycloheptyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-Benzyl-4-[2-({3-[cycloheptyl(2-{[2-(4-hydroxy-2-oxo-2,3-dihydro-1,3-benzothiazol-7-yl)ethyl]amino}ethyl)amino]-3-oxopropyl}amino)ethyl]benzamide;

N-(2-{[2-(4-Hydroxy-2-oxo-2,3-dihydro-1,3-benzothiazol-7-yl)ethyl]amino}ethyl)-N-[(1R)-1-methylpentyl]-$N^3$-(2-phenylethyl)-β-alaninamide;

N-(2-{[2-(4-Hydroxy-2-oxo-2,3-dihydro-1,3-benzothiazol-7-yl)ethyl]amino}ethyl)-N-[(1S)-1-methylpentyl]-$N^3$-(2-phenylethyl)-β-alaninamide;

N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Cycloheptyl-$N^3$-[2-(3-fluorophenyl)ethyl]-N-(2-{[2-(4-hydroxy-2-oxo-2,3-dihydro-1,3-benzothiazol-7-yl)ethyl]amino}propyl)-β-alaninamide; or, N-Cyclohexyl-N-(2-{[2-(4-hydroxy-2-oxo-2,3-dihydro-1,3-benzothiazol-7-yl)ethyl]amino}propyl)-$N^3$-(2-phenylethyl)-β-alaninamide;

or a pharmaceutically acceptable salt thereof.

In a further aspect the present invention provides each individual compound:

N-(2-{[2-(4-Hydroxy-2-oxo-2,3-dihydro-1,3-benzothiazol-7-yl)ethyl]amino}ethyl)-N-isopropyl-$N^3$-(2-phenylethyl)-β-alaninamide;

N-Cyclopentyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

$N^3$-[2-(4-Chlorophenyl)ethyl]-N-(2-{[2-(4-hydroxy-2-oxo-2,3-dihydro-1,3-benzothiazol-7-yl)ethyl]amino}ethyl)-N-isopropyl-β-alaninamide;

N-(4,4-Difluorocyclohexyl)-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-(2,2-Dimethylpropyl)-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

$N^3$-[2-(3-Chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

$N^3$-[2-(4-Chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

$N^3$-[2-(3,4-Dichlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

N-(2,2-Dimethylpropyl)-N-(2-{[2-(4-hydroxy-2-oxo-2,3-dihydro-1,3-benzothiazol-7-yl)ethyl]amino}ethyl)-$N^3$-[2-(3-methylphenyl)ethyl]-β-alaninamide;

N-(2,2-Dimethylpropyl)-N-(2-{[2-(4-hydroxy-2-oxo-2,3-dihydro-1,3-benzothiazol-7-yl)ethyl]amino}ethyl)-$N^3$-[(2S)-2-phenylpropyl]-β-alaninamide;

$N^3$-[2-(3-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide;

$N^3$-[2-(4-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[2-(3-methylphenyl)ethyl]-β-alaninamide;

N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Cyclohexyl-$N^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide;

$N^3$-[2-(2-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[(2S)-2-phenylpropyl]-β-alaninamide;

N-Cyclohexyl-$N^3$-(1,1-dimethyl-2-phenylethyl)-N-(2-{[2-(4-hydroxy-2-oxo-2,3-dihydro-1,3-benzothiazol-7-yl)ethyl]amino}ethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[(2R)-2-phenylpropyl]-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-(2-methyl-2-phenylpropyl)-β-alaninamide;

$N^3$-[2-(3-Chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide;

N-Cycloheptyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

$N^3$-[2-(3,4-Dichlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide;

N-(2-{[2-(4-Hydroxy-2-oxo-2,3-dihydro-1,3-benzothiazol-7-yl)ethyl]amino}ethyl)-$N^3$-[2-(3-methylphenyl)ethyl]-N-(tetrahydro-2H-pyran-4-yl)-β-alaninamide;

$N^3$-[2-(4-Chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide;

N-(2-{[2-(4-Hydroxy-2-oxo-2,3-dihydro-1,3-benzothiazol-7-yl)ethyl]amino}ethyl)-$N^3$-[2-(2-methylphenyl)ethyl]-N-(tetrahydro-2H-pyran-4-yl)-β-alaninamide;

$N^3$-[2-(4-Chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide;

$N^3$-[2-(2-Chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide;

$N^3$-[2-(3-Chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide;

N-Cyclopentyl-N-(2-{[2-(4-hydroxy-2-oxo-2,3-dihydro-1,3-benzothiazol-7-yl)ethyl]amino}ethyl)-$N^3$-[(2S)-2-phenylpropyl]-β-alaninamide;

N-Cyclopentyl-N-(2-{[2-(4-hydroxy-2-oxo-2,3-dihydro-1,3-benzothiazol-7-yl)ethyl]amino}ethyl)-$N^3$-(2-methyl-2-phenylpropyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-(2-pyridin-2-ylethyl)-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[2-(4-hydroxyphenyl)ethyl]-β-alaninamide;

N-Cyclohexyl-N-(2-{[2-(4-hydroxy-2-oxo-2,3-dihydro-1,3-benzothiazol-7-yl)ethyl]amino}ethyl)-$N^3$-[2-(2-thienyl)ethyl]-β-alaninamide;

N-Cycloheptyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Cycloheptyl-N-(2-{[2-(4-hydroxy-2-oxo-2,3-dihydro-1,3-benzothiazol-7-yl)ethyl]amino}ethyl)-$N^3$-[2-(3-hydroxyphenyl)ethyl]-β-alaninamide;

$N^3$-(1,1-Dimethyl-2-phenylethyl)-N-(2,2-dimethylpropyl)-N-(2-{[2-(4-hydroxy-2-oxo-2,3-dihydro-1,3-benzothiazol-7-yl)ethyl]amino}ethyl)-β-alaninamide;

3-[{N-[2-(4-Chlorophenyl)ethyl]-β-alanyl}(2-{[2-(4-hydroxy-2-oxo-2,3-dihydro-1,3-benzothiazol-7-yl)ethyl]amino}ethyl)amino]-2,2-dimethylpropyl acetate;

$N^3$-[2-(4-Chlorophenyl)ethyl]-N-(3-hydroxy-2,2-dimethylpropyl)-N-(2-{[2-(4-hydroxy-2-oxo-2,3-dihydro-1,3-benzothiazol-7-yl)ethyl]amino}ethyl)-β-alaninamide;

$N^1$-(2,3-Dihydro-1H-inden-2-yl)-$N^1$-(2-{[2-(4-hydroxy-2-oxo-2,3-dihydro-1,3-benzothiazol-7-yl)ethyl]amino}ethyl)-$N^3$-(2-phenylethyl)-β-alaninamide;

$N^3$-[2-(3-Chlorophenyl)ethyl]-$N^1$-(2,3-dihydro-1H-inden-2-yl)-$N^1$-(2-{[2-(4-hydroxy-2-oxo-2,3-dihydro-1,3-benzothiazol-7-yl)ethyl]amino}ethyl)-β-alaninamide;

$N^1$-(2,2-Dimethylpropyl)-$N^1$-(2-{[2-(4-hydroxy-2-oxo-2,3-dihydro-1,3-benzothiazol-7-yl)ethyl]amino}ethyl)-$N^3$-[2-(3-methoxyphenyl)ethyl]-β-alaninamide;

$N^1$-(2,2-Dimethylpropyl)-$N^3$-[2-(3-fluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-(2-{[2-(4-Hydroxy-2-oxo-2,3-dihydro-1,3-benzothiazol-7-yl)ethyl]amino}ethyl)-$N^1$-(2-methyl-2-phenylpropyl)-$N^3$-(2-phenylethyl)-β-alaninamide;

$N^3$-[2-(2-Chlorophenyl)ethyl]-$N^1$-(4,4-difluorocyclohexyl)-$N^1$-(2-{[2-(4-hydroxy-2-oxo-2,3-dihydro-1,3-benzothiazol-7-yl)ethyl]amino}ethyl)-β-alaninamide;

$N^3$-[2-(3-Chlorophenyl)ethyl]-$N^1$-(4,4-difluorocyclohexyl)-$N^1$-(2-{[2-(4-hydroxy-2-oxo-2,3-dihydro-1,3-benzothiazol-7-yl)ethyl]amino}ethyl)-β-alaninamide;

$N^3$-[2-(4-Chlorophenyl)ethyl]-$N^1$-(4,4-difluorocyclohexyl)-$N^1$-(2-{[2-(4-hydroxy-2-oxo-2,3-dihydro-1,3-benzothiazol-7-yl)ethyl]amino}ethyl)-β-alaninamide;

$N^3$-[2-(3,4-Dichlorophenyl)ethyl]-$N^1$-(4,4-difluorocyclohexyl)-$N^1$-(2-{[2-(4-hydroxy-2-oxo-2,3-dihydro-1,3-benzothiazol-7-yl)ethyl]amino}ethyl)-β-alaninamide;

$N^3$-[2-(3-Chlorophenyl)ethyl]-$N^1$-cycloheptyl-$N^1$-(2-{[2-(4-hydroxy-2-oxo-2,3-dihydro-1,3-benzothiazol-7-yl)ethyl]amino}ethyl)-β-alaninamide;

$N^3$-[2-(4-Chlorophenyl)ethyl]-$N^1$-cycloheptyl-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^1$-(2-{[2-(4-hydroxy-2-oxo-2,3-dihydro-1,3-benzothiazol-7-yl)ethyl]amino}ethyl)-$N^3$-[2-(2-thienyl)ethyl]-β-alaninamide;

$N^1$-Cycloheptyl-$N^3$-[2-(3,4-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^3$-{2-[3-(difluoromethoxy)phenyl]ethyl}-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^3$-[2-(2,4-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^3$-[2-(2,3-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^3$-[2-(2-Chloro-4-fluorophenyl)ethyl]-$N^1$-cycloheptyl-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^3$-[2-(3,5-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-(1-Adamantylmethyl)-$N^1$-(2-{[2-(4-hydroxy-2-oxo-2,3-dihydro-1,3-benzothiazol-7-yl)ethyl]amino}ethyl)-$N^3$-(2-phenylethyl)-β-alaninamide;

$N^1$-(1-Adamantylmethyl)-$N^3$-[2-(3-fluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-(1-Adamantylmethyl)-$N^3$-[2-(4-fluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-(2-{[2-(4-Hydroxy-2-oxo-2,3-dihydro-1,3-benzothiazol-7-yl)ethyl]amino}ethyl)-$N^3$-(2-phenylethyl)-$N^1$-(tetrahydro-2H-thiopyran-4-yl)-β-alaninamide;

$N^3$-[2-(3-Fluorophenyl)ethyl]-$N^1$-(2-{[2-(4-hydroxy-2-oxo-2,3-dihydro-1,3-benzothiazol-7-yl)ethyl]amino}ethyl)-$N^1$-(1-propylbutyl)-β-alaninamide;

$N^3$-[2-(4-Fluorophenyl)ethyl]-$N^1$-(2-{[2-(4-hydroxy-2-oxo-2,3-dihydro-1,3-benzothiazol-7-yl)ethyl]amino}ethyl)-$N^1$-(1-propylbutyl)-β-alaninamide;

$N^3$-[2-(2-Chlorophenyl)ethyl]-$N^1$-(3-hydroxy-2,2-dimethylpropyl)-$N^1$-(2-{[2-(4-hydroxy-2-oxo-2,3-dihydro-1,3-benzothiazol-7-yl)ethyl]amino}ethyl)-β-alaninamide;

$N^3$-[2-(3-Chlorophenyl)ethyl]-$N^1$-(3-hydroxy-2,2-dimethylpropyl)-$N^1$-(2-{[2-(4-hydroxy-2-oxo-2,3-dihydro-1,3-benzothiazol-7-yl)ethyl]amino}ethyl)-β-alaninamide;

$N^3$-[2-(2,3-Dichlorophenyl)ethyl]-$N^1$-(3-hydroxy-2,2-dimethylpropyl)-$N^1$-(2-{[2-(4-hydroxy-2-oxo-2,3-dihydro-1,3-benzothiazol-7-yl)ethyl]amino}ethyl)-β-alaninamide;

$N^1$-Cyclohexyl-$N^1$-(2-{[2-(4-hydroxy-2-oxo-2,3-dihydro-1,3-benzothiazol-7-yl)ethyl]amino}ethyl)-$N^3$-[2-(4-methoxyphenyl)ethyl]-β-alaninamide;

$N^3$-{2-[4-(Aminosulfonyl)phenyl]ethyl}-$N^1$-cyclohexyl-$N^1$-(2-{[2-(4-hydroxy-2-oxo-2,3-dihydro-1,3-benzothiazol-7-yl)ethyl]amino}ethyl)-β-alaninamide;

$N^1$-Cyclohexyl-$N^1$-(2-{[2-(4-hydroxy-2-oxo-2,3-dihydro-1,3-benzothiazol-7-yl)ethyl]amino}ethyl)-$N^3$-[2-(3-methoxyphenyl)ethyl]-β-alaninamide;

$N^1$-Cyclohexyl-$N^1$-(2-{[2-(4-hydroxy-2-oxo-2,3-dihydro-1,3-benzothiazol-7-yl)ethyl]amino}ethyl)-$N^3$-[2-(3-hydroxyphenyl)ethyl]-β-alaninamide;

$N^3$-[2-(5-Chloro-2-thienyl)ethyl]-$N^1$-cyclohexyl-$N^1$-(2-{[2-(4-hydroxy-2-oxo-2,3-dihydro-1,3-benzothiazol-7-yl)ethyl]amino}ethyl)-β-alaninamide;

$N^1$-Cyclohexyl-$N^3$-[2-(3,4-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cyclohexyl-$N^1$-(2-{[2-(4-hydroxy-2-oxo-2,3-dihydro-1,3-benzothiazol-7-yl)ethyl]amino}ethyl)-$N^3$-[(2S)-2-hydroxy-2-phenylethyl]-β-alaninamide;

$N^1$-Cyclohexyl-$N^1$-(2-{[2-(4-hydroxy-2-oxo-2,3-dihydro-1,3-benzothiazol-7-yl)ethyl]amino}ethyl)-$N^3$-[(2R)-2-hydroxy-2-phenylethyl]-β-alaninamide;

$N^3$-[2-(1,3-Benzodioxol-5-yl)ethyl]-$N^1$-cyclohexyl-$N^1$-(2-{[2-(4-hydroxy-2-oxo-2,3-dihydro-1,3-benzothiazol-7-yl)ethyl]amino}ethyl)-β-alaninamide;

$N^3$-[2-(1H-Benzimidazol-2-yl)ethyl]-$N^1$-cyclohexyl-$N^1$-(2-{[2-(4-hydroxy-2-oxo-2,3-dihydro-1,3-benzothiazol-7-yl)ethyl]amino}ethyl)-β-alaninamide;

$N^1$-Cyclohexyl-$N^3$-[2-(3,5-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cyclohexyl-$N^3$-[2-(2,5-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cyclohexyl-$N^1$-(2-{[2-(4-hydroxy-2-oxo-2,3-dihydro-1,3-benzothiazol-7-yl)ethyl]amino}ethyl)-$N^3$-(3,3,3-trifluoropropyl)-β-alaninamide;

$N^1$-Cyclohexyl-$N^3$-[2-(2,3-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^1$-(2-{[2-(4-hydroxy-2-oxo-2,3-dihydro-1,3-benzothiazol-7-yl)ethyl]amino}ethyl)-$N^3$-{2-[3-(trifluoromethyl)phenyl]ethyl}-β-alaninamide;

$N^1$-Cycloheptyl-$N^3$-[2-(2,5-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^3$-[2-(2,6-difluorophenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^1$-(2-{[2-(4-hydroxy-2-oxo-2,3-dihydro-1,3-benzothiazol-7-yl)ethyl]amino}ethyl)-$N^3$-[2-(3-methylphenyl)ethyl]-β-alaninamide;

$N^1$-Cycloheptyl-$N^3$-[2-(3,4-dimethoxyphenyl)ethyl]-$N^1$-(2-{[2-(4-hydroxy-2-oxo-2,3-dihydro-1,3-benzothiazol-7-yl)ethyl]amino}ethyl)-β-alaninamide;

$N^1$-Cycloheptyl-$N^3$-[2-(4-hydroxy-2-oxo-2,3-dihydro-1,3-benzothiazol-7-yl)ethyl]-N-(2-{[2-(4-hydroxy-2-oxo-2,3-dihydro-1,3-benzothiazol-7-yl)ethyl]amino}ethyl)-β-alaninamide;

$N^1$-Cycloheptyl-$N^3$-[2-(2,3-dihydro-1,4-benzodioxin-6-yl)ethyl]-$N^1$-(2-{[2-(4-hydroxy-2-oxo-2,3-dihydro-1,3-benzothiazol-7-yl)ethyl]amino}ethyl)-β-alaninamide;

$N^3$-[2-(3-chloro-4-hydroxyphenyl)ethyl]-$N^1$-cyclohexyl-$N^1$-(2-{[2-(4-hydroxy-2-oxo-2,3-dihydro-1,3-benzothiazol-7-yl)ethyl]amino}ethyl)-β-alaninamide;

$N^1$-Cyclooctyl-$N^1$-(2-{[2-(4-hydroxy-2-oxo-2,3-dihydro-1,3-benzothiazol-7-yl)ethyl]amino}ethyl)-$N^3$-[2-(3-hydroxyphenyl)ethyl]-β-alaninamide;

$N^1$-(4,4-Dimethylcyclohexyl)-$N^1$-(2-{[2-(4-hydroxy-2-oxo-2,3-dihydro-1,3-benzothiazol-7-yl)ethyl]amino}ethyl)-$N^3$-[2-(3-hydroxyphenyl)ethyl]-β-alaninamide;

N-Benzyl-4-[2-({3-[cycloheptyl(2-{[2-(4-hydroxy-2-oxo-2,3-dihydro-1,3-benzothiazol-7-yl)ethyl]amino}ethyl)amino]-3-oxopropyl}amino)ethyl]benzamide;

N-(2-{[2-(4-Hydroxy-2-oxo-2,3-dihydro-1,3-benzothiazol-7-yl)ethyl]amino}ethyl)-N-[(1R)-1'-methylpentyl]-$N^3$-(2-phenylethyl)-β-alaninamide;

N-(2-{[2-(4-Hydroxy-2-oxo-2,3-dihydro-1,3-benzothiazol-7-yl)ethyl]amino}ethyl)-N-[(1S)-1'-methylpentyl]-$N^3$-(2-phenylethyl)-β-alaninamide;

N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Cycloheptyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-Cycloheptyl-N-(2-{[2-(4-hydroxy-2-oxo-2,3-dihydro-1,3-benzothiazol-7-yl)ethyl]amino}ethyl)-$N^3$-(2-phenylethyl)-β-alaninamide;

N-Benzyl-4-[2-({3-[cycloheptyl(2-{[2-(4-hydroxy-2-oxo-2,3-dihydro-1,3-benzothiazol-7-yl)ethyl]amino}ethyl)amino]-3-oxopropyl}amino)ethyl]benzamide;

N-(2-{[2-(4-Hydroxy-2-oxo-2,3-dihydro-1,3-benzothiazol-7-yl)ethyl]amino}ethyl)-N-[(1R)-1-methylpentyl]-$N^3$-(2-phenylethyl)-β-alaninamide;

N-(2-{[2-(4-Hydroxy-2-oxo-2,3-dihydro-1,3-benzothiazol-7-yl)ethyl]amino}ethyl)-N-[(1S)-1-methylpentyl]-$N^3$-(2-phenylethyl)-β-alaninamide;

N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide;

N-Cycloheptyl-$N^3$-[2-(3-fluorophenyl)ethyl]-N-(2-{[2-(4-hydroxy-2-oxo-2,3-dihydro-1,3-benzothiazol-7-yl)ethyl]amino}propyl)-β-alaninamide; or, N-Cyclohexyl-N-(2-{[2-(4-hydroxy-2-oxo-2,3-dihydro-1,3-benzothiazol-7-yl)ethyl]amino}propyl)-$N^3$-(2-phenylethyl)-β-alaninamide;

or a pharmaceutically acceptable salt thereof.

The present invention further provides a process for the preparation of a compound of formula (I) or a pharmaceutically acceptable salt thereof as defined above. Examples of processes which can be used to prepare the compounds of the present invention are shown in Routes A, B, C and D shown below. In the Routes PG means Protecting Group (it is, for example, CBZ or benzyl), and examples are known in the art and described in the book 'Protective Groups in Organic Chemistry' (see below). Starting materials required in these Routes are either known in the art, or can be prepared by using or adapting literature methods or methods presented in the Examples below.

Compounds of formula (I) can be converted into further compounds of formula (I) using standard procedures.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups (for example by literature methods or by adapting techniques used in the Examples below).

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted by standard methods known in the art to a pharmaceutically acceptable salt thereof, for example an acid addition salt such as a hydrochloride (for example a dihydrochloride), hydrobromide (for example a dihydrobromide), trifluoroacetate (for example a di-trifluoroacetate), sulphate, phosphate, acetate, fumarate, maleate, tartrate, lactate, citrate, pyruvate, succinate, oxalate, methanesulphonate p-toluenesulphonate, bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, D-mandelate, L-mandelate, 2,5-dichlorobenzenesulphonate, cinnamate or benzoate. In one aspect of the invention a pharmaceutically acceptable salt is a hydrobromide (for example a dihydrobromide), acetate (for example a diacetate), D-mandelate (for example a di-D-mandelate) or benzoate (for example a dibenzoate).

The compounds of formula (I) and their pharmaceutically acceptable salts can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthropathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis (including ulcerative colitis, microscopic colitis and indeterminant colitis) proctitis, pruritis ani, coeliac disease, irritable bowel disorder, irritable bowel syndrome, non-inflammatory diarrhoea, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins; and, 14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating, or reducing the risk of, an inflammatory disease or condition (including a reversible obstructive airways disease or condition) which comprises administering to a patient in need thereof a therapeutically effective amount of a compound of formula (I) or a pharmaceutically acceptable salt thereof as hereinbefore defined.

In particular, the compounds of this invention may be used in the treatment of adult respiratory distress syndrome (ARDS), pulmonary emphysema, bronchitis, bronchiectasis, chronic obstructive pulmonary disease (COPD), asthma and rhinitis.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The invention therefore further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R) or T-Lymphocytes (CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenytoin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof. A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$- or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$. or $NK_3$. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2×7; (xxvii) inhibitor of transcription factor activation such as NFkB, API or STATS; or (xxviii) a glucocorticoid receptor (GR-receptor) agonist.

In a further aspect the present invention provides a combination (for example for the treatment of COPD, asthma or allergic rhinitis) of a compound of formula (I) and one or more agents selected from the list comprising:

a non-steroidal glucocorticoid receptor (GR-receptor) agonist;

a PDE4 inhibitor including an inhibitor of the isoform PDE4D;

a muscarinic receptor antagonist (for example a M1, M2 or M3 antagonist, such as a selective M3 antagonist) such as ipratropium bromide, tiotropium bromide, oxitropium bromide, pirenzepine or telenzepine;

a modulator of chemokine receptor function (such as a CCR1 receptor antagonist);

a steroid (such as budesonide); or, an inhibitor of a kinase function (for example IKK2 or p38).

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The present invention will now be further explained by reference to the following illustrative examples.

General Methods $^1$H NMR spectra were recorded on a Varian Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm), acetonitrile-d$_3$ ($\delta_H$ 1.95 ppm) or methanol-d$_4$ ($\delta_H$ 3.31 ppm) were used as internal references. Column chromatography was carried out using silica gel (0.040-0.063 mm, Merck). Unless stated otherwise, starting materials were commercially available. All solvents and commercial reagents were of laboratory grade and were used as received.

The following method was used for LC/MS analysis:

Instrument Agilent 1100; Column Waters Symmetry 2.1×30 mm; Mass APCI; Flow rate 0.7 ml/min; Wavelength 254 nm; Solvent A: water+0.1% TFA; Solvent B: acetonitrile+0.1% TFA; Gradient 15-95%/B 8 min, 95% B 1 min.

Analytical chromatography was run on a Symmetry C$_{18}$-column, 2.1×30 mm with 3.5 μm particle size, with acetonitrile/water/0.1% trifluoroacetic acid as mobile phase in a gradient from 5% to 95% acetonitrile over 8 minutes at a flow of 0.7 ml/min.

The abbreviations or terms used in the examples have the following meanings:
SCX: Solid phase extraction with a sulfonic acid sorbent
HPLC: High performance liquid chromatography
DMF: N,N-Dimethylformamide
THF: Tetrahydrofuran
NMP: N-Methylpyrrolidinone
HATU: O-(7-Azabenzotriazol-1-yl)-N,N,N',N'-tetramethyluronium hexafluorophosphate
TFA: Trifluoroacetic acid

EXAMPLE 1

N-(2-{[2-(4-Hydroxy-2-oxo-2,3-dihydro-1,3-benzothiazol-7-yl)ethyl]amino}ethyl)-N-isopropyl-N³-(2-phenylethyl)-β-alaninamide bis-trifluoroacetic acid salt

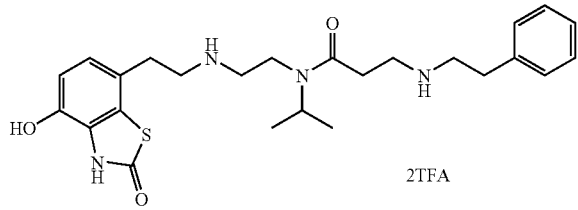

i) Benzyl (2,2-dimethoxyethyl)[2-(4-hydroxy-2-oxo-2,3-dihydro-1,3-benzothiazol-7-yl)ethyl]carbamate

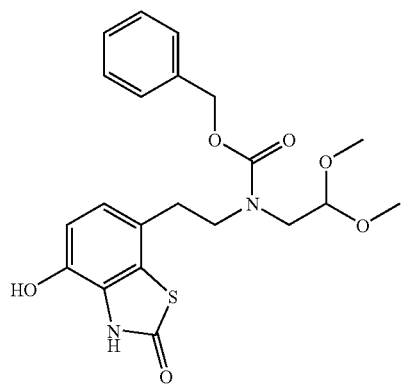

7-(2-Aminoethyl)-4-hydroxy-1,3-benzothiazol-2(3H)-one hydrobromide (20 g) was dissolved in a mixture of THF (300 ml) and water (150 ml). Sodium hydrogen carbonate (5.77 g) was added and the mixture stirred for 15 min. Acetic acid (7.86 ml) was added, followed by dimethoxyacetaldehyde (14.9 g, 12.91 ml) and the mixture stirred for a further 30 min. Sodium cyanoborohydride (8.64 g) was added portionwise over 10 min and the solution stirred for a further 20 h. Ethyl acetate (500 ml) and a solution of sodium hydrogen carbonate (17.33 g) in water (250 ml) were added, the mixture was stirred vigorously, benzyl chloroformate (8.78 g, 7.35 ml) was added, and the mixture stirred for 2 h. The organic layer was separated, washed with water, 0.1M aq. HCl, water and brine, dried (anhydrous $Na_2SO_4$), filtered and evaporated. The resulting material was purified by flash chromatography on silica using 10% methanol in dichloromethane as eluent to give the sub-title compound as a light brown gum (23.1 g).

$^1$H NMR $\delta_{(DMSO)}$ 11.60 (1H, s), 9.90 (1H, s), 7.39-7.12 (5H, m), 6.73 (2H, m), 5.05 (2H, m), 4.43 (0.5H, t), 4.35 (0.5H, t), 3.41 (2H, m), 3.33 (1.5H, s), 3.27 (3H, s), 3.22 (1.5H, s), 3.19 (2H, m), 2.69 (2H, q).

MS (APCI+) 433 [M+H]⁺ ii) Benzyl[2-(4-hydroxy-2-oxo-2,3-dihydro-1,3-benzothiazol-7-yl)ethyl](2-oxoethyl)carbamate

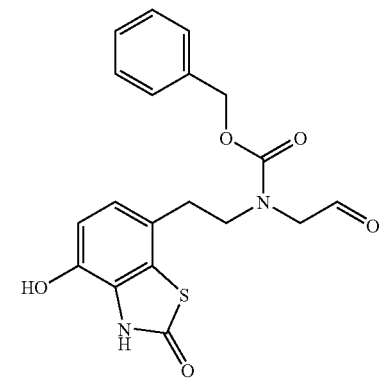

Example 1 step i) (5 g) was dissolved in acetone (100 ml), 2M HCl in dioxane (50 ml) was added and the mixture stirred for 3 h. Concentrated HCl (2 ml) was added and mixture stirred for a further 20 h. Toluene (100 ml) was added and the solvents removed in vacuo. The residue was dissolved in THF (200 ml), toluene (100 ml) added, and the solvents removed in vacuo (×2) to give the sub-title compound as an off white solid (4.5 g).

$^1$H NMR $\delta_{(DMSO)}$ 11.61 (1H, m), 9.91 (1H, m), 9.41 (1H, s), 7.31 (5H, m), 6.74 (2H, m), 5.01 (2H, m), 4.04 (2H, d), 3.46 (2H, t), 2.69 (2H, t).

MS (APCI+) 387 [M+H]⁺ iii) Benzyl [2-(4-hydroxy-2-oxo-2,3-dihydro-1,3-benzothiazol-7-yl)ethyl][2-(isopropylamino)ethyl]carbamate

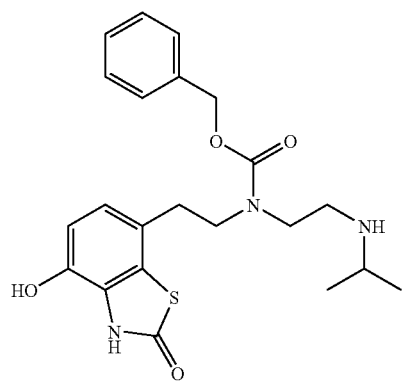

Example 1 step ii) (0.5 g) was added to a solution of iso-propylamine (0.23 g, 0.33 ml) in a mixture of THF (10 ml) and water (1 ml) and the mixture was stirred for 15 min. Sodium cyanoborohydride (0.17 g) was added, followed by acetic acid (0.24 g, 0.23 ml) and the reaction stirred for a further 2 h. The reaction was quenched with saturated aqueous sodium hydrogen carbonate, extracted with ethyl acetate, washed with brine, dried (anhydrous $Na_2SO_4$), filtered and evaporated to give the sub-title compound as a light brown gum (0.6 g).

¹H NMR δ$_{(DMSO)}$ 7.35 (5H, m), 6.74 (2H, m), 5.79 (1H, m), 5.05 (2H, m), 3.42 (2H, t), 3.29 (2H, m), 2.81 (2H, m), 2.70 (2H, m), 1.11 (6H, m).

MS (APCI+) 430 [M+H]$^+$ iv) N-[(Benzyloxy)carbonyl]-N-(2-phenylethyl)-β-alanine

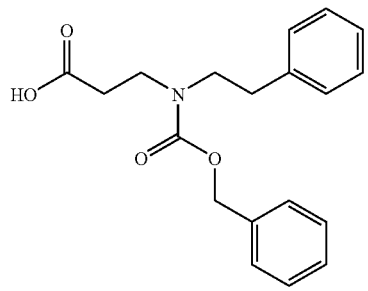

tert-Butyl acrylate (1.29 g, 1.47 ml) was dissolved in ethanol (10 ml) and this solution was added drop-wise to a solution of phenethylamine (1.1 g, 1.26 ml) in ethanol (25 ml), and the mixture stirred at room temperature overnight. The solvents were removed in vacuo. The residue was dissolved in dichloromethane (40 ml) and triethylamine (1.23 g, 1.69 ml) was added, followed by portion-wise addition of benzyl chloroformate (2.59 g, 2.17 ml), and the mixture was stirred at room temperature for 4 hours. The reaction was diluted with water, and the layers were separated. The organic phase was washed with saturated aqueous sodium hydrogen carbonate, water, citric acid (×2), dried (anhydrous MgSO$_4$), filtered and evaporated. The residue was dissolved in dichloromethane (25 ml), trifluoroacetic acid (25 ml) added, and the reaction was stirred at room temperature for 90 min. Toluene was added to the mixture and the solvents were removed in vacuo to give the sub-title compound as an oil (3.2 g).

¹H NMR δ (CDCl$_3$) 7.39-7.07 (10H, m), 5.16-5.08 (2H, m), 3.54-3.43 (4H, m), 2.89-2.78 (2H, m), 2.66-2.49 (2H, m).

MS (APCI−) 326 [M−H]$^+$ v) N-(2-{[2-(4-Hydroxy-2-oxo-2,3-dihydro-1,3-benzothiazol-7-yl)ethyl]amino}ethyl)-N-isopropyl-N$^3$-(2-phenylethyl)-β-alaninamide bis-trifluoroacetic acid salt

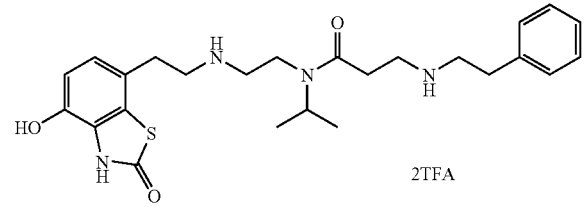

The amine as prepared in example 1 step iii) (0.3 g), the acid as prepared in example 1 step iv) (0.5 g) and N,N-diisopropylethylamine (0.545 g, 0.735 ml) were dissolved in NMP (5 ml), HATU (0.58 g) was added, and the mixture was stirred at room temperature for 20 h. The reaction was quenched with water, extracted with ethyl acetate, washed with water and brine, dried (anhydrous Na$_2$SO$_4$), filtered and evaporated. The residue was dissolved in methanol (5 ml), 1M NH$_3$/MeOH (10 ml) was added and the mixture was stirred for 30 min. Toluene (30 ml) was added and the solvents removed in vacuo. The residue was azeotroped with acetonitrile (30 ml) and toluene (30 ml). The residue was dissolved in acetic acid (5 ml), hydrogen bromide 30 wt % solution in acetic acid (5 ml) was added, and the mixture was stirred for 20 h. Toluene (30 ml) was added and the solvents removed in vacuo. The residue was azeotroped with acetonitrile (30 ml) and toluene (30 ml), then purified by reverse phase HPLC (5-50% acetonitrile in aqueous TFA) to give the title compound as a white solid (60 mg).

¹H NMR δ$_{(DMSO)}$ 11.73 (1H, s), 10.20 (1H, s), 8.74 (4H, m), 7.31 (5H, m), 6.86 (1H, d), 6.76 (1H, d), 4.05 (1H, m), 3.48 (2H, m), 3.19 (6H, m), 3.04 (2H, m), 2.93 (2H, m), 2.82 (2H, m), 2.74 (2H, m), 1.20 (3H, d), 1.16 (3H, d).

MS (Multimode+) 471 [(M-salt)+H]$^+$

EXAMPLE 2

N-Cyclopentyl-N-(2-{[2-(4-hydroxy-2-oxo-2,3-dihydro-1,3-benzothiazol-7-yl)ethyl]amino}ethyl)-N$^3$-(2-phenylethyl)-β-alaninamide bis-trifluoroacetic acid salt

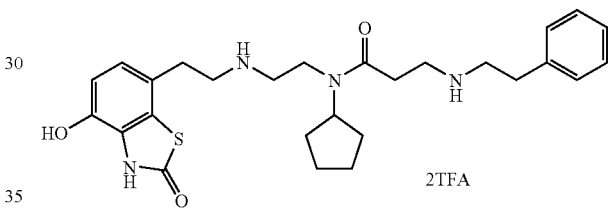

The title compound was prepared by the method of example 1 using cyclopentylamine in step iii).

¹H NMR δ$_{(DMSO)}$ 11.73 (1H, s), 10.20 (1H, s), 8.68 (4H, m), 7.30 (5H, m), 6.86 (1H, d), 6.76 (1H, d), 4.10 (1H, m), 3.45 (2H, m), 3.19 (6H, m), 3.04 (2H, m), 2.93 (2H, m), 2.81 (4H, m), 1.83 (2H, m), 1.67 (2H, m), 1.50 (4H, m).

MS (Multimode+) 497 [(M-salt)+H]$^+$

EXAMPLE 3

N$^3$-[2-(4-Chlorophenyl)ethyl]-N-(2-{[2-(4-hydroxy-2-oxo-2,3-dihydro-1,3-benzothiazol-7-yl)ethyl]amino}ethyl)-N-isopropyl-β-alaninamide bis-trifluoroacetic acid salt

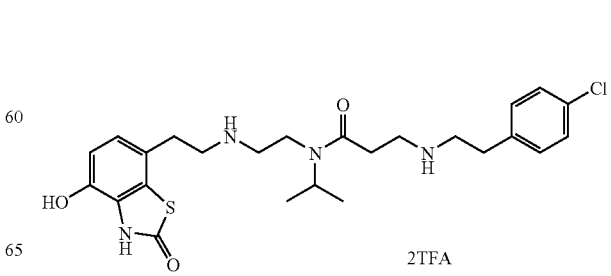

i) N-[(Benzyloxy)carbonyl]-N-[2-(4-chlorophenyl) ethyl]-β-alanine

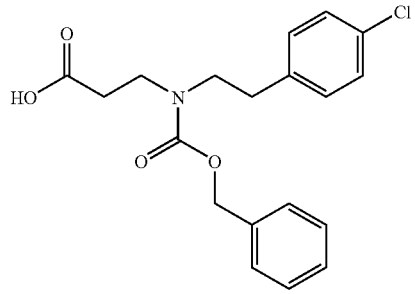

The 4-chlorophenethylamine (3.11 g) was dissolved in ethanol (25 ml) and tert-butyl acrylate (2.56 g) was added, and the mixture was stirred at room temperature overnight. The solvents were removed in vacuo. The residue was dissolved in ethyl acetate (30 ml), and Hunig's base (5.17 g, 6.97 ml) was added. The mixture was cooled in an ice/water bath, treated with benzyl chloroformate (4.26 g, 3.52 ml) and allowed to warm to room temperature over 4 h. The reaction was diluted with more ethyl acetate and washed thoroughly with dil. HCl then water, dried (anhydrous MgSO$_4$), filtered and evaporated. The residue was purified by flash chromatography on silica using isohexane:ethyl acetate (6:1) as eluent. The resulting material was dissolved in dichloromethane (30 ml), trifluoroacetic acid (25 ml) was added, and the reaction was stirred at room temperature for 2 h. Toluene was added to the mixture and the solvents were removed in vacuo. The residue was azeotroped with toluene to give the sub-title compound as a white solid (5.5 g).

$^1$H NMR $\delta_{(CDCL3)}$ 8.96 (1H, s), 7.52-6.93 (9H, m), 5.11 (2H, d), 3.61-3.36 (4H, m), 2.94-2.70 (2H, m), 2.60 (2H, d).

MS (Multimode+) 362 [M+H]$^+$ ii) N$^3$-[2-(4-Chlorophenyl)ethyl]-N-(2-{[2-(4-hydroxy-2-oxo-2,3-dihydro-1,3-benzothiazol-7-yl) ethyl]amino}ethyl)-N-isopropyl-β-alaninamide bis-trifluoroacetic acid salt

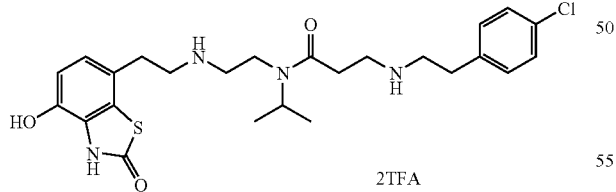

The acid as prepared in Example 3 step i) (0.2 g), the amine as prepared in example 1 step iii) (0.215 g), and N,N-diisopropylethylamine (0.193 g, 0.26 ml) were dissolved in NMP (5 ml), HATU (0.21 g) was added, and the mixture was stirred at 50° C. for 20 h. The reaction was cooled to room temperature, and treated with 10% aqueous ammonia (20 ml) for 10 min. The reaction mixture was acidified with 2M HCl, extracted with ethyl acetate, washed with water (×2) and brine, dried (anhydrous Na$_2$SO$_4$), filtered and evaporated. The residue was dissolved in acetic acid (3 ml), hydrogen bromide 30 wt % solution in acetic acid (2 ml) was added, and the mixture was stirred for a further 2 h. Toluene (30 ml) was added and the solvents removed in vacuo. The residue was azeotroped with acetonitrile (30 ml) and toluene (30 ml), then purified by reverse phase HPLC (5-50% acetonitrile in aqueous TFA) to give the title compound as a white solid (115 mg).

$^1$H NMR $\delta_{(DMSO)}$ 10.21 (1H, s), 7.40 (2H, m), 7.30 (2H, m), 6.86 (1H, d), 6.75 (1H, d), 4.03 (1H, m), 3.51-3.10 (10H, m), 3.04 (2H, m), 2.94 (2H, m), 2.81 (2H, m), 1.13 (6H, m).

MS (Multimode+) 505 [(M-salt)+H]$^+$

EXAMPLE 4

N-(4,4-Difluorocyclohexyl)-N-(2-{[2-(4-hydroxy-2-oxo-2,3-dihydro-1,3-benzothiazol-7-yl)ethyl] amino}ethyl)-N$^3$-(2-phenylethyl)-β-alaninamide bis-trifluoroacetic acid salt

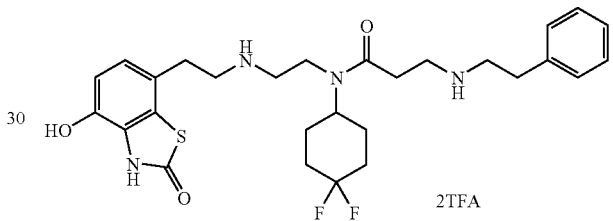

i) Benzyl {2-[(4,4-difluorocyclohexyl)amino]ethyl} [2-(4-hydroxy-2-oxo-2,3-dihydro-1,3-benzothiazol-7-yl)ethyl]carbamate

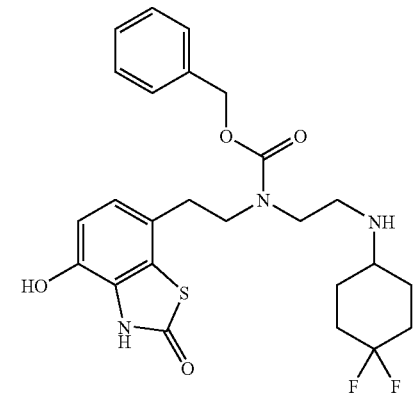

The sub-title compound was prepared by the method of Example 1 step iii) using 4,4-difluorocyclohexylamine.

$^1$H NMR $\delta_{(DMSO)}$ 7.41-7.25 (5H, m), 6.72 (2H, m), 5.04 (2H, m), 3.47-3.13 (5H, m), 2.75-2.51 (4H, m), 2.08-1.60 (6H, m), 1.48-1.22 (2H, m).

MS (APCI+) 506 [M+H]$^+$ ii) N-(4,4-Difluorocyclohexyl)-N-(2-{[2-(4-hydroxy-2-oxo-2,3-dihydro-1,3-benzothiazol-7-yl)ethyl]amino}ethyl)-N³-(2-phenylethyl)-β-alaninamide bis-trifluoroacetic acid salt

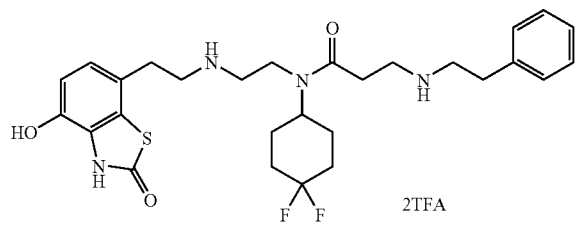

The title compound was prepared by the method of Example 3 using the amine as prepared in example 4 step i) and the acid as prepared in example 1 step iv).

¹H NMR δ$_{(DMSO)}$ 10.21 (1H, s), 8.70 (4H, m), 7.34 (2H, m), 7.26 (3H, m), 6.86 (1H, m), 6.76 (1H, m), 3.87 (1H, m), 3.45 (2H, m), 3.35 (4H, m), 3.21 (4H, m), 3.13 (2H, m), 3.01 (2H, m), 2.95 (2H, m), 2.87 (2H, m), 2.81 (2H, m), 2.09 (2H, m), 1.76 (2H, m).

MS (Multimode+) 547 [(M-salt)+H]⁺

EXAMPLE 5

N-Cyclohexyl-N-(2-{[2-(4-hydroxy-2-oxo-2,3-dihydro-1,3-benzothiazol-7-yl)ethyl]amino}ethyl)-N³-(2-phenylethyl)-β-alaninamide bis-trifluoroacetic acid salt

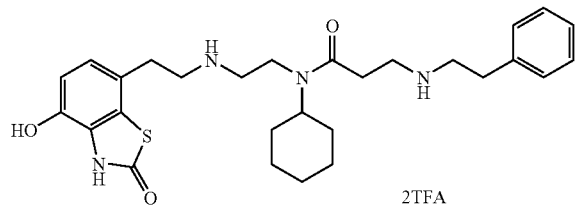

i) Benzyl [2-(cyclohexylamino)ethyl][2-(4-hydroxy-2-oxo-2,3-dihydro-1,3-benzothiazol-7-yl)ethyl]carbamate

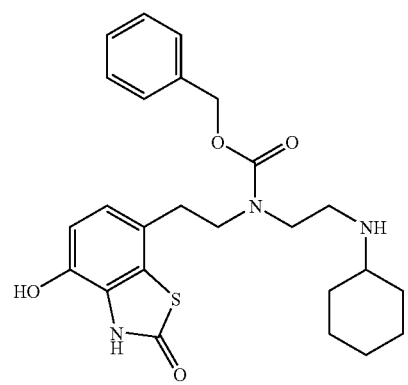

The sub-title compound was prepared by the method of Example 1 step iii) using cyclohexylamine.

¹H NMR 90° C. δ$_{(DMSO)}$ 7.40-7.50 (m, 5H), 6.86 (d, 1H), 6.80 (d, 1H), 5.18 (s, 2H), 3.72 (t, 2H), 3.56 (t, 2H), 2.94 (t, 2H), 2.83 (t, 2H), 1.96 (m, 2H), 1.84 (m, 4H), 1.68 (m, 1H), 1.29 (m, 4H).

MS (APCI+) 470 [M+H]⁺ ii) Benzyl (3-chloro-3-oxopropyl)(2-phenylethyl)carbamate

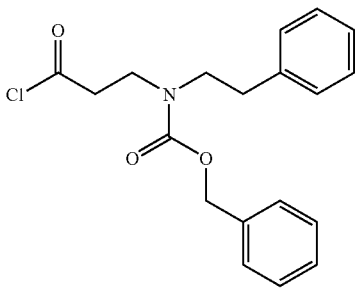

The acid as prepared in example 1 step iv) (654 mg) was dissolved in dichloromethane (4 ml) and oxalyl chloride (0.18 g, 0.26 ml) was added, followed by 2 drops of DMF, which caused effervescence. The mixture was stirred until the effervescence ceased, then all solvents were thoroughly removed by evaporation to give the sub-title compound. The residue was dissolved in dichloromethane to make up a 0.5M solution, and the material was stored as the solution.

iii) N-Cyclohexyl-N-(2-{[2-(4-hydroxy-2-oxo-2,3-dihydro-1,3-benzothiazol-7-yl)ethyl]amino}ethyl)-N³-(2-phenylethyl)-β-alaninamide bis-trifluoroacetic acid salt

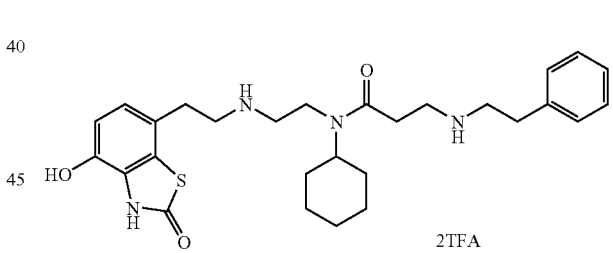

The amine as prepared in example 5 step i) (0.15 g) was dissolved in DMF (1 ml) and triethylamine (94 mg, 0.13 ml) was added, followed by a drop-wise addition of a 0.5M solution of the acid chloride in dichloromethane as prepared in example 5 step ii) (1.3 ml), and the mixture was stirred for 1 h. The reaction mixture was partitioned between water and dichloromethane. The organic extracts were combined, concentrated, washed with water, dried (anhydrous Na₂SO₄), filtered and evaporated. The residue was dissolved in dichloromethane (2.5 ml), hydrogen bromide 30 wt % solution in acetic acid (2.5 ml) was added, and the mixture was stirred for a further 40 h. Toluene (5 ml) was added and the solvents removed in vacuo. The residue was azeotroped with toluene (×3), then purified by reverse phase HPLC (5-50% acetonitrile in aqueous TFA) to give the title compound as a white solid (60 mg).

¹H NMR δ$_{(DMSO)}$ 11.73 (1H, s), 10.17 (1H, s), 8.99-8.51 (4H, m), 7.36-7.24 (5H, m), 6.86 (1H, d), 6.76 (1H, d), 3.53-

3.41 (2H, m), 3.27-3.08 (7H, m), 3.05-2.90 (4H, m), 2.87-2.77 (4H, m), 1.83-1.20 (9H, m), 1.16-1.00 (1H, m).

MS (Multimode+) 511 [(M-salt)+H]⁺

EXAMPLE 6

N-(2,2-Dimethylpropyl)-N-(2-{[2-(4-hydroxy-2-oxo-2,3-dihydro-1,3-benzothiazol-7-yl)ethyl]amino}ethyl)-N³-(2-phenylethyl)-β-alaninamide bis-trifluoroacetic acid salt

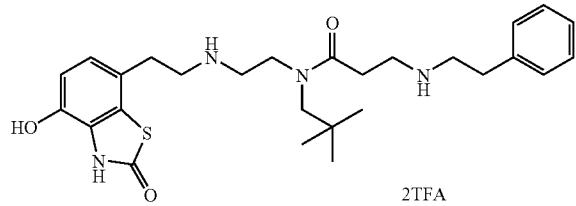

i) Benzyl {2-(tert-butoxycarbonylamino)ethyl}[2-(4-hydroxy-2-oxo-2,3-dihydro-1,3-benzothiazol-7-yl)ethyl]carbamate

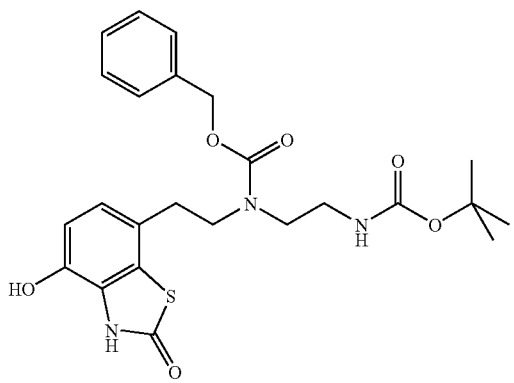

7-(2-Aminoethyl)-4-hydroxy-1,3-benzothiazol-2(3H)-one hydrobromide (3.66 g) was suspended in a mixture of THF (50 ml) and water (25 ml). Sodium hydrogen carbonate (1.06 g) was added and the mixture stirred for 15 min. Acetic acid (1.44 ml) was added, followed by a solution of tert-butyl (2-oxoethyl)carbamate (2.0 g) in THF (10 ml), and the mixture stirred for a further 30 min. Sodium cyanoborohydride (1.58 g) was added and the solution stirred for a further 18 h. Ethyl acetate (100 ml) and a solution of sodium hydrogen carbonate (3.17 g) in water (50 ml) were added, the mixture was stirred vigorously, benzyl chloroformate (709 ul) was added, and the mixture stirred for 15 min. A second portion of benzyl chloroformate (170 ul) was added and the mixture stirred for a further 30 min. The reaction mixture was extracted with ethyl acetate (×2) and filtered through celite. The organic extracts were combined, washed with water, dried (anhydrous Na₂SO₄), filtered and evaporated. The resulting material was purified by flash chromatography on silica using isohexane:ethyl acetate (50:50, 25:75, 100%) as eluent to give the sub-title compound (2.94 g).

MS (APCI+) 388 [(M-BOC)+H]⁺ ii) Benzyl (2-aminoethyl)[2-(4-hydroxy-2-oxo-2,3-dihydro-1,3-benzothiazol-7-yl)ethyl]carbamate

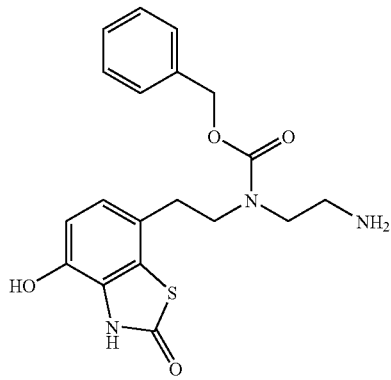

Example 6 step i) (5.54 g) was dissolved in methanol (125 ml), 4M HCl in dioxane (30 ml) was added, and the mixture was stirred at room temperature for 18 h. The solvents were removed in vacuo and the residue was partitioned between 2M aqueous HCl and ethyl acetate. The aqueous phase was washed with further ethyl acetate before being basified with sodium hydrogen carbonate, then extracted with ethyl acetate (×3). The organic extracts were combined, washed with water, dried (anhydrous Na₂SO₄), filtered and evaporated to give the sub-title compound (1.07 g).

MS (APCI+) 388 [M+H]⁺ iii) Benzyl {2-[(2,2-dimethylpropyl)amino]ethyl}[2-(4-hydroxy-2-oxo-2,3-dihydro-1,3-benzothiazol-7-yl)ethyl]carbamate

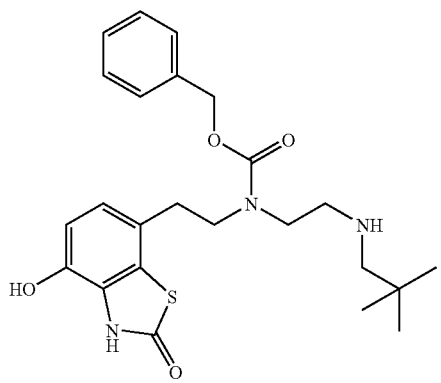

Example 6 step ii) (100 mg) was added to a solution of pivalaldehyde (22 mg) in a mixture of THF (5 ml) and water (3 ml), and the mixture was stirred for 1 h. Sodium cyanoborohydride (16 mg) and acetic acid (15 ul) were added and the reaction stirred for a further 18 h. The reaction was quenched with saturated aqueous NaHCO₃, and extracted with ethyl acetate (×3). The organic extracts were combined, washed with water, dried (anhydrous Na₂SO₄), filtered and evaporated. The residue was purified by flash chromatography on silica using 5%, then 10% methanol in dichloromethane as eluent to give the sub-title compound (77 mg).
MS (APCI+) 458 [M+H]⁺ iv) N-(2,2-Dimethylpropyl)-N-(2-{[2-(4-hydroxy-2-oxo-2,3-dihydro-1,3-benzothiazol-7-yl)ethyl]amino}ethyl)-N³-(2-phenylethyl)-β-alaninamide bis-trifluoroacetic acid salt

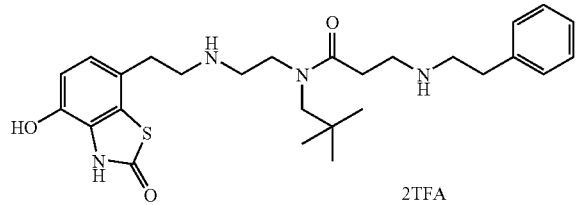

Example 6 step iii) (77 mg) was dissolved in dichloromethane (10 ml), chlorotrimethylsilane (85 ul) was added, followed by triethylamine (94 ul), and the mixture was stirred at room temperature for 1 h. A solution of the acid chloride as prepared in example 5 step ii) (69 mg) in dichloromethane (337 ul) was added and the mixture was stirred for a further 1 h. The solvents were removed in vacuo, the residue was redissolved in dichloromethane (1 ml), hydrogen bromide 30 wt % solution in acetic acid (1 ml) was added, and the mixture was stirred for 3 h. Toluene was added to the reaction and all solvents were removed in vacuo. The residue was azeotroped with toluene (×2), then acetonitrile (×2) before being purified by reverse phase HPLC (15-60% acetonitrile in aqueous TFA) to give the title compound (47 mg).
¹H NMR δ$_{(DMSO)}$ 11.77-11.71 (1H, m), 10.17-10.13 (1H, m), 8.87-8.78 (1H, m), 8.69-8.49 (3H, m), 7.37-7.31 (2H, m), 7.29-7.23 (3H, m), 6.88-6.84 (1H, m), 6.78-6.74 (1H, m), 3.60 (2H, t), 3.25-3.07 (10H, m), 2.93 (2H, t), 2.86-2.76 (4H, m), 0.97-0.87 (9H, m).
MS (Multimode+) 499 [(M-salt)+H]⁺

EXAMPLE 7

N³-[2-(3-Chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide bis-trifluoroacetic acid salt

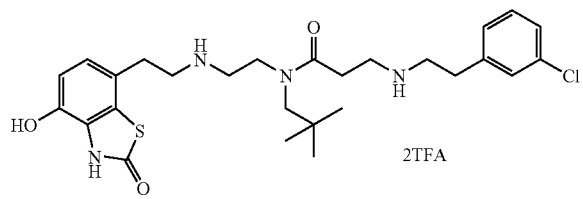

i) Benzyl {2-[acryloyl(2,2-dimethylpropyl)amino]ethyl}[2-(4-hydroxy-2-oxo-2,3-dihydro-1,3-benzothiazol-7-yl)ethyl]carbamate

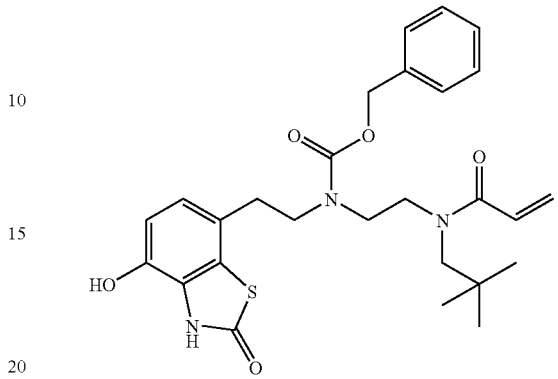

The amine as prepared in Example 6 step iii) (1.57 g) was dissolved in dichloromethane (20 ml), chlorotrimethylsilane (1.29 ml) and triethylamine (1.91 ml) were added, and the mixture was stirred at room temperature for 1 h. The mixture was cooled to 0° C., acryloyl chloride (336 ul) added, and the mixture was stirred, warming to room temperature, for 3 h. The reaction mixture was diluted with dichloromethane, washed with saturated sodium hydrogen carbonate, then with water, dried (anhydrous Na₂SO₄), filtered and evaporated. The residue was purified by flash chromatography on silica using ethyl acetate (30, 50, 70, 100%) in isohexane as eluent to give the sub-title compound (1.1 g).
¹H NMR 90° C. δ$_{(DMSO)}$ 7.39-7.28 (5H, m), 6.76-6.57 (3H, m), 6.04 (1H, d), 5.56-5.47 (1H, m), 5.05 (2H, s), 3.48-3.34 (4H, m), 3.26-3.09 (4H, m), 2.70 (2H, t), 0.83 (9H, s).
MS (APCI+) 512 [M+H]⁺ ii) N³-[2-(3-Chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide bis-trifluoroacetic acid salt

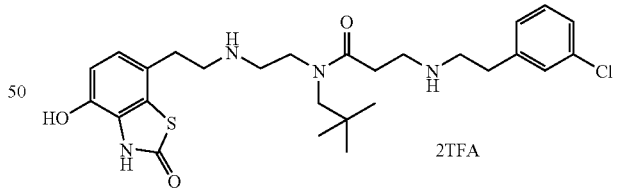

Example 7 step i) (110 mg) was dissolved in ethanol (1.5 ml), 3-chlorophenethylamine (101 mg, 90 ul) was added and the mixture was stirred at 50° C. for 18 h. The solvents were removed in vacuo and the residue was re-dissolved in dichloromethane (0.5 ml). This solution was cooled in an ice/water bath, hydrogen bromide 30 wt % solution in acetic acid (0.5 ml) was added, and the mixture was stirred at room temperature for 2 h. Toluene (1 ml) was added to the reaction and all solvents were removed in vacuo. The residue was azeotroped with toluene, then ethanol (×2) before being purified by reverse phase HPLC (5-45% acetonitrile in aqueous TFA) to give the title compound (62 mg).

$^1$H NMR δ$_{(DMSO)}$ 11.76-11.72 (1H, m), 10.16-10.12 (1H, m), 8.84-8.76 (1H, m), 8.68-8.48 (3H, m), 7.40-7.31 (3H, m), 7.27-7.22 (1H, m), 6.88-6.83 (1H, m), 6.77-6.73 (1H, m), 3.59 (2H, t), 3.28-3.07 (10H, m), 2.95 (2H, t), 2.87-2.75 (4H, m), 0.98-0.87 (9H, m).

MS (Multimode+) 533 [(M-salt)+H]$^+$

EXAMPLE 8

N$^3$-[2-(4-Chlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide bis-trifluoroacetic acid salt

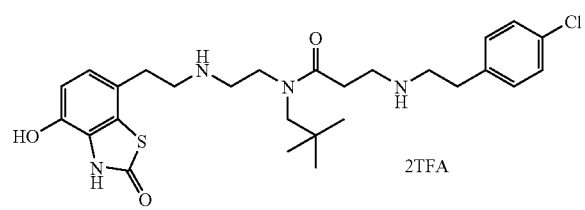

The title compound was prepared by the method of Example 7 using 4-chlorophenethylamine in step ii).

$^1$H NMR δ$_{(DMSO)}$ 11.74 (1H, s), 10.16-10.11 (1H, m), 8.79 (1H, s), 8.67-8.44 (3H, m), 7.43-7.37 (2H, m), 7.33-7.27 (2H, m), 6.87-6.83 (1H, m), 6.77-6.73 (1H, m), 3.63-3.56 (2H, m), 3.25-3.06 (10H, m), 2.96-2.89 (2H, m), 2.86-2.74 (4H, m), 0.97-0.87 (9H, m).

MS (Multimode+) 533 [(M-salt)+H]$^+$

EXAMPLE 9

N$^3$-[2-(3,4-Dichlorophenyl)ethyl]-N-(2,2-dimethylpropyl)-N-(2-{[2-(4-hydroxy-2-oxo-2,3-dihydro-1,3-benzothiazol-7-yl)ethyl]amino}ethyl)-β-alaninamide bis-trifluoroacetic acid salt

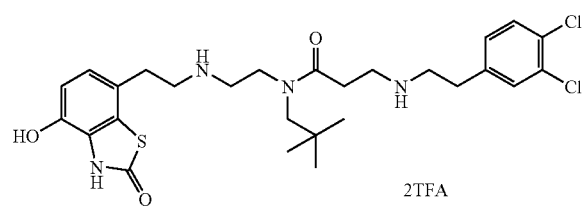

The title compound was prepared by the method of Example 7 using 3,4-dichlorophenethylamine in step ii).

$^1$H NMR δ$_{(DMSO)}$ 11.73 (1H, s), 10.17-10.13 (1H, m), 8.86 (1H, s), 8.72-8.49 (3H, m), 7.63-7.57 (2H, m), 7.31-7.26 (1H, m), 6.86 (1H, dd), 6.76 (1H, dd), 3.59 (2H, t), 3.28-3.07 (10H, m), 2.95 (2H, t), 2.86-2.75 (4H, m), 0.97-0.87 (9H, m).

MS (Multimode+) 567 [(M-salt)+H]$^+$

EXAMPLE 10

N-(2,2-Dimethylpropyl)-N-(2-{[2-(4-hydroxy-2-oxo-2,3-dihydro-1,3-benzothiazol-7-yl)ethyl]amino}ethyl)-N$^3$-[2-(3-methylphenyl)ethyl]-β-alaninamide bis-trifluoroacetic acid salt

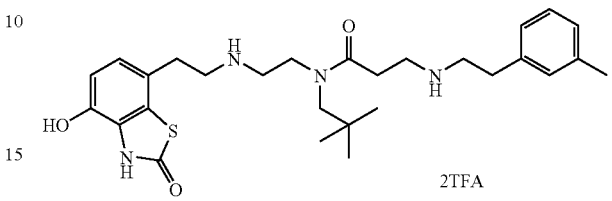

The title compound was prepared by the method of Example 7 using 3-methylphenethylamine in step ii).

$^1$H NMR δ$_{(DMSO)}$ 11.75 (1H, s), 10.16-10.12 (1H, m), 8.80 (1H, s), 8.68-8.44 (3H, m), 7.25-7.19 (1H, m), 7.09-7.02 (3H, m), 6.86 (1H, dd), 6.75 (1H, dd), 3.62-3.57 (2H, m), 3.23-3.07 (10H, m), 2.92-2.75 (6H, m), 2.29 (3H, s), 0.97-0.87 (9H, m).

MS (Multimode+) 513.2 [(M-salt)+H]$^+$

EXAMPLE 11

N-(2,2-Dimethylpropyl)-N-(2-{[2-(4-hydroxy-2-oxo-2,3-dihydro-1,3-benzothiazol-7-yl)ethyl]amino}ethyl)-N$^3$-[(2S)-2-phenylpropyl]-β-alaninamide bis-trifluoroacetic acid salt

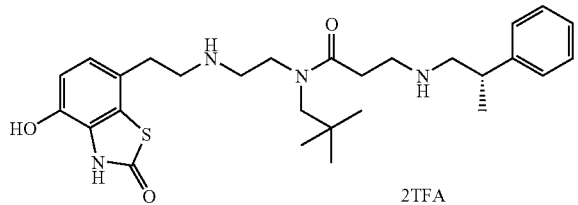

The title compound was prepared by the method of Example 7 using (2S)-2-phenylpropylamine in step ii).

$^1$H NMR δ$_{(DMSO)}$ 11.74 (1H, s), 10.16-10.12 (1H, m), 8.80 (1H, s), 8.67-8.18 (3H, m), 7.39-7.24 (5H, m), 6.85 (1H, d), 6.76 (1H, dd), 3.57 (2H, t), 3.24-3.05 (11H, m), 2.85-2.73 (4H, m), 1.29-1.24 (3H, m), 0.96-0.85 (9H, m).

MS (Multimode+) 513.2 [(M-salt)+H]$^+$

EXAMPLE 12

N$^3$-[2-(3-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide bis-trifluoroacetic acid salt

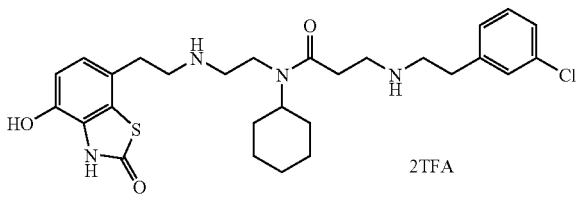

i) Benzyl {2-[acryloyl(cyclohexyl)amino]ethyl}[2-(4-hydroxy-2-oxo-2,3-dihydro-1,3-benzothiazol-7-yl)ethyl]carbamate

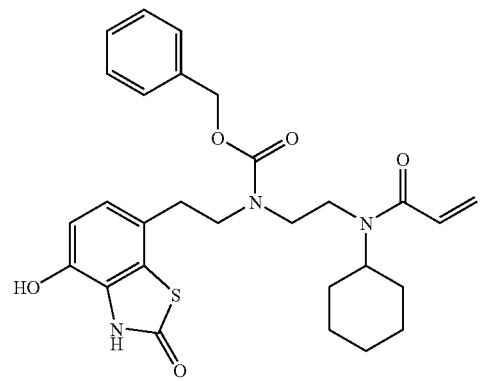

The amine as prepared in example 5 step i) was reacted with acryolyl chloride using the method of example 7 step i) to give the sub-title compound.
MS (APCI+) 524 [M+H]+ ii) $N^3$-[2-(3-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide bis-trifluoroacetic acid salt

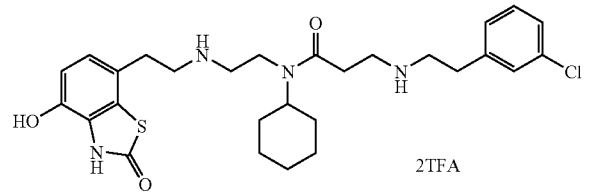

The acrylamide as prepared in example 12 step i) (150 mg) was dissolved in ethanol (1 ml), 3-chlorophenethylamine (90 mg, 80 ul) was added, and the mixture stirred at room temperature over the weekend. The solvents were removed in vacuo, the residue was redissolved in dichloromethane (0.5 ml), hydrogen bromide 30 wt % solution in acetic acid (0.5 ml) was added, and the mixture was stirred at room temperature for 2 h. Toluene (1 ml) was added to the reaction and all solvents were removed in vacuo. The residue was azeotroped with toluene, then ethanol (×2) before being purified by reverse phase HPLC (5-40% acetonitrile in aqueous TFA) to give the title compound (75 mg).
$^1$H NMR $\delta_{(DMSO)}$ 11.75 (1H, s), 10.14 (1H, s), 8.71-8.47 (4H, m), 7.40-7.31 (3H, m), 7.28-7.22 (1H, m), 6.88-6.84 (1H, m), 6.78-6.73 (1H, m), 3.58-3.44 (3H, m), 3.30-3.10 (6H, m), 3.04-2.91 (4H, m), 2.86-2.76 (4H, m), 1.82-1.22 (10H, m).
MS (Multimode+) 545 [(M-salt)+H]+

EXAMPLE 13

$N^3$-[2-(4-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide bis-trifluoroacetic acid salt

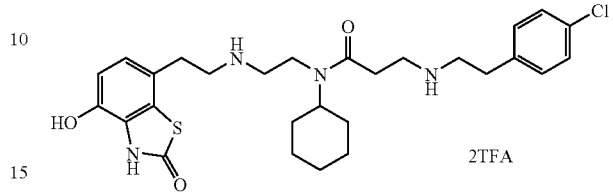

The title compound was prepared by the method of Example 12 using 4-chlorophenethylamine in step ii).
$^1$H NMR $\delta_{(DMSO)}$ 11.73 (1H, s), 10.13 (1H, s), 8.87-8.43 (4H, m), 7.41 (2H, d), 7.31 (2H, d), 6.86 (1H, d), 6.75 (1H, d), 3.53-3.41 (2H, m), 3.27-3.10 (7H, m), 3.04-2.89 (4H, m), 2.85-2.75 (4H, m), 1.81-1.22 (10H, m).
MS (Multimode+) 545 [(M-salt)+H]+

EXAMPLE 14

N-Cyclohexyl-N-(2-{[2-(4-hydroxy-2-oxo-2,3-dihydro-1,3-benzothiazol-7-yl)ethyl]amino}ethyl)-$N^3$-[2-(3-methylphenyl)ethyl]-β-alaninamide bis-trifluoroacetic acid salt

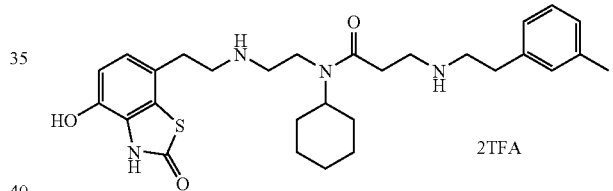

The acrylamide as prepared in Example 12 step i) was reacted with 3-methylphenethylamine using the method of example 7 step ii). The reaction mixture was purified using an SCX cartridge prior to the hydrogen bromide deprotection, to give the title compound.
$^1$H NMR $\delta_{(DMSO)}$ 11.73 (1H, s), 10.16 (1H, s), 8.95-8.49 (4H, m), 7.28-7.19 (1H, m), 7.10-7.02 (3H, m), 6.86 (1H, d), 6.75 (1H, d), 3.52-3.45 (4H, m), 3.25-3.10 (6H, m), 3.05-2.96 (1H, m), 2.93-2.76 (6H, m), 2.29 (3H, s), 1.82-1.02 (10H, m).
MS (Multimode+) 525 [(M-salt)+H]+

EXAMPLE 15

N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide bis-trifluoroacetic acid salt

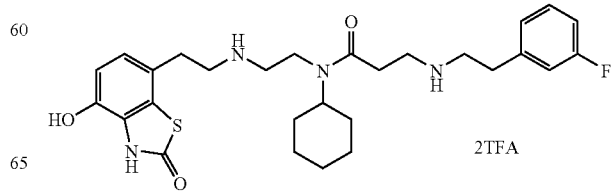

The title compound was prepared by the method of Example 14 using 3-fluorophenethylamine.

The acrylamide as prepared in Example 12 step i) (1 ml of a 0.33M solution in ethanol) was treated with 3-fluorophenethylamine (97 ul) and the mixture was stirred at 50° C. for 18 h. The product was purified by SCX chromatography eluting with 1N ammonia in methanol. The solvents were removed in vacuo and the residue was re-dissolved in dichloromethane (0.5 ml). This solution was cooled in an ice/water bath, hydrogen bromide 30 wt % solution in acetic acid (0.5 ml) was added, and the mixture was stirred at room temperature for 2 h. Toluene (1 ml) was added to the reaction and all solvents were removed in vacuo. The residue was azeotroped with toluene, then ethanol (×2) before being purified by reverse phase HPLC (5-40% acetonitrile in aqueous TFA). The residue was triturated with diethyl ether to give the title compound as a white solid (30 mg).

$^1$H NMR $\delta_{(DMSO)}$ 11.73 (1H, s), 10.13 (1H, s), 8.84-8.48 (4H, m), 7.43-7.34 (1H, m), 7.18-7.08 (3H, m), 6.86 (1H, d), 6.75 (1H, d), 3.59-3.45 (4H, m), 3.30-3.10 (5H, m), 3.03-2.93 (4H, m), 2.85-2.77 (4H, m), 1.81-1.03 (10H, m).

MS (Multimode+) 529 [(M-salt)+H]$^+$

EXAMPLE 16

N-Cyclohexyl-N$^3$-[2-(4-fluorophenyl)ethyl]-N-(2-{[2-(4-hydroxy-2-oxo-2,3-dihydro-1,3-benzothiazol-7-yl)ethyl]amino}ethyl)-β-alaninamide bis-trifluoroacetic acid salt

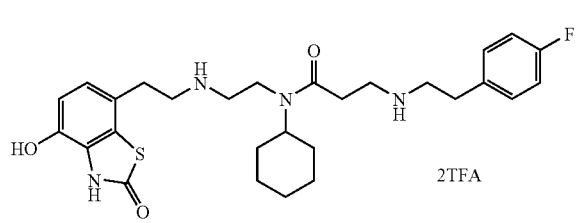

The title compound was prepared by the method of Example 14 using 4-fluorophenethylamine.

$^1$H NMR $\delta_{(DMSO)}$ 11.73 (1H, s), 10.15 (1H, s), 8.93-8.45 (4H, m), 7.35-7.14 (4H, m), 6.86 (1H, d), 6.75 (1H, d), 3.58-3.44 (4H, m), 3.26-3.11 (5H, m), 3.04-2.89 (4H, m), 2.86-2.77 (4H, m), 1.82-1.03 (10H, m).

MS (Multimode+) 529 [(M-salt)+H]$^+$

EXAMPLE 17

N$^3$-[2-(2-Chlorophenyl)ethyl]-N-cyclohexyl-N-(2-{[2-(4-hydroxy-2-oxo-2,3-dihydro-1,3-benzothiazol-7-yl)ethyl]amino}ethyl)-β-alaninamide bis-trifluoroacetic salt

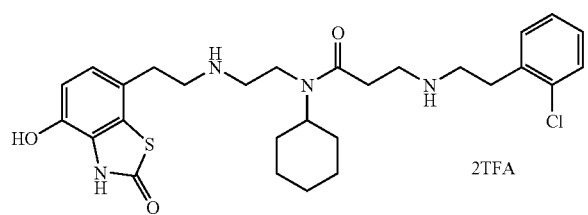

The title compound was prepared by the method of Example 14 using 2-chlorophenethylamine.

$^1$H NMR $\delta_{(DMSO)}$ 11.73 (1H, s), 10.15 (1H, s), 8.90-8.60 (4H, m), 7.47 (1H, dd), 7.42-7.39 (1H, m), 7.37-7.29 (2H, m), 6.86 (1H, d), 6.75 (1H, d), 3.60-3.44 (4H, m), 3.27-2.96 (9H, m), 2.88-2.76 (4H, m), 1.82-1.03 (10H, m).

MS (Multimode+) 545 [(M-salt)+H]$^+$

EXAMPLE 18

N-Cyclohexyl-N-(2-{[2-(4-hydroxy-2-oxo-2,3-dihydro-1,3-benzothiazol-7-yl)ethyl]amino}ethyl)-N$^3$-[(2S)-2-phenylpropyl]-β-alaninamide bis-trifluoroacetic acid salt

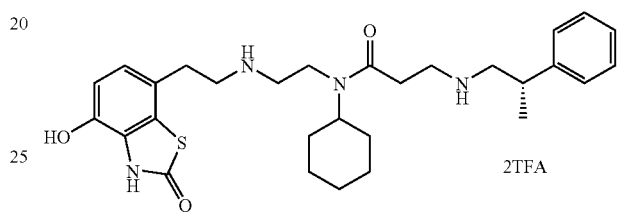

The title compound was prepared by the method of Example 14 using (2S)-2-phenylpropylamine.

$^1$H NMR $\delta_{(DMSO)}$ 11.73 (1H, s), 10.15 (1H, s), 8.61-8.19 (4H, m), 7.39-7.23 (5H, m), 6.85 (1H, d), 6.75 (1H, d), 3.46 (4H, m), 3.26-3.09 (6H, m), 2.98 (2H, m), 2.83-2.76 (4H, m), 1.82-1.04 (10H, m), 1.28 (3H, d).

MS (Multimode+) 525 [(M-salt)+H]$^+$

EXAMPLE 19

N-Cyclohexyl-N$^3$-(1,1-dimethyl-2-phenylethyl)-N-(2-{[2-(4-hydroxy-2-oxo-2,3-dihydro-1,3-benzothiazol-7-yl)ethyl]amino}ethyl)-β-alaninamide bis-trifluoroacetic acid salt

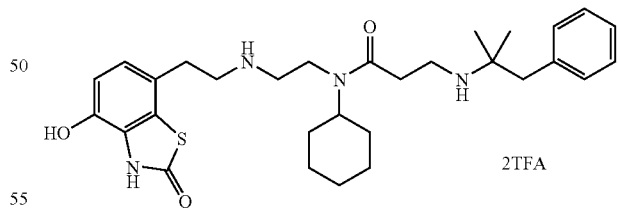

The title compound was prepared by the method of Example 14 using 1,1-dimethyl-2-phenylethylamine hydrochloride, and with the addition of 1 equivalent of triethylamine.

$^1$H NMR $\delta_{(DMSO)}$ 11.73 (1H, s), 10.13 (1H, s), 8.89-8.35 (4H, m), 7.37-7.22 (5H, m), 6.86 (1H, d), 6.75 (1H, d), 3.58-3.47 (3H, m), 3.29-3.11 (4H, m), 3.05-2.93 (4H, m), 2.87-2.78 (4H, m), 1.82-1.05 (10H, m), 1.21 (6H, s).

MS (Multimode+) 539 [(M-salt)+H]$^+$

EXAMPLE 20

N-Cyclohexyl-N-(2-{[2-(4-hydroxy-2-oxo-2,3-dihydro-1,3-benzothiazol-7-yl)ethyl]amino}ethyl)-$N^3$-[(2R)-2-phenylpropyl]-β-alaninamide bis-trifluoroacetic acid salt

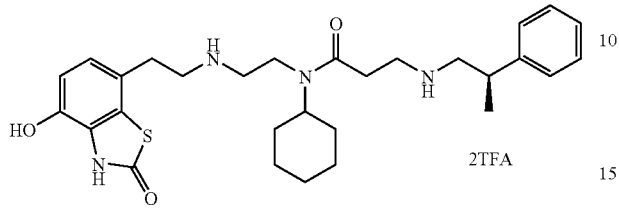

The title compound was prepared by the method of Example 14 using (2R)-2-phenylpropylamine.

$^1$H NMR $\delta_{(DMSO)}$ 11.73 (1H, s), 10.15 (1H, s), 8.89-7.93 (4H, m), 7.39-7.23 (5H, m), 6.85 (1H, d), 6.75 (1H, d), 3.36-3.48 (4H, m), 3.26-3.09 (6H, m), 3.02-2.94 (2H, m), 2.83-2.76 (4H, m), 1.82-1.04 (10H, m), 1.28 (3H, d).

MS (Multimode+) 525 [(M-salt)+H]$^+$

EXAMPLE 21

N-Cyclohexyl-N-(2-{[2-(4-hydroxy-2-oxo-2,3-dihydro-1,3-benzothiazol-7-yl)ethyl]amino}ethyl)-$N^3$-(2-methyl-2-phenylpropyl)-β-alaninamide bis-trifluoroacetic acid salt

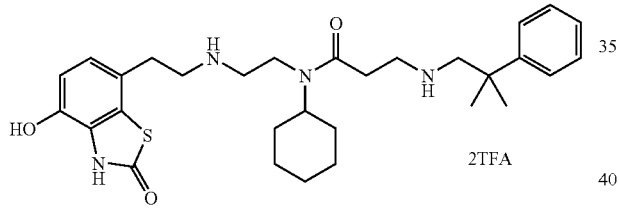

The title compound was prepared by the method of Example 14 using 2-methyl-2-phenylpropylamine.

$^1$H NMR $\delta_{(DMSO)}$ 11.74 (1H, s), 10.16 (1H, s), 8.63 (2H, s), 8.02 (2H, s), 7.47-7.43 (2H, m), 7.37 (2H, t), 7.29-7.24 (1H, m), 6.85 (1H, d), 6.76 (1H, d), 3.53-3.26 (5H, m), 3.18-3.08 (4H, m), 3.01-2.93 (2H, m), 2.85-2.75 (4H, m), 1.81-1.01 (10H, m), 1.38 (6H, s).

MS (Multimode+) 539 [(M-salt)+H]$^+$

EXAMPLE 22

$N^3$-[2-(3-Chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide bis-trifluoroacetic acid salt

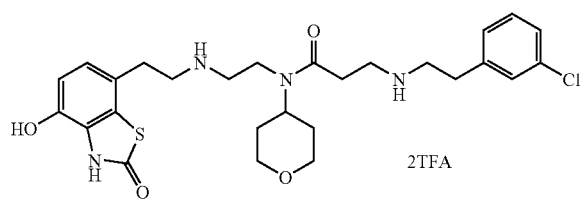

i) Benzyl [2-(4-hydroxy-2-oxo-2,3-dihydro-1,3-benzothiazol-7-yl)ethyl][2-(tetrahydro-2H-pyran-4-ylamino)ethyl]carbamate

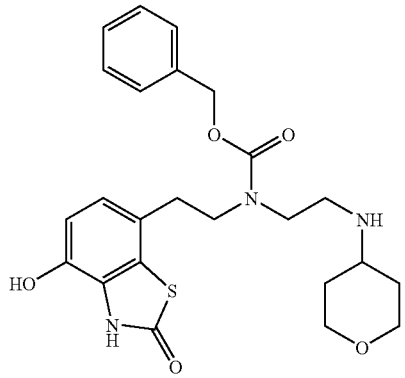

The sub-title compound was prepared by the method of Example 1 step iii) using 4-aminotetrahydropyran. The residue was purified by flash chromatography on silica using 7N methanolic ammonia:ethanol:ethyl acetate (10:15:75, then (10:40:50) as eluent to give the sub-title compound as an orange solid.

MS (Multimode+) 472.3 [M+H]$^+$ ii) Benzyl {2-[acryloyl(tetrahydro-2H-pyran-4-yl)amino]ethyl}[2-(4-hydroxy-2-oxo-2,3-dihydro-1,3-benzothiazol-7-yl)ethyl]carbamate

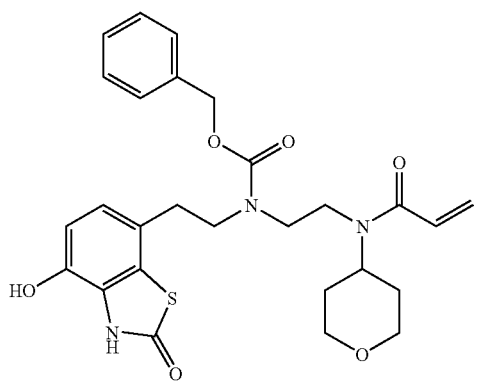

The amine as prepared in example 22 step i) was reacted with acryloyl chloride using the method of example 7 step i) using 4 equivalents of chlorotrimethylsilane and 5 equivalents of triethylamine, to give a mixture of the mono-acylated and the di-acylated material (1:2). The mixture was used without any further purification.

MS (Multimode+) 526 [M+H]$^+$ iii) N³-[2-(4-Chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide bis-trifluoroacetic acid salt

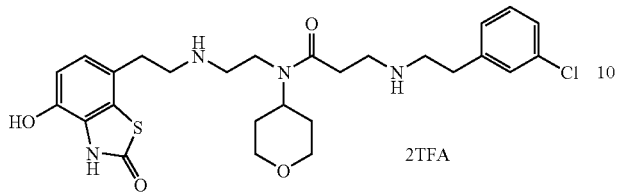

The acrylamide as prepared in example 22 step ii) was reacted with 3-chlorophenethylamine using the method of example 12 step ii) using 3 equivalents of the 3-chlorophenethylamine. The residue was dissolved in acetic acid rather than dichloromethane for the hydrogen bromide deprotection to give the title compound.

¹H NMR 90° C. δ$_{(DMSO)}$ 7.39-7.28 (3H, m), 7.23 (1H, d), 6.86 (1H, d), 6.75 (1H, dd), 3.96-3.80 (3H, m), 3.51 (2H, t), 3.39 (2H, t), 3.27-3.14 (6H, m), 3.07-2.96 (4H, m), 2.88-2.81 (4H, m), 1.78 (2H, d), 1.62 (2H, s).
MS (Multimode+) 547 [(M-salt)+H]⁺

EXAMPLE 23

N-Cycloheptyl-N-(2-{[2-(4-hydroxy-2-oxo-2,3-dihydro-1,3-benzothiazol-7-yl)ethyl]amino}ethyl)-N³-(2-phenylethyl)-β-alaninamide bis-trifluoroacetic acid salt

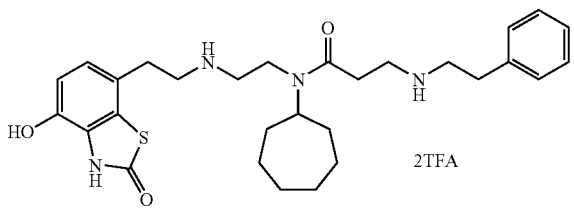

i) Benzyl [2-(cycloheptylamino)ethyl][2-(4-hydroxy-2-oxo-2,3-dihydro-1,3-benzothiazol-7-yl)ethyl]carbamate

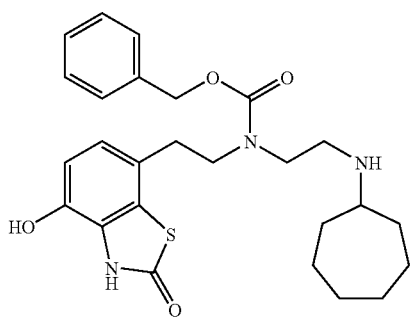

The sub-title compound was prepared by the method of Example 1 step iii) using cycloheptylamine. The product was purified by adsorption then elution from an SCX cartridge.

¹H NMR δ$_{(DMSO)}$ 7.36-7.29 (5H, m), 6.74 (1H, d), 6.67 (1H, d), 5.05 (2H, s), 3.44 (2H, t), 3.19 (2H, t), 2.71 (2H, t), 2.60 (2H, t), 2.58-2.53 (1H, m), 1.72-1.66 (2H, m), 1.60-1.43 (6H, m), 1.35-1.23 (4H, m).
MS (APCI+) 484 [M+H]⁺ ii) Benzyl {2-[acryloyl(cycloheptyl)amino]ethyl}[2-(4-hydroxy-2-oxo-2,3-dihydro-1,3-benzothiazol-7-yl)ethyl]carbamate

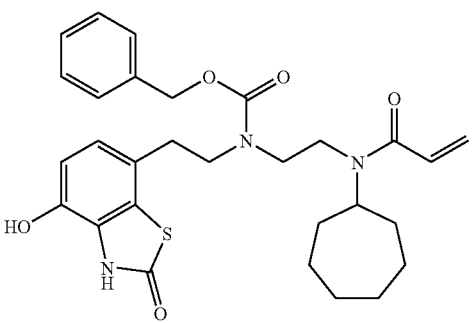

The amine as prepared in Example 23 step i) was reacted with acryloyl chloride using the method of example 7 step i) using 4 equivalents of chlorotrimethylsilane and 5 equivalents of triethylamine to give the sub-title compound as a pale yellow foam.

¹H NMR 90° C. δ$_{(DMSO)}$ 7.38-7.30 (5H, m), 6.74 (1H, d), 6.68 (1H, d), 6.65-6.52 (1H, m), 6.01 (1H, d), 5.53-5.49 (1H, m), 5.07 (2H, s), 3.44 (1H, t), 2.72 (1H, t), 1.63-1.34 (12H, m) (remaining 7H obscured).
MS (APCI+) 538 [M+H]⁺ iii) N-Cycloheptyl-N-(2-{[2-(4-hydroxy-2-oxo-2,3-dihydro-1,3-benzothiazol-7-yl)ethyl]amino}ethyl)-N³-(2-phenylethyl)-β-alaninamide bis-trifluoroacetic acid salt

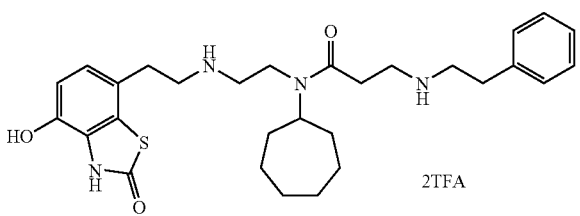

The acrylamide as prepared in example 23 step ii) was reacted with phenethylamine using the method of example 12 step ii), but using 3 equivalents of phenethylamine. The reaction was stirred at room temperature overnight, then heated at 50° C. for 4 h, prior to the hydrogen bromide deprotection, to give the title compound as a white solid.

¹H NMR 90° C. δ$_{(DMSO)}$ 7.35-7.23 (5H, m), 6.86 (1H, d), 6.75 (1H, d), 3.74-3.65 (1H, m), 3.48 (2H, t), 3.26-2.82 (14H, m), 1.78-1.46 (12H, m).
MS (Multimode+) 525.2 [(M-salt)+H]⁺

EXAMPLE 24

N³-[2-(3,4-Dichlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide bis-trifluoroacetic acid salt

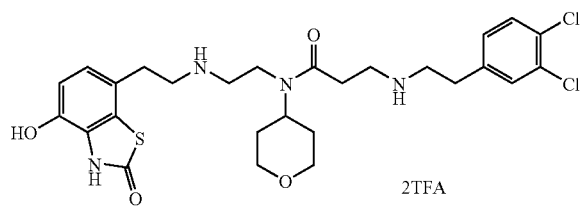

The acrylamide as prepared in Example 22 step ii) was reacted with 3,4-dichlorophenethylamine using the method of Example 7 step ii). The reaction mixture was diluted with ethyl acetate (2 ml), and purified by flash chromatography on silica using 7N methanolic ammonia:ethanol:ethyl acetate (10:40:50) as eluent. The residue was dissolved in acetic acid rather than dichloromethane for the hydrogen bromide deprotection to give the title compound.

$^1$H NMR 90° C. $\delta_{(DMSO)}$ 7.57-7.54 (2H, m), 7.27 (1H, d), 6.85 (1H, d), 6.75 (1H, d), 3.93 (2H, d), 3.84 (1H, s), 3.51 (2H, t), 3.39 (2H, t), 3.27-3.15 (6H, m), 3.04 (2H, s), 2.98 (2H, t), 2.87-2.82 (4H, m), 1.77 (2H, d), 1.62 (2H, s).

MS (Multimode+) 581.1 [(M-salt)+H]$^+$

EXAMPLE 25

N-(2-{[2-(4-Hydroxy-2-oxo-2,3-dihydro-1,3-benzothiazol-7-yl)ethyl]amino}ethyl)-N³-[2-(3-methylphenyl)ethyl]-N-(tetrahydro-2H-pyran-4-yl)-β-alaninamide bis-trifluoroacetic acid salt

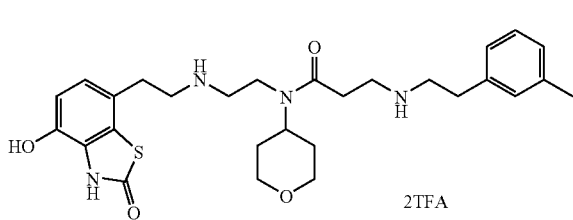

The title compound was prepared by the method of Example 24 using 3.18 equivalents of 3-methylphenethylamine.

$^1$H NMR $\delta_{(DMSO)}$ 7.20 (1H, t), 7.08-7.03 (3H, m), 6.86 (1H, d), 6.75 (1H, d), 3.95-3.91 (2H, m), 3.85 (1H, s), 3.52 (2H, t), 3.39 (2H, t), 3.24-2.82 (14H, m), 2.29 (3H, s), 1.77 (2H, d), 1.62 (2H, s).

MS (Multimode+) 527.2 [(M-salt)+H]$^+$

EXAMPLE 26

N³-[2-(4-Chlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide bis-trifluoroacetic acid salt

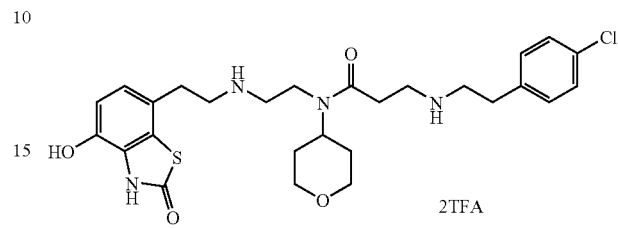

The title compound was prepared by the method of Example 24 using 3.78 equivalents of 4-chlorophenethylamine.

$^1$H NMR 90° C. $\delta_{(DMSO)}$ 7.37 (2H, d), 7.29 (2H, d), 6.85 (1H, d), 6.75 (1H, d), 3.95-3.91 (2H, m), 3.84 (1H, s), 3.52 (2H, t), 3.39 (2H, t), 3.24-3.14 (6H, m), 3.06-3.02 (2H, m), 2.98-2.94 (2H, m), 2.88-2.82 (4H, m), 1.77 (2H, d), 1.62 (2H, s).

MS (Multimode+) 547.1 [(M-salt)+H]$^+$

EXAMPLE 27

N-(2-{[2-(4-Hydroxy-2-oxo-2,3-dihydro-1,3-benzothiazol-7-yl)ethyl]amino}ethyl)-N³-[2-(2-methylphenyl)ethyl]-N-(tetrahydro-2H-pyran-4-yl)-β-alaninamide bis-trifluoroacetic acid salt

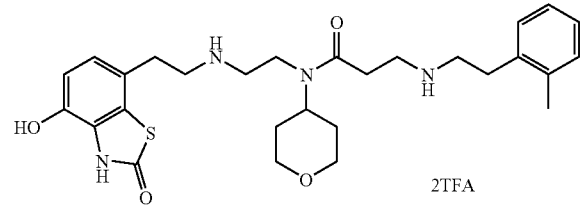

The title compound was prepared by the method of Example 24 using 3.38 equivalents of 2-methylphenethylamine.

$^1$H NMR $\delta_{(DMSO)}$ 7.23-7.11 (4H, m), 6.87 (1H, t), 6.76 (1H, t), 3.97-3.82 (3H, m), 3.56-3.51 (2H, m), 3.42-3.14 (8H, m), 3.06 (2H, s), 3.00-2.95 (2H, m), 2.91-2.83 (4H, m), 2.31 (3H, d), 1.78 (2H, s), 1.64 (2H, s).

MS (Multimode+) 527.2 [(M-salt)+H]$^+$

EXAMPLE 28

N³-[2-(4-Chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide bis-trifluoroacetic acid salt

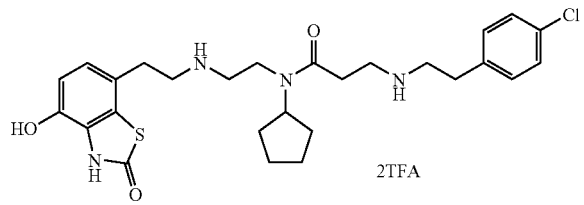

i) Benzyl [2-(cyclopentylamino)ethyl][2-(4-hydroxy-2-oxo-2,3-dihydro-1,3-benzothiazol-7-yl)ethyl]carbamate

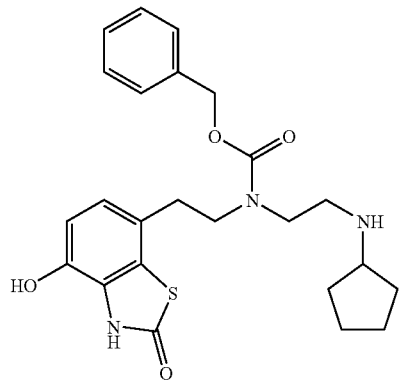

The sub-title compound was prepared by the method of Example 1 step iii) using cyclopentylamine.
¹H NMR δ$_{(DMSO)}$ 7.41-7.25 (5H, m), 6.73 (2H, m), 5.90 (1H, m), 5.04 (2H, m), 3.60 (1H, m), 3.47-2.95 (5H, m), 2.81-2.58 (4H, m), 2.04-1.21 (6H, m).
MS (APCI+) 456 [M+H]⁺ ii) Benzyl {2-[acryloyl(cyclopentyl)amino]ethyl}[2-(4-hydroxy-2-oxo-2,3-dihydro-1,3-benzothiazol-7-yl)ethyl]carbamate

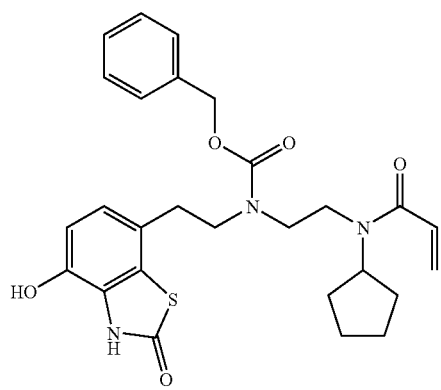

The amine as prepared in example 28 step i) (0.88 g) was dissolved in dichloromethane (20 ml), N,N-diisopropylethylamine (1.0 g, 1.35 ml) was added, followed by chlorotrimethylsilane (0.464 g, 0.54 ml), and the mixture was stirred at room temperature for 15 min. Acryloyl chloride (0.195 g, 0.175 ml) was added, and the mixture was stirred for a further 2 h. The solvents were removed in vacuo, and the residue was dissolved in THF (10 ml), 1M aqueous lithium hydroxide (5.8 ml) was added and the reaction mixture was stirred for 3 h. The reaction mixture was acidified with 2M aqueous HCl, extracted with ethyl acetate, washed with water, then with brine, dried (anhydrous Na₂SO₄), filtered and evaporated to give the sub-title compound as a light brown gum (0.82 g).
¹H NMR δ$_{(DMSO)}$ 11.62 (1H, m), 9.93 (1H, m), 7.34 (5H, m), 6.72 (3H, m), 5.99 (1H, m), 5.59 (1H, m), 5.04 (2H, m), 3.60 (1H, m), 3.42 (2H, m), 3.25-2.98 (4H, m), 2.67 (2H, m), 1.86-1.09 (8H, m).
MS (APCI+) 510 [M+H]⁺ iii) N³-[2-(4-Chlorophenyl)ethyl]-N-(1-ethylbutyl)-N-(2-{[2-(4-hydroxy-2-oxo-2,3-dihydro-1,3-benzothiazol-7-yl)ethyl]amino}ethyl)-β-alaninamide bis-trifluoroacetic acid salt

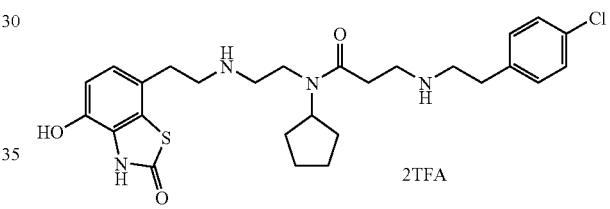

The acrylamide as prepared in example 28 step ii) was reacted with 2 equivalents of 4-chlorophenethylamine using the method of example 7 step ii). The residue was dissolved in acetic acid rather than dichloromethane for the hydrogen bromide deprotection to give the title compound.
¹H NMR δ$_{(DMSO)}$ 10.15 (1H, s), 7.41 (2H, m), 7.31 (2H, m), 6.86 (1H, m), 6.75 (1H, m), 4.08 (1H, m), 3.43 (2H, t), 3.18 (6H, m), 3.02 (2H, t), 2.92 (2H, t), 2.81 (4H, m), 1.83 (2H, m), 1.68 (2H, m), 1.52 (4H, m).

MS (Multimode+) 531.2 [(M-salt)+H]⁺

EXAMPLE 29

N³-[2-(2-Chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide bis-trifluoroacetic acid salt

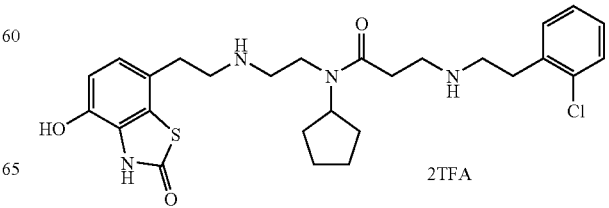

The title compound was prepared by the method of Example 28 using 2-chlorophenethylamine.

¹H NMR δ(DMSO) 10.21 (1H, s), 8.80 (4H, s), 7.47 (1H, m), 7.41 (1H, m), 7.33 (2H, m), 6.86 (1H, m), 6.76 (1H, m), 4.10 (1H, m), 3.46 (2H, t), 3.22 (4H, m), 3.15 (2H, t), 3.06 (4H, m), 2.84 (4H, m), 1.83 (2H, m), 1.68 (2H, m), 1.52 (4H, m).

MS (Multimode+) 531.2 [(M-salt)+H]⁺

EXAMPLE 30

N³-[2-(3-Chlorophenyl)ethyl]-N-cyclopentyl-N-(2-{[2-(4-hydroxy-2-oxo-2,3-dihydro-1,3-benzothiazol-7-yl)ethyl]amino}ethyl)-β-alaninamide bis-trifluoroacetic acid salt

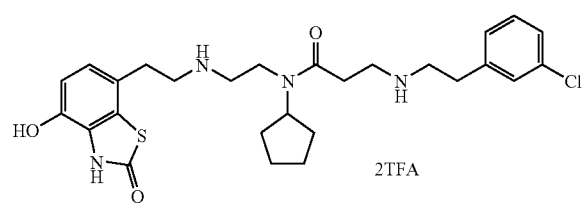

The title compound was prepared by the method of Example 28 using 3-chlorophenethylamine.

¹H NMR δ(DMSO) 10.17 (1H, s), 7.41-7.31 (3H, m), 7.25 (1H, m), 6.86 (1H, m), 6.75 (1H, m), 4.09 (1H, m), 3.44 (2H, t), 3.25 (2H, t), 3.16 (4H, m), 3.03 (2H, t), 2.95 (2H, t), 2.82 (4H, m), 1.83 (2H, m), 1.69 (2H, m), 1.52 (4H, m).

MS (Multimode+) 531.2 [(M-salt)+H]⁺

EXAMPLE 31

N-cyclopentyl-N-(2-{[2-(4-hydroxy-2-oxo-2,3-dihydro-1,3-benzothiazol-7-yl)ethyl]amino}ethyl)-N³-[(2S)-2-phenylpropyl]-β-alaninamide bis-trifluoroacetic acid salt

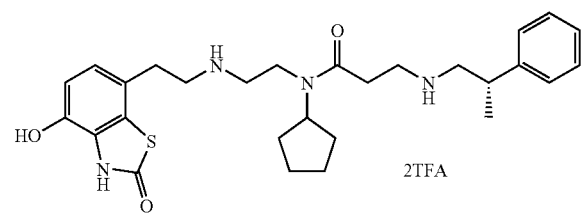

The title compound was prepared by the method of Example 28 using (2S)-2-phenylpropylamine.

¹H NMR δ(DMSO) 11.73 (1H, s), 10.15 (1H, s), 8.70-8.14 (4H, m), 7.39-7.24 (5H, m), 6.85 (1H, m), 6.75 (1H, m), 4.07 (1H, m), 3.42 (2H, t), 3.22 (2H, t), 3.13 (5H, m), 3.01 (2H, t), 2.80 (4H, m), 1.81 (2H, m), 1.69 (2H, m), 1.51 (4H, m), 1.28 (3H, d).

MS (Multimode+) 511.2 [(M-salt)+H]⁺

EXAMPLE 32

N-cyclopentyl-N-(2-{[2-(4-hydroxy-2-oxo-2,3-dihydro-1,3-benzothiazol-7-yl)ethyl]amino}ethyl)-N³-(2-methyl-2-phenylpropyl)-β-alaninamide bis-trifluoroacetic acid salt

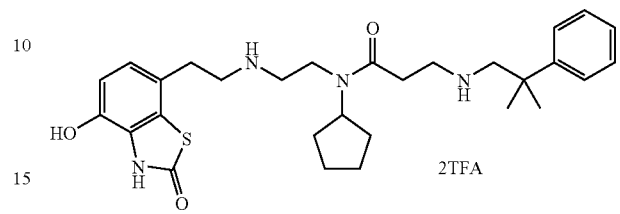

The title compound was prepared by the method of Example 28 using 2-methyl-2-phenylpropylamine.

¹H NMR δ(DMSO) 11.74 (1H, s), 10.13 (1H, s), 8.57 (2H, s), 7.94 (2H, s), 7.45 (2H, m), 7.37 (2H, m), 7.27 (1H, m), 6.86 (1H, m), 6.76 (1H, m), 4.05 (1H, m), 3.40 (4H, m), 3.13 (4H, m), 2.99 (2H, m), 2.80 (4H, m), 1.81 (2H, m), 1.69 (2H, m), 1.51 (4H, m), 1.38 (6H, s).

MS (Multimode+) 525.2 [(M-salt)+H]⁺

EXAMPLE 33

N-Cyclohexyl-N-(2-{[2-(4-hydroxy-2-oxo-2,3-dihydro-1,3-benzothiazol-7-yl)ethyl]amino}ethyl)-N³-(2-pyridin-2-ylethyl)-β-alaninamide bis-trifluoroacetic acid salt

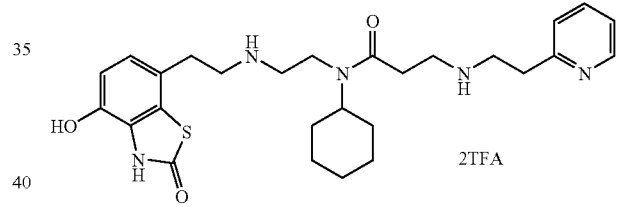

The title compound was prepared by the method of Example 14 using 2-pyridin-2-yl-ethylamine.

¹H NMR δ(DMSO) 11.73 (1H, s), 8.94-8.63 (4H, m), 8.53 (1H, s), 7.83 (1H, t), 7.40 (1H, d), 7.36-7.32 (1H, m), 6.86 (1H, d), 6.75 (1H, d), 3.59-3.47 (3H, m), 3.26-3.11 (8H, m), 3.06-2.98 (2H, m), 2.87-2.77 (4H, m), 1.82-1.02 (10H, m).

MS (Multimode+) 512.2 [(M-salt)+H]⁺

EXAMPLE 34

N-Cyclohexyl-N-(2-{[2-(4-hydroxy-2-oxo-2,3-dihydro-1,3-benzothiazol-7-yl)ethyl]amino}ethyl)-N³-[2-(4-hydroxyphenyl)ethyl]-β-alaninamide bis-trifluoroacetic acid salt

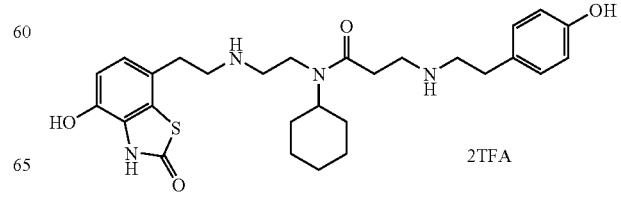

The title compound was prepared by the method of Example 14 using 4-hydroxyphenethylamine.

$^1$H NMR δ$_{(DMSO)}$ 11.73 (1H, s), 10.13 (1H, s), 9.33 (1H, s), 8.83-8.40 (4H, m), 7.05 (2H, d), 6.86 (1H, d), 6.76 (1H, d), 6.72 (2H, d), 3.58-3.45 (3H, m), 3.20-3.10 (6H, m), 3.04-2.96 (2H, m), 2.83-2.78 (6H, m), 1.82-1.04 (10H, m).

MS (Multimode+) 527.2 [(M-salt)+H]$^+$

EXAMPLE 35

N-Cyclohexyl-N-(2-{[2-(4-hydroxy-2-oxo-2,3-dihydro-1,3-benzothiazol-7-yl)ethyl]amino}ethyl)-N$^3$-[2-(2-thienyl)ethyl]-β-alaninamide bis-trifluoroacetic acid salt

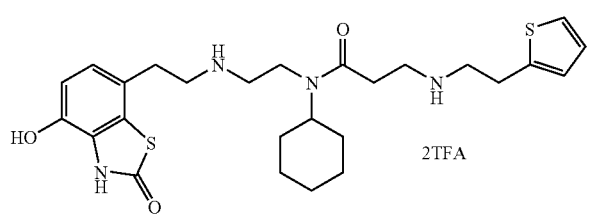

The title compound was prepared by the method of Example 14 using 2-(2-thienyl)ethylamine.

$^1$H NMR δ$_{(DMSO)}$ 11.73 (1H, s), 10.18-10.13 (1H, m), 8.88-8.55 (4H, m), 7.42 (1H, dd), 7.01-6.98 (2H, m), 6.88-6.85 (1H, m), 6.77-6.74 (1H, m), 3.58-3.46 (3H, m), 3.29-3.12 (8H, m), 3.03-2.97 (2H, m), 2.85-2.78 (4H, m), 1.81-1.04 (10H, m).

MS (Multimode+) 517.2 [(M-salt)+H]$^+$

EXAMPLE 36

N-Cycloheptyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide bis-trifluoroacetic acid salt

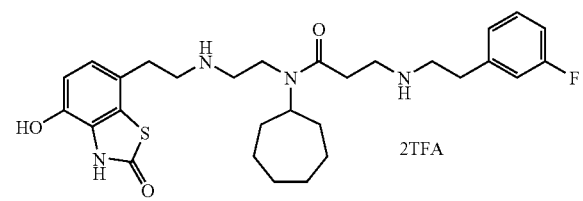

The acrylamide as prepared in example 23 step ii) was reacted with 3-fluorophenethylamine using the method of example 7 step ii) to give the title compound.

$^1$H NMR 90° C. δ$_{(DMSO)}$ 7.39-7.33 (1H, m), 7.12-7.02 (3H, m), 6.86 (1H, d), 6.75 (1H, d), 3.73-3.66 (1H, m), 3.52-3.47 (2H, m), 3.28-2.74 (14H, m), 1.75-1.45 (12H, m).

MS (Multimode+) 543.2 [(M-salt)+H]$^+$

EXAMPLE 37

N-Cycloheptyl-N-(2-{[2-(4-hydroxy-2-oxo-2,3-dihydro-1,3-benzothiazol-7-yl)ethyl]amino}ethyl)-N$^3$-[2-(3-hydroxyphenyl)ethyl]-β-alaninamide bis-trifluoroacetic acid salt

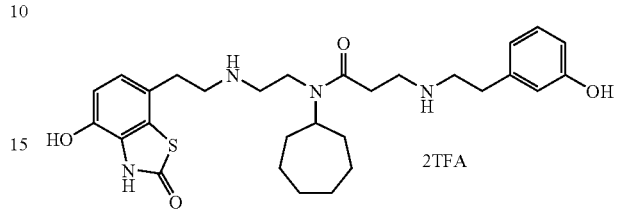

The acrylamide as prepared in example 23 step ii) was reacted with 3-hydroxyphenethylamine hydrochloride using the method of example 7 step ii), but adding 3 equivalents of triethylamine to the reaction mixture, to give the title compound.

$^1$H NMR 90° C. δ$_{(DMSO)}$ 7.10 (1H, t), 6.86 (1H, d), 6.75 (1H, d), 6.68-6.65 (3H, m), 3.73-3.67 (1H, m), 3.51-3.48 (2H, m), 3.22-2.82 (14H, m), 1.76-1.46 (12H, m).

MS (Multimode+) 541.2 [(M-salt)+H]$^+$

EXAMPLE 38

N$^3$-(1,1-Dimethyl-2-phenylethyl)-N-(2,2-dimethylpropyl)-N-(2-{[2-(4-hydroxy-2-oxo-2,3-dihydro-1,3-benzothiazol-7-yl)ethyl]amino}ethyl)-β-alaninamide bis-trifluoroacetic acid salt

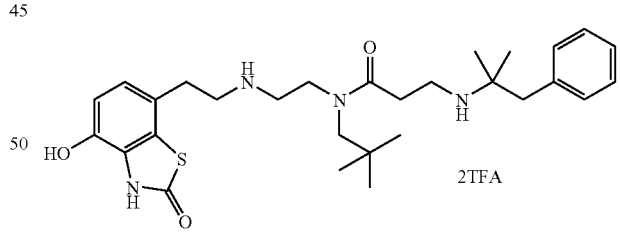

The title compound was prepared by the method of Example 7 step ii), using 1,1-dimethyl-2-phenylethylamine and heating the reaction at 65° C. for 180 h.

$^1$H NMR δ$_{(DMSO)}$ 11.74 (1H, s), 10.16-10.11 (1H, m), 8.85-8.35 (4H, m), 7.39-7.23 (5H, m), 6.89-6.84 (1H, m), 6.78-6.73 (1H, m), 3.65-3.58 (2H, m), 3.28-3.09 (8H, m), 2.97-2.93 (2H, m), 2.88-2.77 (4H, m), 1.21 (6H, s), 1.00-0.89 (9H, m).

MS (Multimode+) 527.2 [(M-salt)+H]$^+$

EXAMPLE 39

3-[{N-[2-(4-Chlorophenyl)ethyl]-β-alanyl}(2-{[2-(4-hydroxy-2-oxo-2,3-dihydro-1,3-benzothiazol-7-yl)ethyl]amino}ethyl)amino]-2,2-dimethylpropyl acetate diacetic acid salt

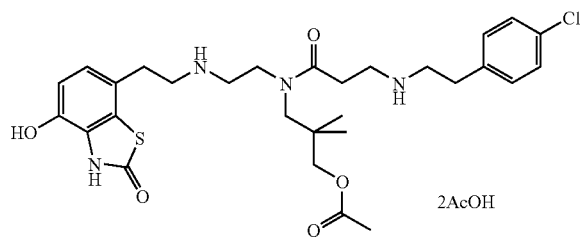

i) Benzyl {2-[(3-hydroxy-2,2-dimethylpropyl)amino]ethyl}[2-(4-hydroxy-2-oxo-2,3-dihydro-1,3-benzothiazol-7-yl)ethyl]carbamate

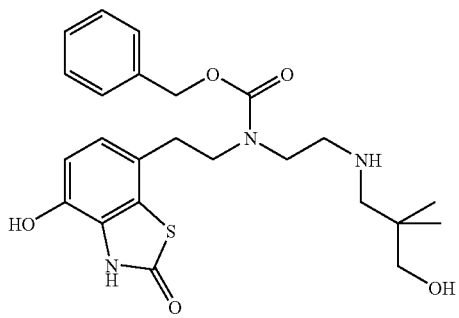

The sub-title compound was prepared by the method of Example 1 step iii) using 3-amino-2,2-dimethylpropan-1-ol. The reaction mixture was purified using adsorption then elution from an SCX cartridge, followed by flash chromatography on silica using 10% 0.880 ammonia in ethanol:ethyl acetate (2:3) as eluent.

$^1$H NMR $\delta_{(DMSO)}$ 7.41-7.26 (5H, m), 6.84-6.64 (2H, m), 5.04 (2H, d), 3.43-3.39 (2H, m), 3.22-3.17 (2H, m), 3.14-3.12 (2H, m), 2.76-2.65 (2H, m), 2.65-2.54 (2H, m), 2.38-2.22 (2H, m), 0.82-0.70 (6H, m).

MS (APCI+) 474 [M+H]$^+$ ii) Benzyl (3-chloro-3-oxopropyl)[2-(4-chlorophenyl)ethyl]carbamate

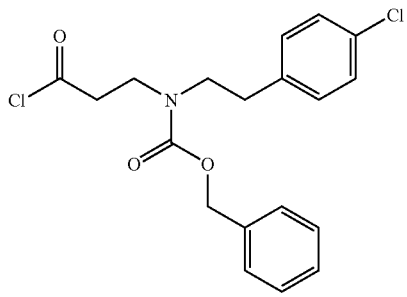

The sub-title compound was prepared by the method of example 5 step ii) using the acid as prepared in example 3 step i).

iii) 3-[{N-[2-(4-Chlorophenyl)ethyl]-β-alanyl}(2-{[2-(4-hydroxy-2-oxo-2,3-dihydro-1,3-benzothiazol-7-yl)ethyl]amino}ethyl)amino]-2,2-dimethylpropyl acetate diacetic acid salt

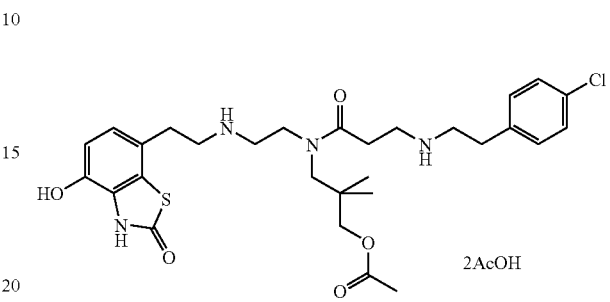

The amine as prepared in example 39 step i) was reacted with the acid chloride as prepared in example 39 step ii) using the method of example 6 step iv). The residue was purified by reverse phase HPLC (20-60% acetonitrile in aqueous ammonium acetate) to give the title compound.

$^1$H NMR $\delta_{(DMSO)}$ 7.30 (2H, d), 7.22 (2H, d), 6.77 (1H, d), 6.65 (1H, d), 3.81-3.64 (2H, m), 3.37-3.11 (4H, m), 2.80-2.56 (10H, m), 2.00 (3H, s), 1.86 (6H, s), 0.95-0.76 (6H, m).

MS (Multimode+) 591.2 [(M-salt)+H]$^+$

EXAMPLE 40

N$^3$-[2-(4-Chlorophenyl)ethyl]-N-(3-hydroxy-2,2-dimethylpropyl)-N-(2-{[2-(4-hydroxy-2-oxo-2,3-dihydro-1,3-benzothiazol-7-yl)ethyl]amino}ethyl)-β-alaninamide diacetic acid salt

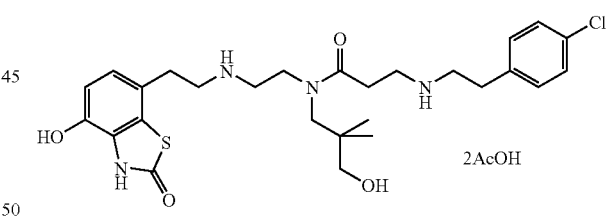

The acetate ester as prepared in example 39 step iii) (50 mg) was dissolved in a mixture of THF (2 ml) and water (0.2 ml). Lithium hydroxide monohydrate (10.5 mg) was added, and the reaction mixture was stirred at room temperature for 90 min. A second portion of lithium hydroxide monohydrate (10.5 mg) was added, followed by methanol (0.5 ml) and the reaction mixture was stirred at room temperature overnight. The reaction was quenched with acetic acid, then all solvents were removed by evaporation. The residue was purified by reverse phase HPLC (20-60% acetonitrile in aqueous ammonium acetate) to give the title compound (8 mg).

$^1$H NMR $\delta_{(DMSO)}$ 7.30 (2H, d), 7.22 (2H, d), 6.77 (1H, d), 6.66 (1H, d), 2.96 (2H, s), 2.76-2.53 (10H, m), 1.88 (6H, s), 0.82-0.72 (6H, m).

MS (Multimode+) 549.2 [(M-salt)+H]$^+$

EXAMPLE 41

$N^1$-(2,3-Dihydro-1H-inden-2-yl)-$N^1$-(2-{[2-(4-hydroxy-2-oxo-2,3-dihydro-1,3-benzothiazol-7-yl)ethyl]amino}ethyl)-$N^3$-(2-phenylethyl)-β-alaninamide bis-trifluoroacetic acid salt

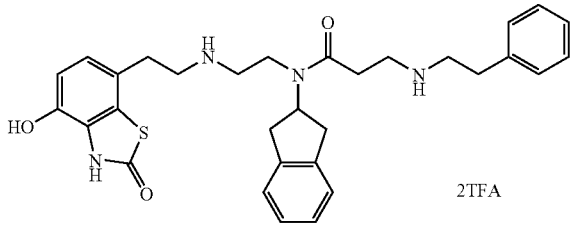

i) Benzyl [2-(2,3-dihydro-1H-inden-2-ylamino)ethyl][2-(4-hydroxy-2-oxo-2,3-dihydro-1,3-benzothiazol-7-yl)ethyl]carbamate

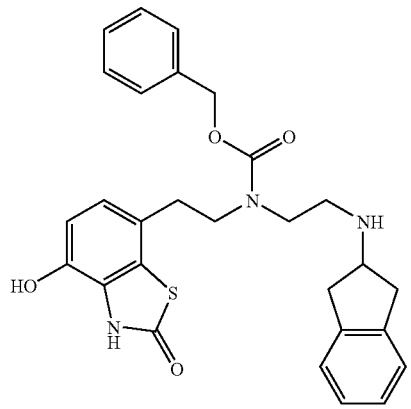

The aldehyde as prepared in Example 1 step ii) (4.2 g) was added to a mixture of 2-aminoindane hydrochloride (3.8 g) and sodium hydrogen carbonate (1.85 g) in a mixture of THF (80 ml) and water (8 ml), and the reaction mixture was stirred at room temperature for 15 min. Sodium cyanoborohydride (1.4 g) was added, followed by acetic acid (1.9 ml) and the reaction stirred for a further 18 h. The reaction was quenched with saturated aqueous sodium hydrogen carbonate, extracted with ethyl acetate (×3), washed with brine, dried (anhydrous $Na_2SO_4$), filtered and evaporated. The residue was purified by flash chromatography on silica using ethyl acetate:dichloromethane (50:50), changing to ethyl acetate (100%) as eluent. The residue was triturated with ethyl acetate and the resulting white solid was collected by filtration to give the sub-title compound.

$^1$H NMR 90° C. δ$_{(DMSO)}$ 9.72 (1H, s), 7.62-7.54 (5H, m), 7.48-7.41 (4H, m), 6.96 (1H, d), 6.90 (1H, d), 5.31 (2H, s), 4.24 (1H, m), 3.72-3.62 (5H, m), 3.56-3.45 (3H, m), 3.26 (2H), 2.95 (2H, t).

ii) Benzyl {2-[acryloyl(2,3-dihydro-1H-inden-2-yl)amino]ethyl}[2-(4-hydroxy-2-oxo-2,3-dihydro-1,3-benzothiazol-7-yl)ethyl]carbamate

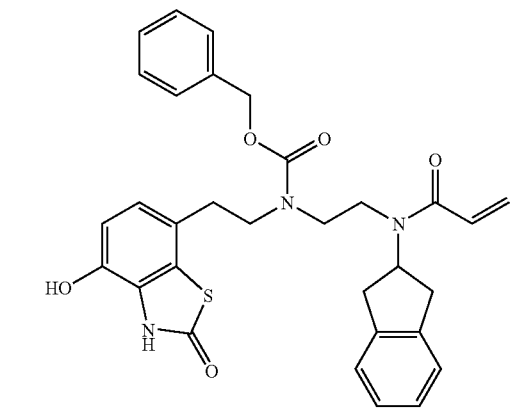

The amine as prepared in Example 41 step i) was reacted with 5 equivalents of triethylamine, 4 equivalents of chlorotrimethylsilane and 1 equivalent of acryloyl chloride using the method of example 7 step i). On warming to room temperature a further 2 equivalents of triethylamine and 1.6 equivalents of chlorotrimethylsilane were added, and the reaction stirred for 1 h. The mixture was cooled to 0° C., and 0.3 equivalents of acryloyl chloride was added, and the mixture was stirred, warming to room temperature, for a further 2 h. The reaction mixture was diluted with dichloromethane, washed with 2M aqueous HCl, dried (anhydrous $Na_2SO_4$), filtered and evaporated to give the sub-title compound.

$^1$H NMR 90° C. δ$_{(DMSO)}$ 7.34-7.28 (5H, m), 7.16-7.11 (4H, m), 6.72-6.67 (2H, m), 6.09-6.06 (2H, m), 5.55 (1H, s), 5.01 (2H, s), 4.84 (1H, s), 4.04 (1H, m), 3.48-3.46 (1H, m), 3.35-3.34 (2H, m), 3.22-3.02 (3H, m), 2.89-2.84 (2H, m), 2.73-2.66 (3H, m).

iii) $N^1$-(2,3-Dihydro-1H-inden-2-yl)-$N^1$-(2-{[2-(4-hydroxy-2-oxo-2,3-dihydro-1,3-benzothiazol-7-yl)ethyl]amino}ethyl)-$N^3$-(2-phenylethyl)-β-alaninamide bis-trifluoroacetic acid salt

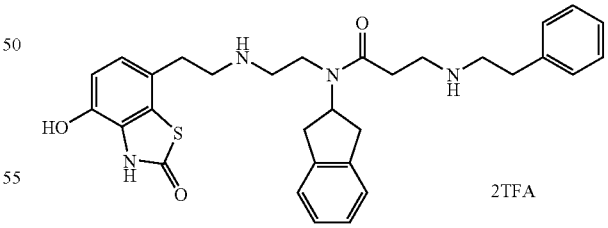

The acrylamide as prepared in Example 41 step ii) (190 mg) was dissolved in ethanol (20 ml), phenethylamine (50 mg) was added and the mixture was stirred at 50° C. for 18 h. A second portion of phenethylamine (100 mg) was added and the mixture was stirred at 50° C. for a further 24 h. A third portion of phenethylamine (100 mg) was added and the mixture was stirred at 50° C. for a further 2 days. The solvents were removed in vacuo and the residue was purified by flash chromatography on silica using ethyl acetate (100%), changing to 15% methanol in ethyl acetate as the eluents. The residue was treated with hydrogen bromide 30 wt % solution in acetic acid (1 ml), and the mixture was stirred at room temperature for 2 h. Toluene (1 ml) was added to the reaction and all solvents were removed in vacuo (×3). The residue was purified by reverse phase HPLC (5-95% acetonitrile in aqueous TFA) to give the title compound (26 mg).

$^1$H NMR 90° C. $\delta_{(DMSO)}$ 7.34-7.21 (7H, m), 7.16-7.15 (2H, m), 6.83 (1H, d), 6.74 (1H, d), 4.76 (1H, m), 3.57 (2H, t), 3.27-3.19 (6H, m), 3.15-3.11 (6H, m), 3.00-2.94 (4H, m), 2.83 (2H, t).

MS (Multimode+) 545.2 [(M-salt)+H]$^+$

EXAMPLE 42

$N^3$-[2-(3-Chlorophenyl)ethyl]-$N^1$-(2,3-dihydro-1H-inden-2-yl)-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

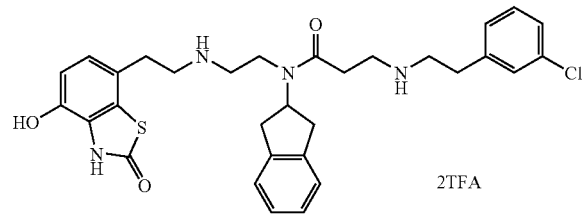

The acrylamide as prepared in Example 41 step ii) (200 mg) was dissolved in ethanol (15 ml), 3-chlorophenethylamine (160 mg) was added and the mixture was stirred at room temperature for 5 days. The solvents were removed in vacuo and the residue was purified by flash chromatography on silica using ethyl acetate (100%), changing to 1% 0.880 ammonia and 10% methanol in ethyl acetate as the eluents. The residue was treated with hydrogen bromide 30 wt % solution in acetic acid (3 ml), and the mixture was stirred at room temperature for 2 h. Toluene (1 ml) was added to the reaction and all solvents were removed in vacuo (×3). The residue was purified by reverse phase HPLC (5-95% acetonitrile in aqueous TFA) to give the title compound (19 mg).

$^1$H NMR 90° C. $\delta_{(DMSO)}$ 7.34-7.27 (3H, m), 7.21 (3H, d), 7.14 (2H, s), 6.81 (1H, d), 6.72 (1H, d), 4.73 (1H, t), 3.55 (2H, s), 3.21-3.11 (12H, m), 2.51 (2H, m), 2.95 (2H, m), 2.80 (2H, t).

MS (Multimode+) 579.2 [(M-salt)+H]$^+$

EXAMPLE 43

$N^1$-(2,2-Dimethylpropyl)-$N^1$-(2-{[2-(4-hydroxy-2-oxo-2,3-dihydro-1,3-benzothiazol-7-yl)ethyl]amino}ethyl)-$N^3$-[2-(3-methoxyphenyl)ethyl]-β-alaninamide bis-trifluoroacetic acid salt

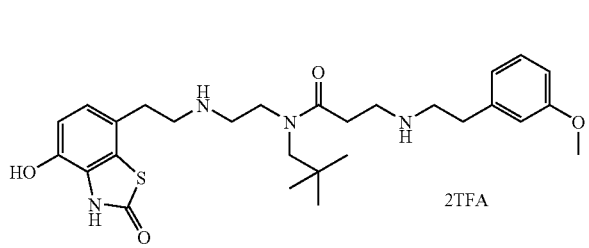

The title compound was prepared by the method of Example 7 step ii), using 3-methoxyphenethylamine.

$^1$H NMR $\delta_{(DMSO)}$ 11.74 (1H, s), 10.18-10.12 (1H, m), 8.89-8.47 (4H, m), 7.28-7.22 (1H, m), 6.88-6.80 (4H, m), 6.78-6.73 (1H, m), 3.75 (3H, dd), 3.64-3.56 (2H, m), 3.26-3.07 (10H, m), 2.94-2.75 (6H, m), 0.98-0.87 (9H, m).

MS (Multimode+) 529.2 [(M-salt)+H]$^+$

EXAMPLE 44

$N^1$-(2,2-Dimethylpropyl)-$N^3$-[2-(3-fluorophenyl)ethyl]-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

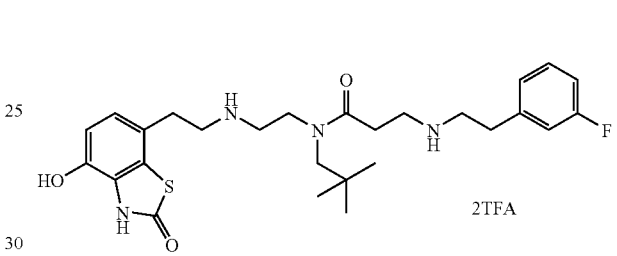

The title compound was prepared by the method of Example 7 step ii) using 3-fluorophenethylamine.

$^1$H NMR $\delta_{(DMSO)}$ 11.74 (1H, s), 10.16-10.12 (1H, m), 8.85-8.49 (4H, m), 7.42-7.35 (1H, m), 7.18-7.07 (3H, m), 6.88-6.84 (1H, m), 6.77-6.73 (1H, m), 3.64-3.56 (2H, m), 3.28-3.07 (10H, m), 2.96 (2H, t), 2.87-2.75 (4H, m), 0.97-0.87 (9H, m).

MS (Multimode+) 517.2 [(M-salt)+H]$^+$

EXAMPLE 45

$N^1$-(2-{[2-(4-Hydroxy-2-oxo-2,3-dihydro-1,3-benzothiazol-7-yl)ethyl]amino}ethyl)-$N^1$-(2-methyl-2-phenylpropyl)-$N^3$-(2-phenylethyl)-β-alaninamide bis-trifluoroacetic acid salt

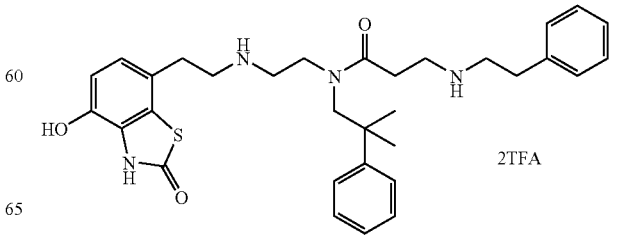

i) Benzyl [2-(4-hydroxy-2-oxo-2,3-dihydro-1,3-benzothiazol-7-yl)ethyl]{2-[(2-methyl-2-phenylpropyl)amino]ethyl}carbamate

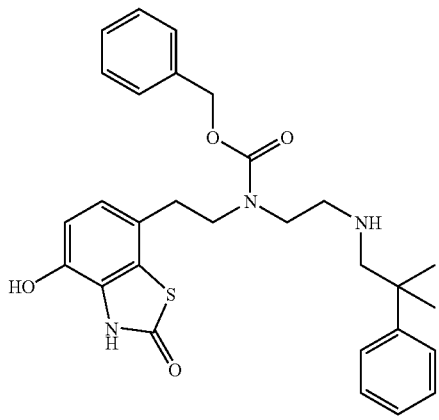

The aldehyde as prepared in Example 1 step ii) (2.0 g) was added to a solution of (2-methyl-2-phenylpropyl)amine (1.54 g) in a mixture of THF (40 ml), water (9 ml), and acetic acid (592 ul), and the reaction mixture was stirred at room temperature for 30 min. Sodium cyanoborohydride (0.65 g) was added and the reaction stirred for a further 18 h. The reaction was quenched with saturated aqueous sodium hydrogen carbonate, extracted with ethyl acetate (×3), washed with brine, dried (anhydrous $Na_2SO_4$), filtered and evaporated. The residue was purified by flash chromatography on silica using methanol in dichloromethane (1, 2, 5, 10%) as the eluents to give the sub-title compound (1.65 g).

MS (APCI+) 520 [M+H]$^+$ ii) $N^1$-(2-{[2-(4-Hydroxy-2-oxo-2,3-dihydro-1,3-benzothiazol-7-yl)ethyl]amino}ethyl)-$N^1$-(2-methyl-2-phenylpropyl)-$N^3$-(2-phenylethyl)-β-alaninamide bis-trifluoroacetic acid salt

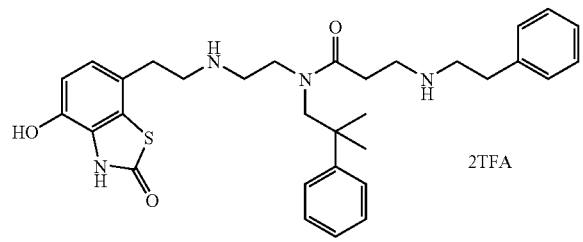

The title compound was prepared by the method of Example 6 step iv) using the amine as prepared in Example 45 step i) and 4 equivalents of chlorotrimethylsilane. A second portion of the acid chloride in dichloromethane was added, and the mixture stirred for a further 3 h. The reaction mixture was diluted with methanol and the solvents were removed in vacuo, prior to the hydrogen bromide deprotection.

$^1$H NMR $δ_{(DMSO)}$ 11.75 (1H, s), 10.18-10.13 (1H, m), 8.76-8.48 (4H, m), 7.44-7.16 (10H, m), 6.82 (1H, d), 6.77-6.73 (1H, m), 3.53-3.46 (2H, m), 3.25-2.71 (16H, m), 1.39-1.26 (6H, m).

MS (Multimode+) 561.2 [(M-salt)+H]$^+$

EXAMPLE 46

$N^3$-[2-(2-Chlorophenyl)ethyl]-$N^1$-(4,4-difluorocyclohexyl)-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

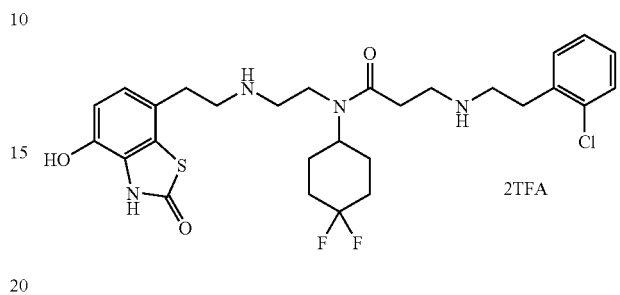

i) Benzyl {2-[acryloyl(4,4-difluorocyclohexyl)amino]ethyl}[2-(4-hydroxy-2-oxo-2,3-dihydro-1,3-benzothiazol-7-yl)ethyl]carbamate

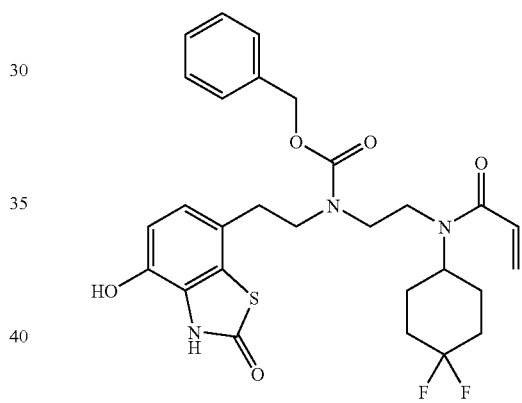

The amine as prepared in Example 4 step i) (1 g) was dissolved in THF (20 ml), and N,N-diisopropylethylamine (0.779 g, 1.05 ml) was added, followed by acryloyl chloride (0.448 g, 0.402 ml) and the reaction was stirred at room temperature for 5 h. 0.5M Aqueous lithium hydroxide (9.89 ml) was added and the mixture was stirred for a further 20 h. The mixture was acidified with 2M aqueous HCl, extracted with ethyl acetate (3×50 ml), washed with brine, dried (anhydrous $Na_2SO_4$), filtered and evaporated. The residue was purified by flash chromatography on silica using 5% methanol in dichloromethane as eluent to give the sub-title compound as a white solid (0.29 g).

$^1$H NMR $δ_{(DMSO)}$ 7.42-7.26 (5H, m), 6.78 (1H, m), 6.69 (1H, m), 6.26-5.64 (3H, m), 5.06 (2H, s), 3.41 (2H, m), 3.20 (2H, m), 3.05 (1H, m), 2.70 (2H, m), 2.51 (2H, m), 2.07-1.87 (4H, m), 1.81-1.45 (4H, m).

MS (APCI+) 560 [M+H]$^+$ ii) N³-[2-(2-Chlorophenyl)ethyl]-N¹-(4,4-difluorocyclohexyl)-N¹-(2-{[2-(4-hydroxy-2-oxo-2,3-dihydro-1,3-benzothiazol-7-yl)ethyl]amino}ethyl)-β-alaninamide bis-trifluoroacetic acid salt

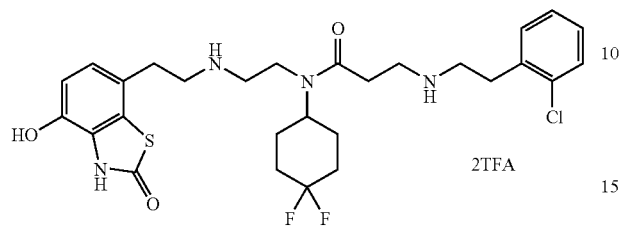

The title compound was prepared by the method of Example 7 step ii) using the acrylamide as prepared in Example 46 step i) with 2 equivalents of 2-chlorophenethylamine. The solvents were removed in vacuo, and the residue azeotroped with acetonitrile and toluene. The residue was dissolved in acetic acid rather than dichloromethane for the hydrogen bromide deprotection, and azeotroped with toluene and acetonitrile before purification by reverse phase HPLC.

$^1$H NMR $\delta_{(DMSO)}$ 10.14 (1H, s), 7.48 (1H, m), 7.40 (1H, m), 7.33 (2H, m), 6.86 (1H, m), 6.76 (1H, m), 3.87 (1H, m), 3.45 (2H, t), 3.26-3.04 (8H, m), 3.01 (2H, t), 2.86 (2H, t), 2.80 (2H, t), 2.16-1.93 (4H, m), 1.84-1.60 (4H, m).

MS (Multimode+) 581.2 [(M-salt)+H]$^+$

EXAMPLE 47

N³-[2-(3-Chlorophenyl)ethyl]-N¹-(4,4-difluorocyclohexyl)-N¹-(2-{[2-(4-hydroxy-2-oxo-2,3-dihydro-1,3-benzothiazol-7-yl)ethyl]amino}ethyl)-β-alaninamide bis-trifluoroacetic acid salt

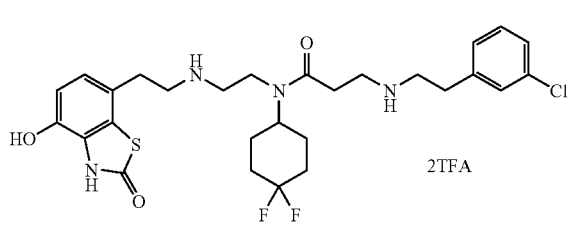

The title compound was prepared by the method of Example 46 step ii) using 3-chlorophenethylamine.

$^1$H NMR $\delta_{(DMSO)}$ 7.36 (3H, m), 7.25 (1H, m), 6.85 (1H, d), 6.75 (1H, d), 6.54 (2H, s), 3.85 (1H, m), 3.43 (2H, t), 3.26-3.16 (4H, m), 3.12 (2H, t), 3.01-2.89 (4H, m), 2.84 (2H, t), 2.79 (2H, t), 2.72 (2H, t), 1.81-1.60 (4H, m), 2.14-1.92 (4H, m).

MS (Multimode+) 581.2 [(M-salt)+H]$^+$

EXAMPLE 48

N³-[2-(4-Chlorophenyl)ethyl]-N¹-(4,4-difluorocyclohexyl)-N¹-(2-{[2-(4-hydroxy-2-oxo-2,3-dihydro-1,3-benzothiazol-7-yl)ethyl]amino}ethyl)-β-alaninamide bis-trifluoroacetic acid salt The title compound was prepared by the method of Example 46 step ii) using 4-chlorophenethylamine.

$^1$H NMR $\delta_{(DMSO)}$ 10.15 (1H, s), 7.41 (2H, d), 7.30 (2H, d), 6.86 (1H, m), 6.76 (1H, m), 3.85 (1H, m), 3.44 (2H, t), 3.20 (2H, t), 3.19 (2H, t), 3.13 (2H, t), 3.07-2.77 (6H, m), 2.72 (2H, t), 2.12-1.91 (4H, m), 1.84-1.60 (4H, m).

MS (Multimode+) 581.2 [(M-salt)+H]$^+$

EXAMPLE 49

N³-[2-(3,4-Dichlorophenyl)ethyl]-N¹-(4,4-difluorocyclohexyl)-N¹-(2-{[2-(4-hydroxy-2-oxo-2,3-dihydro-1,3-benzothiazol-7-yl)ethyl]amino}ethyl)-β-alaninamide bis-trifluoroacetic acid salt The title compound was prepared by the method of Example 46 step ii) using 3,4-dichlorophenethylamine.

$^1$H NMR $\delta_{(DMSO)}$ 10.15 (1H, s), 7.61 (2H, m), 7.29 (1H, m), 6.86 (1H, m), 6.75 (1H, m), 3.85 (1H, m), 3.44 (2H, t), 3.25 (2H, t), 3.19 (2H, t), 3.13 (2H, t), 3.03-2.90 (4H, m), 2.87-2.77 (4H, m), 2.15-1.92 (4H, m), 1.84-1.60 (4H, m).

MS (Multimode+) 615.1 [(M-salt)+H]$^+$

EXAMPLE 50

N³-[2-(3-Chlorophenyl)ethyl]-N¹-cycloheptyl-N¹-(2-
{[2-(4-hydroxy-2-oxo-2,3-dihydro-1,3-benzothiazol-
7-yl)ethyl]amino}ethyl)-β-alaninamide bis-trifluoro-
acetic acid salt

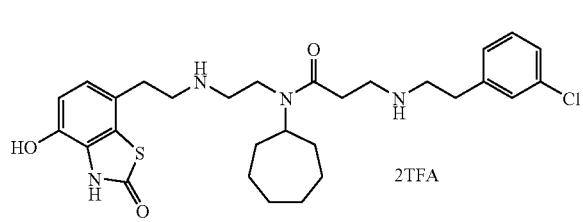

The title compound was prepared by the method of Example 36, using 3-chlorophenethylamine.

¹H NMR 90° C. $\delta_{(DMSO)}$ 7.37-7.22 (4H, m), 6.85 (1H, d), 6.75 (1H, d), 3.73-3.67 (1H, m), 3.47 (2H, t), 3.27-2.95 (12H, m), 2.83 (2H, t), 1.74-1.45 (12H, m).

MS (Multimode+) 559.2 [(M-salt)+H]⁺

EXAMPLE 51

N³-[2-(4-Chlorophenyl)ethyl]-N¹-cycloheptyl-N¹-(2-
{[2-(4-hydroxy-2-oxo-2,3-dihydro-1,3-benzothiazol-
7-yl)ethyl]amino}ethyl)-β-alaninamide bis-trifluoro-
acetic acid salt

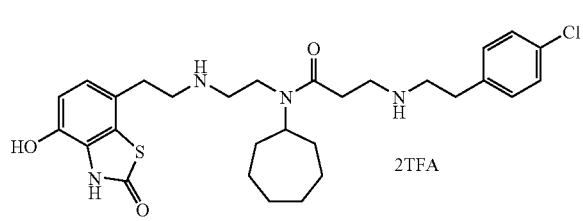

The title compound was prepared by the method of Example 36, using 4-chlorophenethylamine, stirring the reaction mixture at room temperature for a further 3 days after the 18 h at 50° C., and azeotroping with toluene and methanol after the deprotection.

¹H NMR 90° C. $\delta_{(DMSO)}$ 7.37 (2H, d), 7.29 (2H, d), 6.86 (1H, d), 6.75 (1H, d), 3.72-3.65 (1H, m), 3.49 (2H, t), 3.25-2.83 (14H, m), 1.74-1.45 (12H, m).

MS (Multimode+) 559.2 [(M-salt)+H]⁺

EXAMPLE 52

N¹-Cycloheptyl-N¹-(2-{[2-(4-hydroxy-2-oxo-2,3-
dihydro-1,3-benzothiazol-7-yl)ethyl]amino}ethyl)-
N³-[2-(2-thienyl)ethyl]-β-alaninamide bis-trifluoro-
acetic acid salt

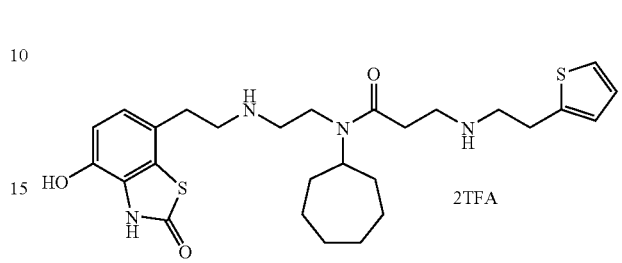

The title compound was prepared by the method of Example 51 using 2-(2-thienyl)ethylamine.

¹H NMR $\delta_{(DMSO)}$ 7.36 (1H, d), 6.99-6.97 (2H, m), 6.86 (1H, d), 6.75 (1H, d), 3.73-3.66 (1H, m), 3.49 (2H, t), 3.28-2.83 (14H, m), 1.75-1.47 (12H, m).

MS (Multimode+) 531.2 [(M-salt)+H]⁺

EXAMPLE 53

N¹-Cycloheptyl-N³-[2-(3,4-difluorophenyl)ethyl]-
N¹-(2-{[2-(4-hydroxy-2-oxo-2,3-dihydro-1,3-ben-
zothiazol-7-yl)ethyl]amino}ethyl)-β-alaninamide
bis-trifluoroacetic acid salt

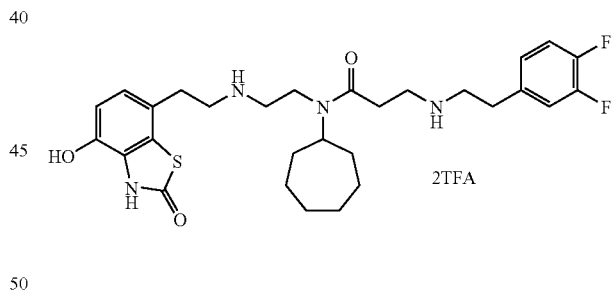

The title compound was prepared by the method of Example 37 using 3,4-difluorophenethylamine hydrochloride, and heating the reaction for a further 18 h at 60° C.

The residue was dissolved in acetic acid rather than dichloromethane for the hydrogen bromide deprotection.

¹H NMR $\delta_{(DMSO)}$ 7.40 (2H, m), 7.15 (1H, m), 6.90 (1H, m), 6.78 (1H, m), 3.67 (1H, m), 3.46 (2H, t), 3.25-3.12 (6H, m), 3.06 (2H, t), 2.94 (2H, t), 2.82 (4H, m), 1.75-1.59 (8H, m), 1.53-1.44 (4H, m).

MS (Multimode+) 561.2 [(M-salt)+H]⁺

EXAMPLE 54

$N^1$-Cycloheptyl-$N^3$-{2-[3-(difluoromethoxy)phenyl]ethyl}-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

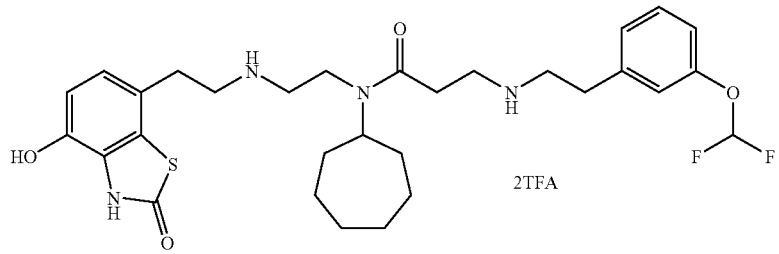

The title compound was prepared by the method of Example 37 using {2-[3-(difluoromethoxy)phenyl]ethyl}amine hydrochloride. The residue was dissolved in acetic acid rather than dichloromethane for the hydrogen bromide deprotection.

$^1$H NMR δ$_{(DMSO)}$ 11.73 (1H, s), 10.13 (1H, s), 8.61 (2H, bs), 8.54 (2H, bs), 7.41 (1H, m), 7.24 (1H, t), 7.16 (1H, m), 7.10 (2H, m), 6.87 (1H, m), 6.75 (1H, m), 3.68 (1H, m), 3.45 (2H, t), 3.24-3.10 (6H, m), 3.05 (2H, bs), 2.96 (2H, m), 2.81 (4H, m), 1.75-1.60 (8H, m), 1.49 (4H, m).

MS (Multimode+) 591.2 [(M-salt)+H]$^+$

EXAMPLE 55

$N^1$-Cycloheptyl-$N^3$-[2-(2,4-difluorophenyl)ethyl]-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

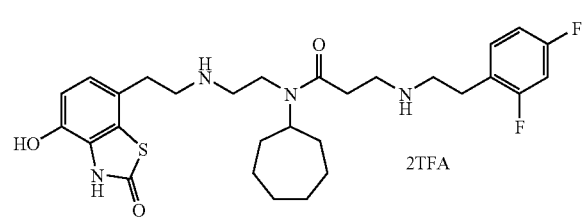

The title compound was prepared by the method of Example 54 using 2,4-difluorophenethylamine hydrochloride.

$^1$H NMR δ$_{(DMSO)}$ 7.42 (1H, m), 7.23 (1H, m), 7.09 (1H, m), 6.89 (1H, m), 6.77 (1H, m), 3.68 (1H, m), 3.46 (2H, t), 3.21-3.12 (6H, m), 3.06 (2H, t), 2.96 (2H, t), 2.82 (4H, m), 1.75-1.60 (8H, m), 1.47 (4H, m).

MS (Multimode+) 561.2 [(M-salt)+H]$^+$

EXAMPLE 56

$N^1$-Cycloheptyl-$N^3$-[2-(2,3-difluorophenyl)ethyl]-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

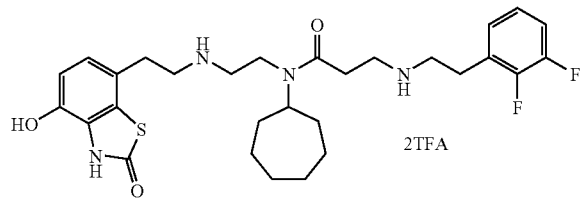

The title compound was prepared by the method of Example 54 using 2,3-difluorophenethylamine hydrochloride.

$^1$H NMR δ$_{(DMSO)}$ 7.33 (1H, m), 7.21 (2H, t), 6.90 (1H, m), 6.78 (1H, m), 3.67 (1H, m), 3.46 (2H, t), 3.26-3.12 (6H, m), 3.05 (4H, m), 2.81 (4H, m), 1.73-1.60 (8H, m), 1.49 (4H, m).

MS (Multimode+) 561.2 [(M-salt)+H]$^+$

EXAMPLE 57

$N^3$-[2-(2-Chloro-4-fluorophenyl)ethyl]-$N^1$-cycloheptyl-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

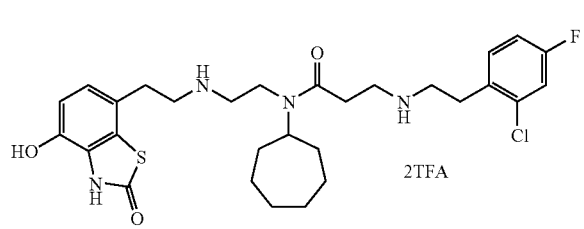

The title compound was prepared by the method of Example 54 using 2-chloro-4-fluorophenethylamine hydrochloride.

$^1$H NMR δ$_{(DMSO)}$ 11.74 (1H, s), 10.13 (1H, s), 8.61 (4H, bs), 7.47 (2H, m), 7.25 (1H, t), 6.87 (1H, m), 6.76 (1H, m), 3.68 (1H, m), 3.46 (2H, t), 3.20 (6H, m), 3.05 (4H, t), 2.83 (4H, m), 1.76-1.60 (8H, m), 1.48 (4H, m).

MS (Multimode+) 577.2 [(M-salt)+H]$^+$

EXAMPLE 58

N$^1$-Cycloheptyl-N$^3$-[2-(3,5-difluorophenyl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

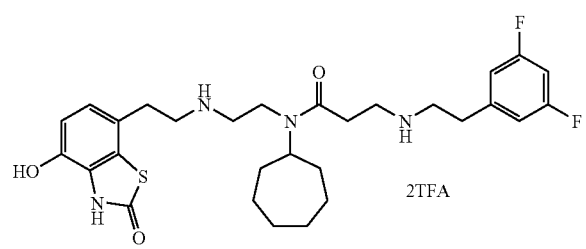

The title compound was prepared by the method of Example 37 using 3,5-difluorophenethylamine hydrochloride.

$^1$H NMR 90° C. δ$_{(DMSO)}$ 7.03-6.98 (3H, m), 6.86 (1H, d), 6.75 (1H, d), 3.71-3.66 (1H, m), 3.48 (2H, t), 3.29-2.83 (14H, m), 1.74-1.45 (12H, m).

MS (Multimode+) 561.2 [(M-salt)+H]$^+$

EXAMPLE 59

N$^1$-(1-Adamantylmethyl)-N$^1$-(2-{[2-(4-hydroxy-2-oxo-2,3-dihydro-1,3-benzothiazol-7-yl)ethyl]amino}ethyl)-N$^3$-(2-phenylethyl)-β-alaninamide bis-trifluoroacetic acid salt

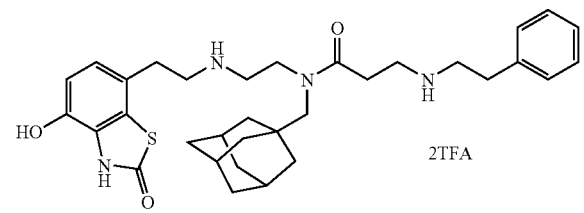

i) Benzyl {2-[(1-adamantylmethyl)amino]ethyl}[2-(4-hydroxy-2-oxo-2,3-dihydro-1,3-benzothiazol-7-yl)ethyl]carbamate

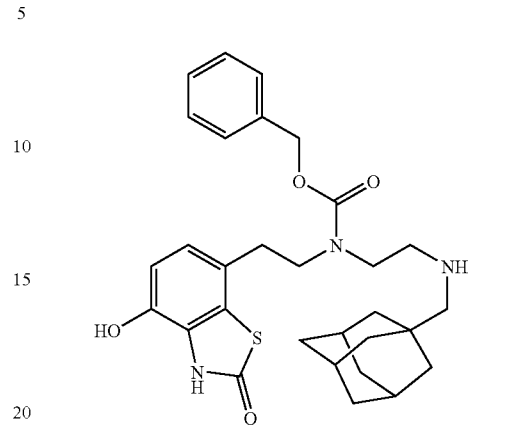

The aldehyde as prepared in Example 1 step ii) (2.7 g) was dissolved in THF (66.6 ml) and water (13.3 ml) was added, followed by 1-adamantanemethylamine (2.3 g), and then acetic acid (0.42 ml), and the mixture was stirred for 2 h. Sodium cyanoborohydride (0.88 g) was added and the mixture stirred at room temperature for 18 h. The mixture was diluted with ethyl acetate and washed with water, then brine, dried (anhydrous MgSO$_4$), filtered and evaporated. The residue was purified using adsorption, then elution from an SCX cartridge to give the sub-title compound (3 g).

MS (APCI+) 536 [M+H]$^+$ ii) N$^1$-(1-Adamantylmethyl)-N$^1$-(2-{[2-(4-hydroxy-2-oxo-2,3-dihydro-1,3-benzothiazol-7-yl)ethyl]amino}ethyl)-N$^3$-(2-phenylethyl)-β-alaninamide bis-trifluoroacetic acid salt

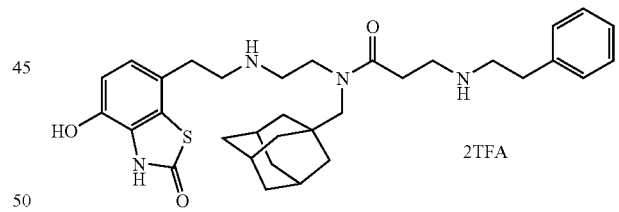

The amine as prepared in Example 59 step i) (0.8 g) was dissolved in dichloromethane (60 ml), chlorotrimethylsilane (0.54 g) and triethylamine (0.51 g) were added, and the mixture was stirred at room temperature for 90 min. The solution of acid chloride (1 eq) as prepared in Example 5 step ii) was added, and the mixture was stirred at room temperature for 3 h. Further portions of chlorotrimethylsilane (0.54 g) and triethylamine (0.81 g) were added, and the mixture was stirred at room temperature for 90 min. A further portion of the acid chloride solution (1 eq) was added, and the mixture was stirred at room temperature for 18 h. The solvents were removed in vacuo, and the residue was dissolved in ethyl acetate, washed with water, saturated sodium hydrogen carbonate solution, dilute aqueous HCl and brine, dried (anhydrous MgSO$_4$), filtered and evaporated. The residue was purified by flash chromatography on silica using ethyl acetate:isohexane (1:1) as eluent. The residue (0.18 g) was dissolved in acetic acid (3.6 ml) and hydrogen bromide 30 wt % solution in acetic acid (1.8 ml) was added, and the mixture was stirred at room temperature for 4 h. Methanol was added to give a clear solution and the mixture was purified using reverse phase HPLC (5-40% acetonitrile in aqueous TFA) to give the title compound (62 mg).

$^1$H NMR δ$_{(DMSO)}$ 7.35 (2H, t), 7.28 (3H, d), 6.88 (1H, d), 6.77 (1H, m), 3.58 (2H, m), 3.35 (8H, m), 3.04 (2H, s), 2.94 (2H, t), 2.82 (4H, m), 1.98 (2H, bs), 1.92 (1H, s), 1.69 (3H, t), 1.61 (3H, d), 1.53 (4H, s), 1.49 (2H, s).

MS (Multimode+) 577.2 [(M-salt)+H]$^+$

EXAMPLE 60

N$^1$-(1-Adamantylmethyl)-N$^3$-[2-(3-fluorophenyl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

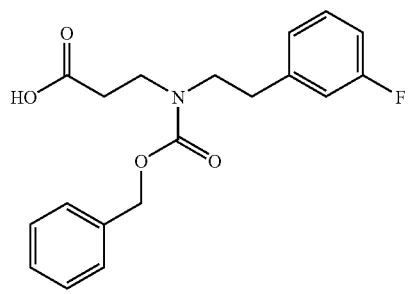

i) N-[(Benzyloxy)carbonyl]-N-[2-(3-fluorophenyl)ethyl]-β-alanine

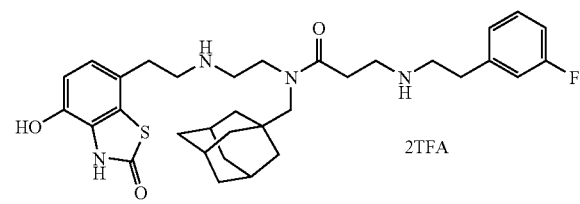

The sub-title compound was prepared by the method of Example 3 step i), using 3-fluorophenethylamine.

$^1$H NMR δ$_{(CDCl3)}$ 8.72 (1H, bs), 7.34 (3H, m), 7.20 (3H, m), 6.96-6.77 (3H, m), 5.15 (1H, bs), 5.10 (1H, bs), 3.82 (2H, d), 3.49 (4H, m), 2.58 (2H, d).

MS (APCI-) 344 [M-H]$^-$ ii) Benzyl (3-chloro-3-oxopropyl)[2-(3-fluorophenyl)ethyl]carbamate

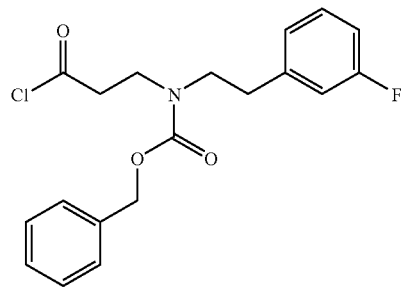

The sub-title compound was prepared by the method of Example 5 step ii), using the acid as prepared in example 60 step i). The product acid chloride was used directly in the next step.

iii) N$^1$-(1-Adamantylmethyl)-N$^3$-[2-(3-fluorophenyl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

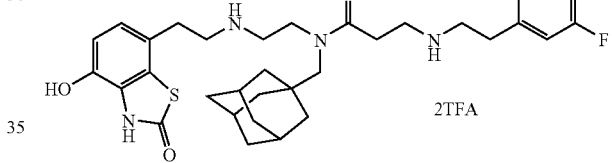

The title compound was prepared by the method of Example 59 step ii) using the acid chloride as prepared in Example 60 step ii), and adding an extra 1.3 equivalents of triethylamine with the first addition of the acid chloride.

$^1$H NMR δ$_{(DMSO)}$ 11.74 (1H, s), 10.15-10.13 (1H, 2×s), 7.38 (1H, m), 7.12 (3H, m), 6.86 (1H, dd), 6.75 (1H, dd), 3.58 (2H, s), 3.10 (12H, m), 2.81 (4H, m), 1.98 (2H, s), 1.92 (1H, s), 1.72-1.49 (12H, m).

MS (Multimode+) 595.3 [(M-salt)+H]$^+$

EXAMPLE 61

N$^1$-(1-Adamantylmethyl)-N$^3$-[2-(4-fluorophenyl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

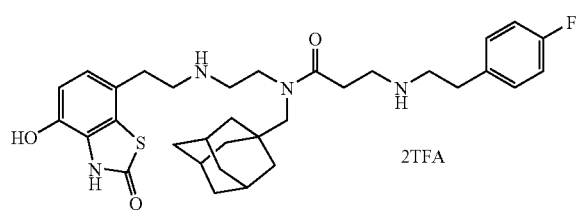

The title compound was prepared by the method of Example 60 using 4-fluorophenethylamine. No methanol was added prior to the HPLC purification.

$^1$H NMR $\delta_{(DMSO)}$ 11.74 (1H, s), 10.16-10.14 (1H, 2×s), 8.53-8.56 (3H, m), 7.31 (2H, m, 7.16 (2H, m), 6.86 (1H, d), 6.75 (1H, d), 3.58 (2H, m), 3.16 (9H, m), 3.04 (1H, s), 2.92 (2H, t), 2.81 (4H, m), 1.98 (2H, s), 1.93 (1H, s), 1.72-1.49 (12H, m).

MS (Multimode+) 595.2 [(M-salt)+H]$^+$

EXAMPLE 62

N$^1$-(2-{[2-(4-Hydroxy-2-oxo-2,3-dihydro-1,3-benzothiazol-7-yl)ethyl]amino}ethyl)-N$^3$-(2-phenylethyl)-N$^1$-(tetrahydro-2H-thiopyran-4-yl)-β-alaninamide bis-trifluoroacetic acid salt

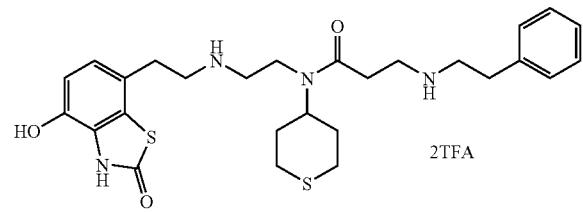

The title compound was prepared by the method of Example 6 steps iii) and iv) using tetrahydro-4H-thiopyran-4-one. In step iv) the material was azeotroped further with ethanol (×2) and acetonitrile (×2). The residue was dissolved in ethanol and treated with 10% palladium on carbon, and the mixture hydrogenated at 5 bar for 18 h. The catalyst was removed by filtration and the solvents were removed in vacuo. The residue was then purified according to step iv).

MS (Multimode+) 529.2 [(M-salt)+H]$^+$

EXAMPLE 63

N$^3$-[2-(3-Fluorophenyl)ethyl]-N$^1$-(2-{[2-(4-hydroxy-2-oxo-2,3-dihydro-1,3-benzothiazol-7-yl)ethyl]amino}ethyl)-N$^1$-(1-propylbutyl)-β-alaninamide bis-trifluoroacetic acid salt

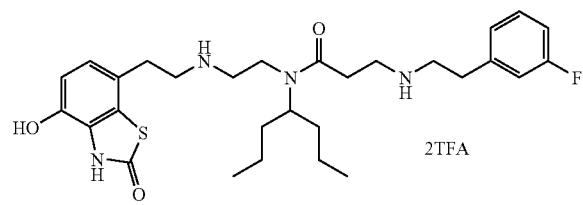

i) Benzyl [2-(4-hydroxy-2-oxo-2,3-dihydro-1,3-benzothiazol-7-yl)ethyl]{2-[(1-propylbutyl)amino]ethyl}carbamate

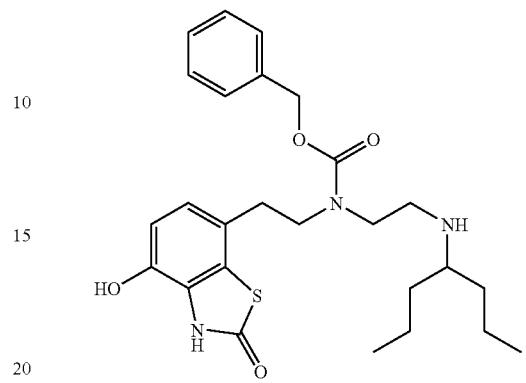

The sub-title compound was prepared by the method of Example 1 step iii) using 4-heptylamine. Acetic acid was added to the reaction and the mixture was stirred at room temperature for 30 min, before the addition of sodium cyanoborohydride. The reaction was stirred at room temperature overnight. After work up the residue was purified by flash chromatography on silica using ethyl acetate as eluent, followed by adsorption, then elution from an SCX cartridge. The residue was dissolved in ethyl acetate, washed with 0.25M aqueous HCl, then saturated sodium hydrogen carbonate solution, dried (anhydrous Na$_2$SO$_4$), filtered and evaporated.

$^1$H NMR $\delta_{(DMSO)}$ 7.41-7.27 (5H, m), 6.82-6.64 (2H, m), 5.10-4.99 (2H, m), 3.41 (2H, t), 3.20-3.07 (2H, m), 2.77-2.64 (2H, m), 2.58-2.52 (2H, m), 2.43-2.27 (1H, m), 1.35-1.13 (8H, m), 0.92-0.74 (6H, m).

MS (Multimode+) 486.2 [M+H]$^+$ ii) Benzyl {2-[acryloyl(1-propylbutyl)amino]ethyl} [2-(4-hydroxy-2-oxo-2,3-dihydro-1,3-benzothiazol-7-yl)ethyl]carbamate

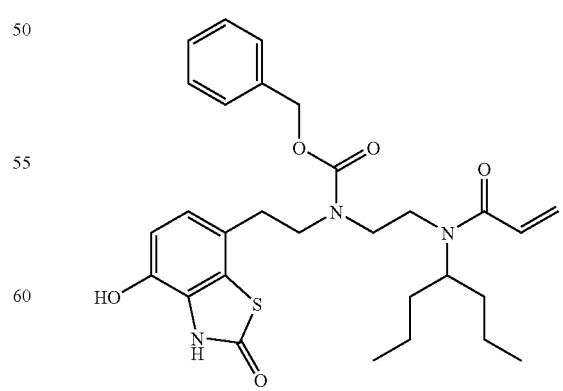

The amine as prepared in Example 63 step i) was reacted with 6 equivalents of triethylamine, 5 equivalents of chlorotrimethylsilane and 1.3 equivalents of acryloyl chloride using the method of Example 7 step i). The reaction mixture was washed with 2M aqueous HCl, rather than saturated sodium hydrogen carbonate, and ethyl acetate was the eluent for the flash chromatography purification, to give the sub-title compound.

$^1$H NMR $\delta_{(DMSO)}$ 11.69-11.55 (1H, m), 9.97-9.87 (1H, m), 7.46-7.27 (5H, m), 6.86-6.65 (2H, m), 6.45-6.37 (1H, m), 6.19-5.94 (2H, m), 5.71-5.57 (1H, m), 5.13-4.99 (2H, m), 4.47-4.25 (1H, m), 3.89-3.68 (1H, m), 3.51-3.37 (2H, m), 2.81-2.62 (2H, m), 1.49-0.94 (10H, m), 0.90-0.64 (6H, m).

MS (APCI+) 540 [M+H]$^+$ iii) $N^3$-[2-(3-Fluorophenyl)ethyl]-$N^1$-(2-{[2-(4-hydroxy-2-oxo-2,3-dihydro-1,3-benzothiazol-7-yl)ethyl]amino}ethyl)-$N^1$-(1-propylbutyl)-β-alaninamide bis-trifluoroacetic acid salt

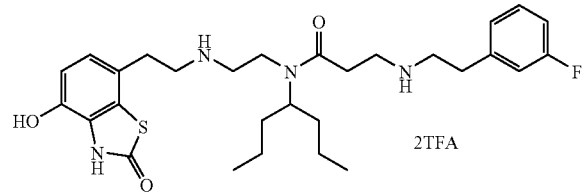

The title compound was prepared by the method of Example 7 step ii) using the acrylamide as prepared in Example 63 step ii) and 3-fluorophenethylamine. The reaction temperature was increased to 60° C., and the reaction was stirred for a further 24 h. The reaction volume was concentrated to ca. 3 ml, and the mixture was stirred at 60° C. for another 3 h. The reaction mixture was purified by adsorption, then elution from an SCX cartridge. The residue was dissolved in acetic acid rather than dichloromethane for the hydrogen bromide deprotection, and azeotroped with toluene before purification by reverse phase HPLC.

$^1$H NMR $\delta_{(DMSO)}$ 11.73 (1H, s), 10.17 (1H, s), 8.80-8.57 (2H, m), 7.43-7.34 (1H, m), 7.20-7.05 (3H, m), 6.87 (1H, d), 6.76 (1H, d), 3.69-3.58 (1H, m), 3.46-3.35 (2H, m), 3.31-3.12 (6H, m), 3.05-2.91 (4H, m), 2.88-2.70 (4H, m), 1.50-1.37 (4H, m), 1.31-1.11 (4H, m), 0.93-0.81 (6H, m).

MS (Multimode+) 545.2 [(M-salt)+H]$^+$

EXAMPLE 64

$N^3$-[2-(4-Fluorophenyl)ethyl]-$N^1$-(2-{[2-(4-hydroxy-2-oxo-2,3-dihydro-1,3-benzothiazol-7-yl)ethyl]amino}ethyl)-$N^1$-(1-propylbutyl)-β-alaninamide bis-trifluoroacetic acid salt

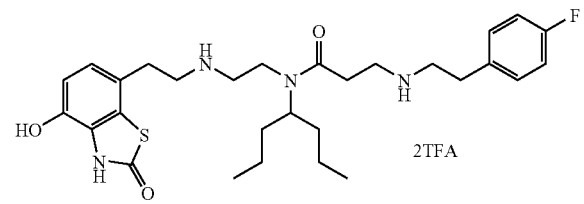

The title compound was prepared by the method of Example 63 step iii), using 4-fluorophenethylamine.

$^1$H NMR $\delta_{(DMSO)}$ 11.73 (1H, s), 10.15 (1H, s), 8.74-8.52 (2H, m), 7.34-7.28 (2H, m), 7.21-7.13 (2H, m), 6.87 (1H, d), 6.75 (1H, d), 3.71-3.32 (5H, m), 3.27-3.11 (4H, m), 3.03-2.89 (4H, m), 2.86-2.70 (4H, m), 1.50-1.37 (4H, m), 1.31-1.11 (4H, m), 0.93-0.81 (6H, m).

MS (Multimode+) 545.2 [(M-salt)+H]$^+$

EXAMPLE 65

$N^3$-[2-(2-Chlorophenyl)ethyl]-$N^1$-(3-hydroxy-2,2-dimethylpropyl)-$N^1$-(2-{[2-(4-hydroxy-2-oxo-2,3-dihydro-1,3-benzothiazol-7-yl)ethyl]amino}ethyl)-β-alaninamide bis-trifluoroacetic acid salt

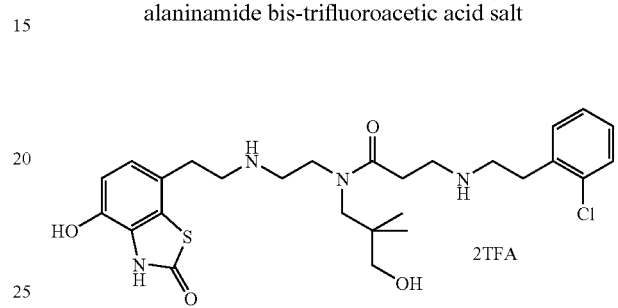

i) Benzyl {2-[acryloyl(3-hydroxy-2,2-dimethylpropyl)amino]ethyl}[2-(4-hydroxy-2-oxo-2,3-dihydro-1,3-benzothiazol-7-yl)ethyl]carbamate

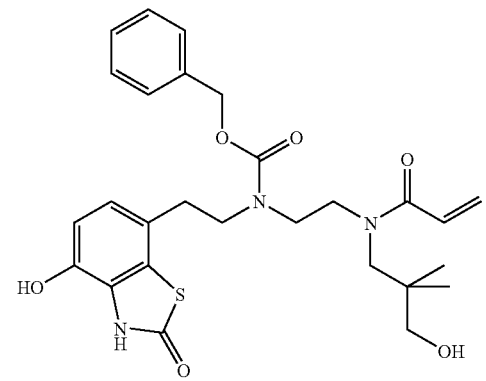

The amine as prepared in Example 39 step i) was reacted with 6 equivalents of triethylamine, 5 equivalents of chlorotrimethylsilane and 1.5 equivalents of acryloyl chloride using the method of Example 7 step i), allowing the reaction mixture to warm to room temperature overnight. The reaction mixture was washed with 2M aqueous HCl, rather than saturated sodium hydrogen carbonate. The residue was dissolved in a mixture of THF and water (10:3), and lithium hydroxide monohydrate (1.6 eq) was added, and the mixture stirred at room temperature for 2 h. Acetic acid (3.3 eq) was added and the reaction was evaporated to dryness. The orange residue was purified by flash column chromatography on silica using ethyl acetate:THF (1:1) plus a few drops of 880 ammonia to give the sub-title compound.

$^1$H NMR δ$_{(DMSO)}$ 7.46-7.22 (5H, m), 6.84-6.61 (2H, m), 6.17-5.96 (1H, m), 5.66-5.55 (1H, m), 5.44-5.35 (1H, m), 5.07-4.94 (2H, m), 3.67-2.89 (10H, m), 2.77-2.58 (2H, m), 0.78 (3H, s), 0.70 (3H, s).

MS (Multimode+) 528.2 [M+H]$^+$ ii) N$^3$-[2-(2-Chlorophenyl)ethyl]-N$^1$-(3-hydroxy-2,2-dimethylpropyl)-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

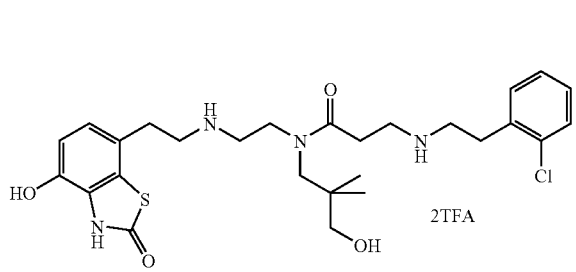

The title compound was prepared by the method of Example 7 step ii) using the acrylamide as prepared in Example 65 step i) and 2-chlorophenethylamine. After the hydrogen bromide deprotection the reaction mixture was treated with lithium hydroxide monohydrate (6 eq) in a mixture of methanol and water (2:1), and the mixture stirred at room temperature for 3 h. Excess acetic acid was added and the reaction mixture was stored in the freezer over the weekend. The solvents were removed in vacuo and the residue was treated with lithium hydroxide monohydrate (6 eq) in a mixture of methanol and water (2:1), and the mixture stirred at room temperature overnight. Excess acetic acid was added and the reaction mixture was evaporated to dryness, prior to purification by reverse phase HPLC (as Example 7 ii)).

$^1$H NMR δ$_{(DMSO)}$ 11.73 (1H, s), 10.12 (1H, s), 8.61 (2H, s), 7.50-7.28 (4H, m), 6.88-6.82 (1H, m), 6.78-6.72 (1H, m), 3.62-3.42 (12H, m), 3.20-3.09 (4H, m), 2.87-2.77 (4H, m), 0.90-0.79 (6H, m).

MS (Multimode+) 549.2 [(M-salt)+H]$^+$

EXAMPLE 66

N$^3$-[2-(3-Chlorophenyl)ethyl]-N$^1$-(3-hydroxy-2,2-dimethylpropyl)-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

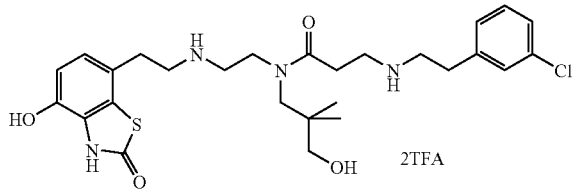

The title compound was prepared by the method of Example 65 step ii), using 3-chlorophenethylamine.

$^1$H NMR δ$_{(DMSO)}$ 11.74 (1H, s), 8.99-8.41 (4H, m), 7.47-7.17 (4H, m), 6.91-6.81 (1H, m), 6.80-6.71 (1H, m), 3.76-3.52 (12H, m), 3.26-3.08 (2H, m), 2.97-2.93 (2H, m), 2.87-2.79 (4H, m), 0.94-0.74 (6H, m).

MS (Multimode+) 549.2 [(M-salt)+H]$^+$

EXAMPLE 67

N$^3$-[2-(2,3-Dichlorophenyl)ethyl]-N$^1$-(3-hydroxy-2,2-dimethylpropyl)-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

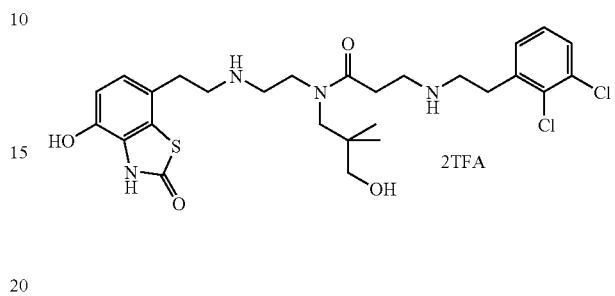

The title compound was prepared by the method of Example 65 step ii), using 2,3-dichlorophenethylamine.

$^1$H NMR δ$_{(DMSO)}$ 11.73 (1H, s), 9.00-8.51 (4H, m), 7.57 (1H, s), 7.37 (2H, s), 6.90-6.80 (1H, m), 6.80-6.71 (1H, m), 3.63-3.52 (2H, m), 3.34-3.01 (14H, m), 2.94-2.74 (4H, m), 0.94-0.74 (6H, m).

MS (Multimode+) 583.2 [(M-salt)+H]$^+$

EXAMPLE 68

N$^1$-Cyclohexyl-N$^1$-(2-{[2-(4-hydroxy-2-oxo-2,3-dihydro-1,3-benzothiazol-7-yl)ethyl]amino}ethyl)-N$^3$-[2-(4-methoxyphenyl)ethyl]-β-alaninamide bis-trifluoroacetic acid salt

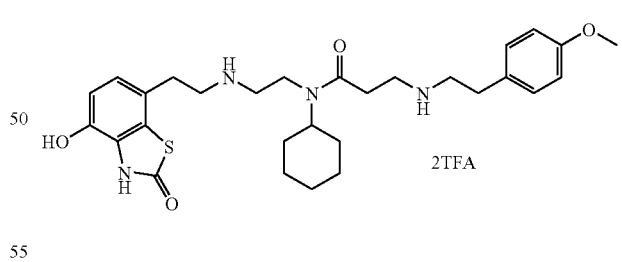

The title compound was prepared by the method of Example 7 step ii) using the acrylamide prepared as in Example 12 step i), and 4-methoxyphenethylamine.

$^1$H NMR δ$_{(DMSO)}$ 11.73 (1H, s), 10.17-10.12 (1H, m), 8.64-8.43 (4H, m), 7.21-7.16 (2H, m), 6.93-6.82 (3H, m), 6.78-6.73 (1H, m), 3.73 (3H, s), 3.55-3.44 (2H, m), 3.22-2.95 (9H, m), 2.90-2.76 (6H, m), 1.82-1.04 (10H, m).

MS (Multimode+) 541 [(M-salt)+H]$^+$

EXAMPLE 69

N³-{2-[4-(Aminosulfonyl)phenyl]ethyl}-N¹-cyclohexyl-N¹-(2-{[2-(4-hydroxy-2-oxo-2,3-dihydro-1,3-benzothiazol-7-yl)ethyl]amino}ethyl)-β-alaninamide bis-trifluoroacetic acid salt

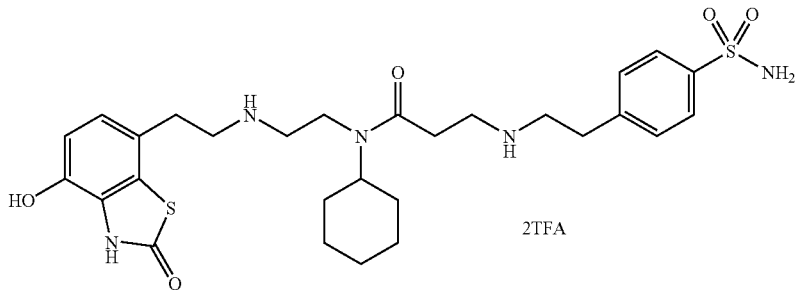

The title compound was prepared by the method of Example 7 step ii) using the acrylamide prepared as in Example 12 step i), and 4-(2-aminoethyl)benzenesulfonamide.

¹H NMR δ$_{(DMSO)}$ 11.73 (1H, s), 10.18-10.12 (1H, m), 8.91-8.53 (4H, m), 7.63 (4H, dd), 7.35 (2H, s), 6.89-6.83 (1H, m), 6.75 (1H, d), 3.59-3.10 (9H, m), 3.06-2.96 (4H, m), 2.87-2.77 (4H, m), 1.83-1.02 (10H, m).

MS (Multimode+) 590 [(M-salt)+H]⁺

EXAMPLE 70

N¹-Cyclohexyl-N¹-(2-{[2-(4-hydroxy-2-oxo-2,3-dihydro-1,3-benzothiazol-7-yl)ethyl]amino}ethyl)-N³-[2-(3-methoxyphenyl)ethyl]-β-alaninamide bis-trifluoroacetic acid salt

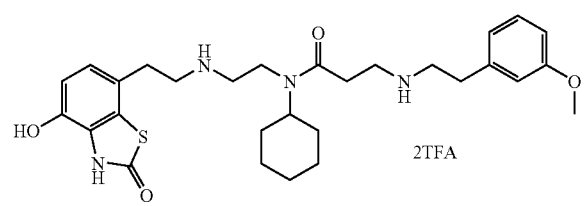

The title compound was prepared by the method of Example 7 step ii) using the acrylamide prepared as in Example 12 step i), and 2.5 equivalents of 3-methoxyphenethylamine.

¹H NMR δ$_{(DMSO)}$ 11.76-11.72 (1H, m), 10.17-10.13 (1H, m), 8.85-8.44 (4H, m), 7.26 (1H, t), 6.87-6.83 (4H, m), 6.75 (1H, d), 3.75 (3H, s), 3.58-3.10 (9H, m), 3.04-2.96 (2H, m), 2.93-2.87 (2H, m), 2.85-2.77 (4H, m), 1.82-1.22 (9H, m), 1.14-1.06 (1H, m).

MS (Multimode+) 541.2 [(M-salt)+H]⁺

EXAMPLE 71

N¹-Cyclohexyl-N¹-(2-{[2-(4-hydroxy-2-oxo-2,3-dihydro-1,3-benzothiazol-7-yl)ethyl]amino}ethyl)-N³-[2-(3-hydroxyphenyl)ethyl]-β-alaninamide bis-trifluoroacetic acid salt

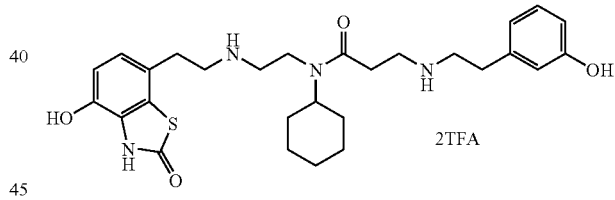

The title compound was prepared by the method of Example 7 step ii), using the acrylamide prepared as in Example 12 step i), and 2.5 equivalents of 3-hydroxyphenethylamine hydrochloride and adding 2.5 equivalents of triethylamine to the reaction mixture.

¹H NMR δ$_{(DMSO)}$ 11.73 (1H, s), 10.20-10.14 (1H, m), 9.48-9.40 (1H, m), 8.76-8.50 (4H, m), 7.11 (1H, t), 6.86 (1H, d), 6.75 (1H, d), 6.68-6.64 (3H, m), 3.58-3.44 (3H, m), 3.23-3.10 (6H, m), 3.04-2.97 (2H, m), 2.88-2.76 (6H, m), 1.81-1.22 (9H, m), 1.14-1.03 (1H, m).

MS (Multimode+) 527.4 [(M-salt)+H]⁺

EXAMPLE 72

N³-[2-(5-Chloro-2-thienyl)ethyl]-N¹-cyclohexyl-N¹-(2-{[2-(4-hydroxy-2-oxo-2,3-dihydro-1,3-benzothiazol-7-yl)ethyl]amino}ethyl)-β-alaninamide bis-trifluoroacetic acid salt

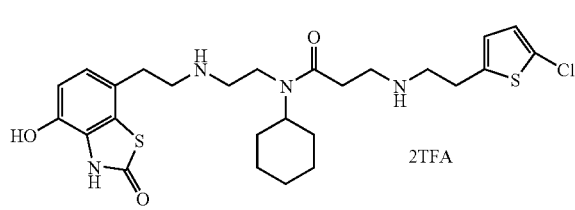

The title compound was prepared by the method of Example 71, using 2-(5-Chloro-2-thienyl)ethylamine hydrochloride.

$^{1}$H NMR $\delta_{(DMSO)}$ 11.79-11.72 (1H, m), 10.15-10.11 (1H, m), 8.61-8.40 (4H, m), 7.01 (1H, d), 6.89-6.84 (2H, m), 6.75 (1H, d), 3.59-3.07 (11H, m), 3.04-2.96 (2H, m), 2.86-2.75 (4H, m), 1.83-1.22 (9H, m), 1.15-1.02 (1H, m).

MS (Multimode+) 551 [(M-salt)+H]⁺

EXAMPLE 73

N¹-Cyclohexyl-N³-[2-(3,4-difluorophenyl)ethyl]-N¹-(2-{[2-(4-hydroxy-2-oxo-2,3-dihydro-1,3-benzothiazol-7-yl)ethyl]amino}ethyl)-β-alaninamide bis-trifluoroacetic acid salt

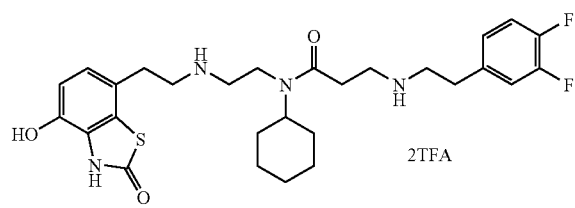

The title compound was prepared by the method of Example 71, using 3,4-difluorophenethylamine hydrochloride.

$^{1}$H NMR $\delta_{(DMSO)}$ 11.80-11.71 (1H, m), 10.11 (1H, s), 8.60-8.37 (4H, m), 7.46-7.36 (2H, m), 7.17-7.11 (1H, m), 6.88-6.84 (1H, m), 6.77-6.73 (1H, m), 3.58-3.10 (9H, m), 3.02-2.90 (4H, m), 2.84-2.75 (4H, m), 1.83-1.24 (9H, m), 1.15-1.01 (1H, m).

MS (Multimode+) 547.2 [(M-salt)+H]⁺

EXAMPLE 74

N¹-Cyclohexyl-N¹-(2-{[2-(4-hydroxy-2-oxo-2,3-dihydro-1,3-benzothiazol-7-yl)ethyl]amino}ethyl)-N³-[(2S)-2-hydroxy-2-phenylethyl]-β-alaninamide bis-trifluoroacetic acid salt

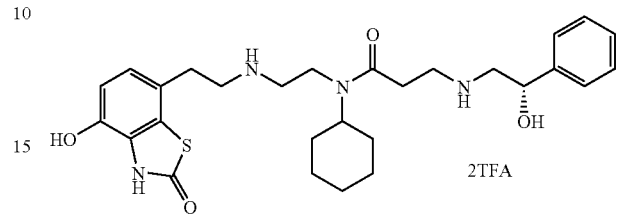

The acrylamide as prepared in Example 12 step i) (96 mg) was dissolved in ethanol (1.5 ml), (1S)-2-amino-1-phenylethanol (75 mg) was added and the mixture was stirred at 50° C. for 18 h. The solvents were removed in vacuo and the residue was re-dissolved in 98% formic acid (3 ml) and stirred vigorously under nitrogen. Palladium black was added in portions every 15 minutes (8×10 mg). The reaction was filtered, washed with formic acid (1 ml) and the filtrate stirred vigorously under nitrogen. Palladium black was added in portions every 15 minutes (6×10 mg). The reaction was filtered, and the solvents removed in vacuo. The residue was purified by adsorption, then elution from an SCX cartridge, followed by reverse phase HPLC (5-50% acetonitrile in aqueous TFA) to give the title compound (40 mg).

$^{1}$H NMR $\delta_{(DMSO)}$ 11.77-11.72 (1H, m), 10.15-10.10 (1H, m), 8.76-8.34 (4H, m), 7.42-7.31 (5H, m), 6.89-6.83 (1H, m), 6.78-6.73 (1H, m), 6.22 (1H, s), 4.93-4.86 (1H, m), 3.60-2.96 (11H, m), 2.88-2.77 (4H, m), 1.83-1.02 (10H, m).

MS (Multimode+) 527.2 [(M-salt)+H]⁺

EXAMPLE 75

N¹-Cyclohexyl-N¹-(2-{[2-(4-hydroxy-2-oxo-2,3-dihydro-1,3-benzothiazol-7-yl)ethyl]amino}ethyl)-N³-[(2R)-2-hydroxy-2-phenylethyl]-β-alaninamide bis-trifluoroacetic acid salt

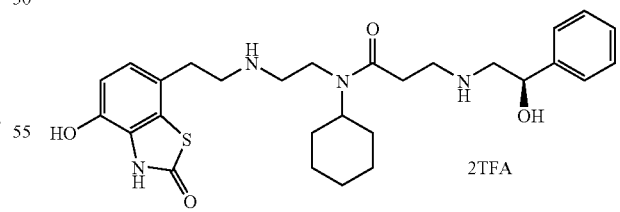

The title compound was prepared by the method of Example 74 using (1R)-2-amino-1-phenylethanol.

$^{1}$H NMR $\delta_{(DMSO)}$ 11.76-11.70 (1H, m), 10.18-10.12 (1H, m), 8.86-8.35 (4H, m), 7.43-7.29 (5H, m), 6.89-6.83 (1H, m), 6.78-6.73 (1H, m), 6.25-6.20 (1H, m), 4.95-4.86 (1H, m), 3.60-2.96 (11H, m), 2.89-2.77 (4H, m), 1.83-1.02 (10H, m).

MS (Multimode+) 527.2 [(M-salt)+H]⁺

EXAMPLE 76

N³-[2-(1,3-Benzodioxol-5-yl)ethyl]-N¹-cyclohexyl-N¹-(2-{[2-(4-hydroxy-2-oxo-2,3-dihydro-1,3-benzothiazol-7-yl)ethyl]amino}ethyl)-β-alaninamide bis-trifluoroacetic acid salt

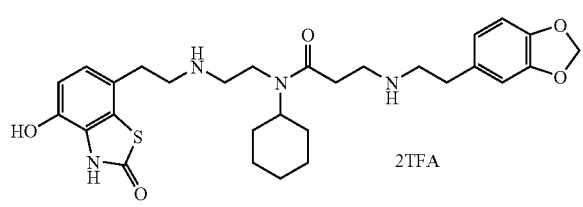

The title compound was prepared by the method of Example 7 step ii), using the acrylamide prepared as in Example 12 step i), and 3,4-methylenedioxyphenethylamine hydrochloride and adding 3 equivalents of triethylamine to the reaction mixture.

¹H NMR $\delta_{(DMSO)}$ 11.74 (1H, s), 10.17-10.11 (1H, m), 8.86-8.41 (4H, m), 6.89-6.82 (3H, m), 6.78-6.69 (2H, m), 5.99 (2H, s), 3.57-2.93 (11H, m), 2.89-2.71 (6H, m), 1.83-1.00 (10H, m).

MS (Multimode+) 555.2 [(M-salt)+H]⁺

EXAMPLE 77

N³-[2-(1H-Benzimidazol-2-yl)ethyl]-N¹-cyclohexyl-N¹-(2-{[2-(4-hydroxy-2-oxo-2,3-dihydro-1,3-benzothiazol-7-yl)ethyl]amino}ethyl)-β-alaninamide tris-trifluoroacetic acid salt

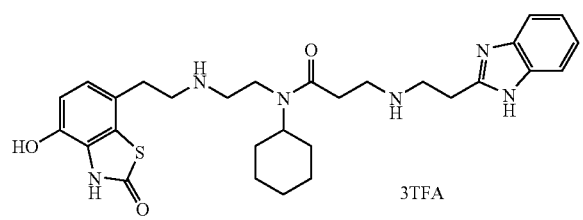

The title compound was prepared by the method of Example 7 step ii), using the acrylamide prepared as in example 12 step i), and 1H-benzimidazole-2-ethanamide dihydrochloride, and adding 3 equivalents of triethylamine to the reaction mixture. The reaction was incomplete after 18 h at 50° C., so a further 3 equivalents of triethylamine were added, and the mixture was stirred at 70° C. for 18 h. The reaction mixture was purified by adsorption, then elution from an SCX cartridge, prior to reverse phase HPLC.

¹H NMR $\delta_{(DMSO)}$ 11.74 (1H, s), 10.14 (1H, s), 8.85-8.53 (2H, m), 7.58 (2H, dd), 7.24 (2H, dd), 6.85 (1H, d), 6.76 (1H, q), 3.62-3.42 (5H, m), 3.34-3.21 (4H, m), 3.19-3.06 (2H, m), 3.05-2.95 (2H, m), 2.89-2.75 (4H, m), 1.83-1.01 (10H, m).

MS (Multimode+) 551.2 [(M-salt)+H]⁺

EXAMPLE 78

N¹-Cyclohexyl-N³-[2-(3,5-difluorophenyl)ethyl]-N¹-(2-{[2-(4-hydroxy-2-oxo-2,3-dihydro-1,3-benzothiazol-7-yl)ethyl]amino}ethyl)-β-alaninamide bis-trifluoroacetic acid salt

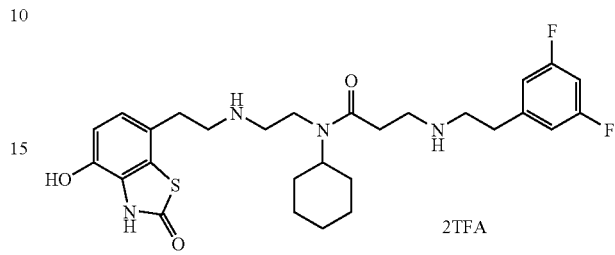

The title compound was prepared by the method of Example 76, using 3,5-difluorophenethylamine hydrochloride.

¹H NMR $\delta_{(DMSO)}$ 11.73 (1H, s), 10.17-10.11 (1H, m), 8.85-8.48 (4H, m), 7.18-7.02 (3H, m), 6.88-6.83 (1H, m), 6.75 (1H, d), 3.59-3.10 (9H, m), 3.04-2.94 (4H, m), 2.86-2.76 (4H, m), 1.83-1.02 (10H, m).

MS (Multimode+) 547.2 [(M-salt)+H]⁺

EXAMPLE 79

N¹-Cyclohexyl-N³-[2-(2,5-difluorophenyl)ethyl]-N¹-(2-{[2-(4-hydroxy-2-oxo-2,3-dihydro-1,3-benzothiazol-7-yl)ethyl]amino}ethyl)-β-alaninamide bis-trifluoroacetic acid salt

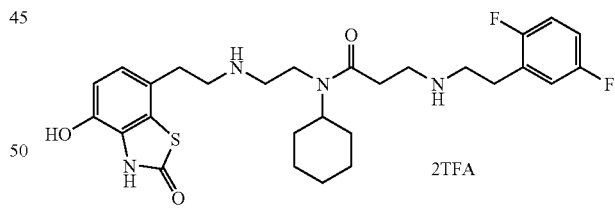

The title compound was prepared by the method of Example 76, using 2,5-difluorophenethylamine hydrochloride. The reaction mixture was purified by adsorption, then elution from an SCX cartridge, prior to reverse phase HPLC.

¹H NMR $\delta_{(DMSO)}$ 11.74 (1H, s), 10.14-10.10 (1H, m), 8.74-8.48 (4H, m), 7.31-6.95 (3H, m), 6.88-6.84 (1H, m), 6.78-6.73 (1H, m), 3.59-3.10 (9H, m), 3.04-2.94 (4H, m), 2.85-2.76 (4H, m), 1.82-1.01 (10H, m).

MS (Multimode+) 547.2 [(M-salt)+H]⁺

EXAMPLE 80

N¹-Cyclohexyl-N¹-(2-{[2-(4-hydroxy-2-oxo-2,3-dihydro-1,3-benzothiazol-7-yl)ethyl]amino}ethyl)-N³-(3,3,3-trifluoropropyl)-β-alaninamide bis-trifluoroacetic acid salt

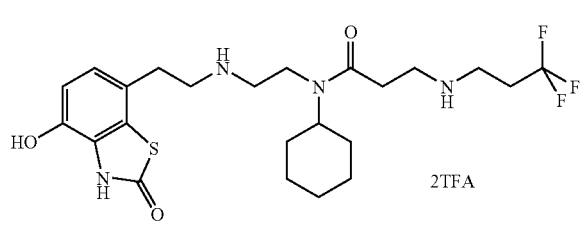

The title compound was prepared by the method of Example 76, using 3,3,3-trifluoropropylamine hydrochloride.

¹H NMR $\delta_{(DMSO)}$ 11.73 (1H, s), 10.17-10.12 (1H, m), 8.83-8.56 (4H, m), 6.89-6.83 (1H, m), 6.78-6.73 (1H, m), 3.59-3.06 (9H, m), 3.04-2.96 (2H, m), 2.87-2.65 (6H, m), 1.82-1.01 (10H, m).

MS (Multimode+) 503.2 [(M-salt)+H]⁺

EXAMPLE 81

N¹-Cyclohexyl-N³-[2-(2,3-difluorophenyl)ethyl]-N¹-(2-{[2-(4-hydroxy-2-oxo-2,3-dihydro-1,3-benzothiazol-7-yl)ethyl]amino}ethyl)-β-alaninamide bis-trifluoroacetic acid salt

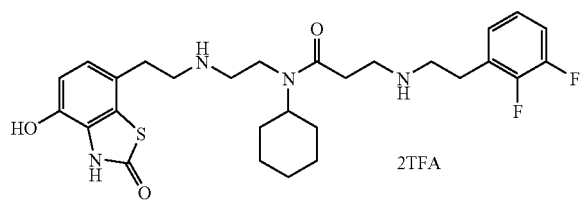

The title compound was prepared by the method of Example 7 step ii), using the acrylamide prepared as in Example 12 step i), and 2,3-difluorophenethylamine. The reaction mixture was purified by adsorption, then elution from an SCX cartridge, prior to reverse phase HPLC.

¹H NMR $\delta_{(DMSO)}$ 11.73 (1H, s), 10.16-10.11 (1H, m), 8.83-8.54 (4H, m), 7.40-7.32 (1H, m), 7.24-7.16 (2H, m), 6.89-6.83 (1H, m), 6.78-6.73 (1H, m), 3.59-3.10 (9H, m), 3.08-2.96 (4H, m), 2.86-2.76 (4H, m), 1.82-1.02 (10H, m).

MS (Multimode+) 547.2 [(M-salt)+H]⁺

EXAMPLE 82

N¹-Cycloheptyl-N¹-(2-{[2-(4-hydroxy-2-oxo-2,3-dihydro-1,3-benzothiazol-7-yl)ethyl]amino}ethyl)-N³-{2-[3-(trifluoromethyl)phenyl]ethyl}-β-alaninamide bis-trifluoroacetic acid salt

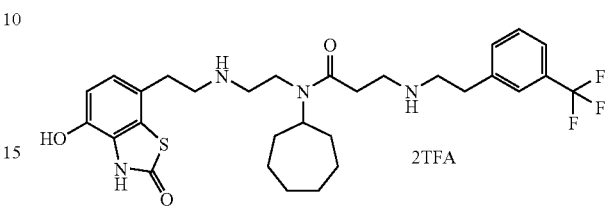

The title compound was prepared by the method of Example 36, using 2-(3-trifluoromethylphenyl)ethylamine.

¹H NMR $\delta_{(DMSO)}$ 7.62-7.55 (4H, m), 6.85 (1H, d), 6.75 (1H, d), 3.72-3.67 (1H, m), 3.47 (2H, t), 3.30-2.82 (14H, m), 1.76-1.46 (12H, m).

MS (Multimode+) 593.2 [(M-salt)+H]⁺

EXAMPLE 83

N¹-Cycloheptyl-N³-[2-(2,5-difluorophenyl)ethyl]-N¹-(2-{[2-(4-hydroxy-2-oxo-2,3-dihydro-1,3-benzothiazol-7-yl)ethyl]amino}ethyl)-β-alaninamide bis-trifluoroacetic acid salt

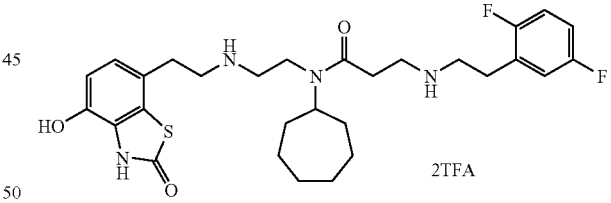

The title compound was prepared by the method of Example 54, using 2,5-difluorophenethylamine hydrochloride.

¹H NMR $\delta_{(DMSO)}$ 11.73 (1H, s), 10.14 (1H, s), 8.64 (4H, s), 7.27 (2H, m), 7.17 (1H, m), 6.87 (1H, m), 6.75 (1H, m), 3.68 (1H, m), 3.46 (2H, t), 3.17 (6H, m), 3.05 (2H, s), 2.98 (2H, t), 2.82 (4H, m), 1.75-1.60 (8H, m), 1.47 (4H, m).

MS (Multimode+) 561.2 [(M-salt)+H]⁺

EXAMPLE 84

N$^1$-Cycloheptyl-N$^3$-[2-(2,6-difluorophenyl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

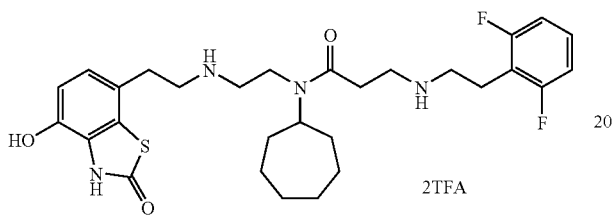

The title compound was prepared by the method of Example 54, using 2,6-difluorophenethylamine hydrochloride.

$^1$H NMR δ$_{(DMSO)}$ 11.75 (1H, m), 10.14 (1H, m), 8.67 (4H, m), 7.40 (1H, m), 7.13 (2H, m), 6.87 (1H, m), 6.76 (1H, m), 3.68 (1H, m), 3.46 (2H, t), 3.19 (6H, m), 3.03 (4H, m), 2.82 (4H, m), 1.76-1.60 (8H, m), 1.48 (4H, m).
MS (Multimode+) 561.2 [(M-salt)+H]$^+$

EXAMPLE 85

N$^1$-Cycloheptyl-N$^1$-(2-{[2-(4-hydroxy-2-oxo-2,3-dihydro-1,3-benzothiazol-7-yl)ethyl]amino}ethyl)-N$^3$-[2-(3-methylphenyl)ethyl]-β-alaninamide bis-trifluoroacetic acid salt

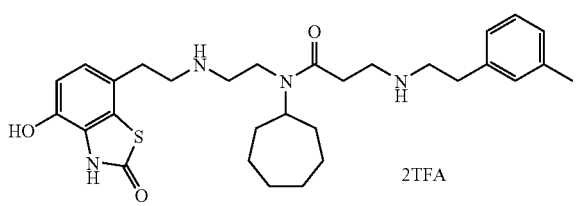

The title compound was prepared by the method of Example 36, using 3-methylphenethylamine. The residue was dissolved in acetic acid rather than dichloromethane for the hydrogen bromide deprotection.

$^1$H NMR δ$_{(DMSO)}$ 11.74 (1H, m), 10.14 (1H, m), 8.63 (2H, s), 8.52 (2H, s), 7.23 (1H, m), 7.07 (3H, m), 6.87 (1H, m), 6.75 (1H, m), 3.68 (1H, m), 3.46 (2H, t), 3.19 (6H, m), 3.05 (2H, s), 2.89 (2H, m), 2.82 (4H, m), 2.29 (3H, s), 1.75-1.60 (8H, m), 1.48 (4H, m).

MS (Multimode+) 539.2 [(M-salt)+H]$^+$

EXAMPLE 86

N$^1$-Cycloheptyl-N$^3$-[2-(3,4-dimethoxyphenyl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

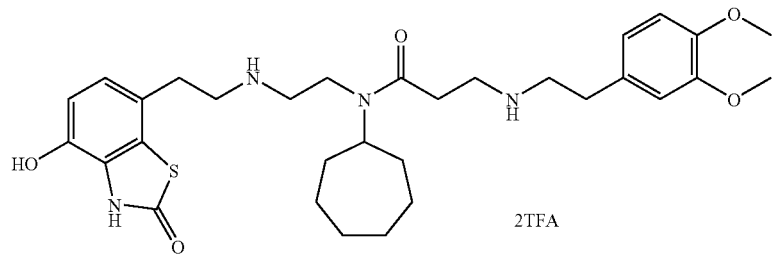

The title compound was prepared by the method of Example 85, using 3,4-dimethoxyphenethylamine.
$^1$H NMR δ$_{(DMSO)}$ 11.73 (1H, s), 10.15 (1H, m), 8.64 (2H, s), 8.48 (2H, s), 6.91-6.85 (3H, m), 6.79-6.74 (2H, m), 3.75 (3H, s), 3.72 (3H, s), 3.68 (1H, m), 3.45 (2H, m), 3.18 (6H, m), 3.05 (2H, m), 2.84 (6H, m), 1.72-1.60 (8H, m), 1.47 (4H, m).
MS (Multimode+) 585.2 [(M-salt)+H]$^+$

EXAMPLE 87

N$^1$-Cycloheptyl-N$^3$-[2-(4-hydroxy-2-oxo-2,3-dihydro-1,3-benzothiazol-7-yl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

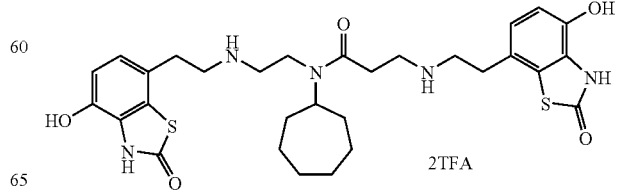

The title compound was prepared by the method of Example 54, using 7-(2-aminoethyl)-4-hydroxy-1,3-benzothiazol-2(3H)-one hydrobromide.

$^1$H NMR $\delta_{(DMSO)}$ 6.89 (2H, m), 6.78 (2H, m), 3.68 (1H, m), 3.46 (2H, t), 3.16 (6H, m), 3.06 (2H, t), 2.84 (6H, m), 1.75-1.60 (8H, m), 1.48 (4H, m).

MS (Multimode+) 614.2 [(M-salt)+H]$^+$

EXAMPLE 88

N$^1$-Cycloheptyl-N$^3$-[2-(2,3-dihydro-1,4-benzodioxin-6-yl)ethyl]-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

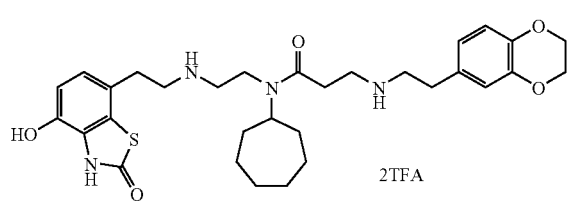

The title compound was prepared by the method of Example 85, using 2-(2,3-dihydro-1,4-benzodioxin-6-yl) ethylamine.

$^1$H NMR $\delta_{(DMSO)}$ 6.89 (1H, m), 6.77 (4H, m), 4.21 (4H, s), 3.67 (1H, m), 3.45 (2H, t), 3.16 (6H, m), 3.05 (2H, t), 2.82 (6H, m), 1.75-1.60 (8H, m), 1.48 (4H, m).

MS (Multimode+) 583.2 [(M-salt)+H]$^+$

EXAMPLE 89

N$^3$-[2-(3-chloro-4-hydroxyphenyl)ethyl]-N$^1$-cyclohexyl-N$^1$-(2-{[2-(4-hydroxy-2-oxo-2,3-dihydro-1,3-benzothiazol-7-yl)ethyl]amino}ethyl)-β-alaninamide bis-trifluoroacetic acid salt

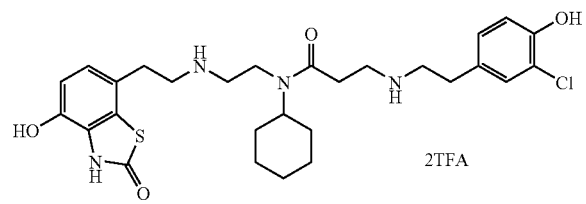

The title compound was prepared by the method of example 7 step ii), using 3-chloro-4-hydroxyphenethylamine and adding 2 equivalents of triethylamine to the reaction mixture. The residue was dissolved in glacial acetic acid rather than dichloromethane for the hydrogen bromide deprotection.

$^1$H NMR $\delta_{(DMSO)}$ 11.75-11.72 (1H, m), 10.18-10.10 (2H, m), 8.87-8.42 (4H, m), 7.27-7.24 (1H, m), 7.03 (1H, dd), 6.92 (1H, d), 6.86 (1H, d), 6.78-6.73 (1H, m), 3.60-3.43 (3H, m), 3.22-3.10 (6H, m), 3.04-2.96 (2H, m), 2.86-2.76 (6H, m), 1.82-1.02 (10H, m).

MS (Multimode+) 561.2 [(M-salt)+H]$^+$

EXAMPLE 90

N$^1$-Cyclooctyl-N$^1$-(2-{[2-(4-hydroxy-2-oxo-2,3-dihydro-1,3-benzothiazol-7-yl)ethyl]amino}ethyl)-N$^3$-[2-(3-hydroxyphenyl)ethyl]-β-alaninamide bis-trifluoroacetic acid salt

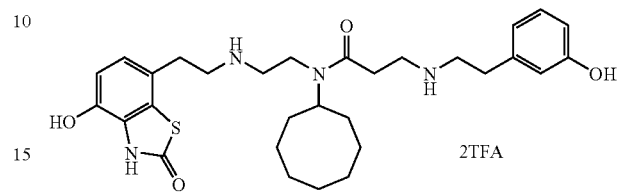

i) Benzyl [2-(cyclooctylamino)ethyl][2-(4-hydroxy-2-oxo-2,3-dihydro-1,3-benzothiazol-7-yl)ethyl]carbamate

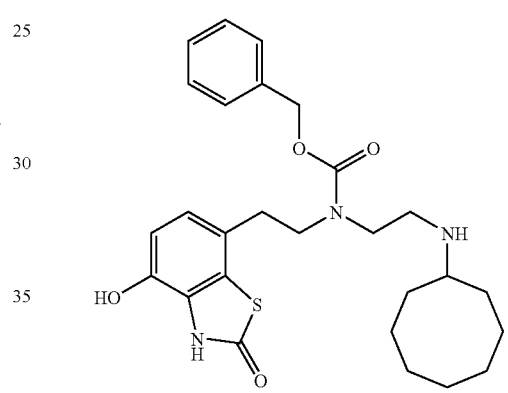

The sub-title compound was prepared by the method of Example 1 step iii) using cyclooctylamine.

$^1$H NMR $\delta_{(DMSO)}$ 7.35 (5H, m), 6.74 (2H, m), 5.06 (2H, m), 3.42 (2H, t), 3.38-3.17 (2H, m), 2.90 (1H, m), 2.73 (4H, m), 1.78-1.30 (14H, m).

MS (APCI+) 498 [M+H]$^+$ ii) Benzyl {2-[acryloyl(cyclooctyl)amino]ethyl}[2-(4-hydroxy-2-oxo-2,3-dihydro-1,3-benzothiazol-7-yl)ethyl]carbamate

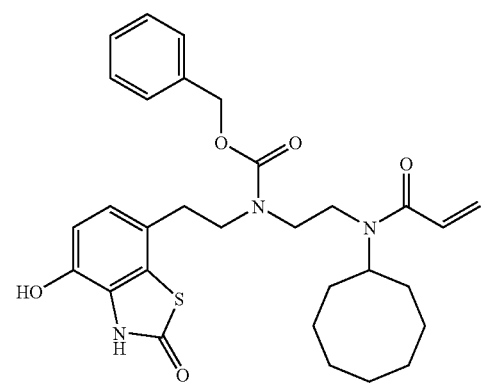

The amine as prepared in example 90 step i) (0.2 g) was dissolved in THF (10 ml), N,N-diisopropylethylamine (0.28 ml) and chlorotrimethylsilane (0.107 ml) were added, and the mixture was stirred at room temperature for 1 h. Acryloyl chloride was added and the mixture was stirred at room temperature for 20 h. The reaction mixture was diluted with water, extracted with ethyl acetate, washed with water and brine, dried (anhydrous $Na_2SO_4$), filtered and evaporated to give the sub-title compound.

$^1$H NMR $\delta_{(DMSO)}$ 7.43-7.32 (5H, m), 6.77 (1H, m), 6.70 (1H, m), 6.40-5.25 (3H, m), 5.08 (2H, s), 3.42 (2H, m), 3.30 (2H, m), 3.24 (1H, m), 3.15 (1H, m), 3.05 (1H, m), 2.71 (2H, m), 1.73-0.83 (14H, m).

MS (APCI+) 552.2 [M+H]$^+$ iii) N$^1$-Cyclooctyl-N$^1$-(2-{[2-(4-hydroxy-2-oxo-2,3-dihydro-1,3-benzothiazol-7-yl)ethyl]amino}ethyl)-N$^3$-[2-(3-hydroxyphenyl)ethyl]-β-alaninamide bis-trifluoroacetic acid salt

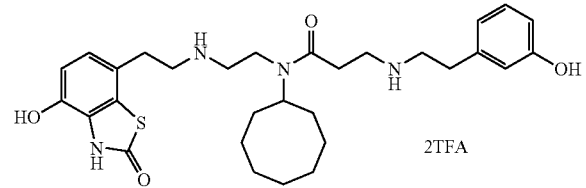

The title compound was prepared by the method of example 7 step ii), using 2 equivalents of 3-hydroxyphenethylamine hydrochloride, 5 equivalents of triethylamine, and heating the reaction mixture to 60° C. for 48 h. The residue was dissolved in glacial acetic acid rather than dichloromethane for the hydrogen bromide deprotection.

$^1$H NMR $\delta_{(DMSO)}$ 11.74 (1H, s), 10.13 (1H, s), 9.43 (1H, s), 8.59 (2H, s), 8.44 (2H, s), 7.12 (1H, m), 6.86 (1H, m), 6.75 (1H, m), 6.67 (3H, m), 3.76 (1H, m), 3.49-3.33 (2H, m), 3.16 (6H, m), 3.06 (2H, m), 2.82 (6H, m), 1.79-1.43 (14H, m).

MS (Multimode+) 555.2 [(M-salt)+H]$^+$

EXAMPLE 91

N$^1$-(4,4-Dimethylcyclohexyl)-N$^1$-(2-{[2-(4-hydroxy-2-oxo-2,3-dihydro-1,3-benzothiazol-7-yl)ethyl]amino}ethyl)-N$^3$-[2-(3-hydroxyphenyl)ethyl]-β-alaninamide bis-trifluoroacetic acid salt

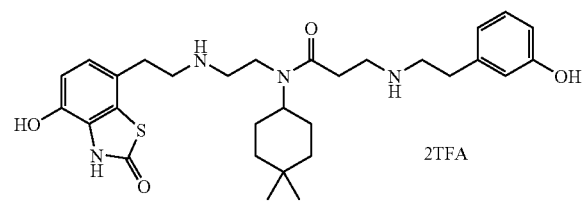

i) Benzyl {2-[(4,4-dimethylcyclohexyl)amino]ethyl} [2-(4-hydroxy-2-oxo-2,3-dihydro-1,3-benzothiazol-7-yl)ethyl]carbamate

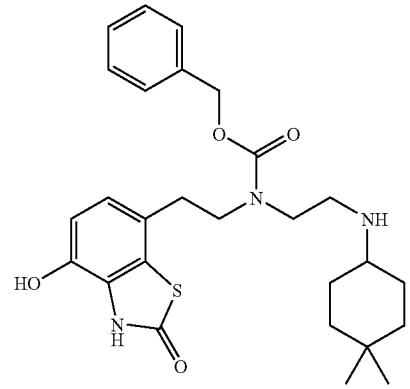

The sub-title compound was prepared by the method of example 1 step iii) using 1.5 equivalents of 4,4-dimethylcyclohexylamine hydrochloride and adding 1.5 equivalents of sodium hydrogen carbonate. The mixture was stirred overnight. After work up the residue was purified by flash column chromatography on silica using 10% 1M methanolic ammonia in dichloromethane to give the sub-title compound.

$^1$H NMR $\delta_{(DMSO)}$ 7.41-7.30 (5H, m), 6.81-6.67 (2H, m), 5.07 (2H, m), 3.60 (2H, m), 3.42 (2H, t), 2.95-2.75 (1H, m), 2.75-2.66 (2H, m), 1.76 (2H, m), 1.72 (1H, m), 1.64 (1H, m), 1.42-1.06 (6H, m), 0.87 (6H, m).

MS (APCI+) 498 [M+H]$^+$ ii) Benzyl {2-[acryloyl(4,4-dimethylcyclohexyl)amino]ethyl}[2-(4-hydroxy-2-oxo-2,3-dihydro-1,3-benzothiazol-7-yl)ethyl]carbamate

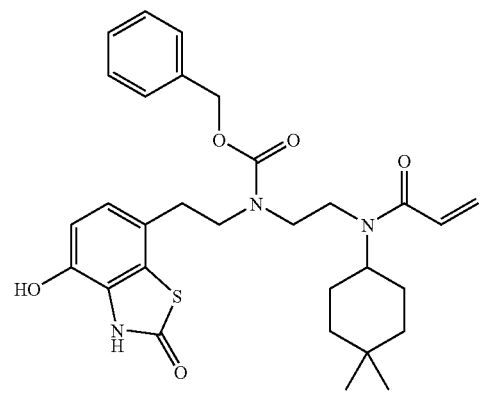

The sub-title compound was prepared by the method of Example 90 step ii) using the amine as prepared in Example 91 step i).

$^1$H NMR $\delta_{(DMSO)}$ 7.36 (5H, m), 7.24 (1H, m), 7.16 (1H, m), 6.82-6.63 (2H, m), 6.18-5.95 (1H, m), 5.08 (2H, m), 3.52-2.97 (7H, m), 2.68 (2H, m), 1.70-1.01 (8H, m), 0.88 (6H, m).

MS (APCI+) 552.2 [M+H]$^+$ iii) N¹-(4,4-Dimethylcyclohexyl)-N¹-(2-{[2-(4-hydroxy-2-oxo-2,3-dihydro-1,3-benzothiazol-7-yl)ethyl]amino}ethyl)-N³-[2-(3-hydroxyphenyl)ethyl]-β-alaninamide bis-trifluoroacetic acid salt

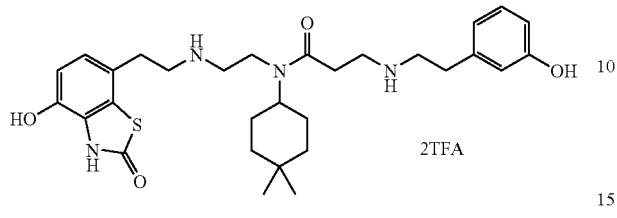

The title compound was prepared by the method of Example 90 step iii) using the acrylamide as prepared in Example 91 step ii).

$^1$H NMR $\delta_{(DMSO)}$ 11.73 (1H, s), 10.12 (1H, s), 9.41 (1H, s), 8.57 (2H, s), 8.44 (2H, s), 7.12 (1H, m), 6.86 (1H, m), 6.75 (1H, m), 6.66 (3H, m), 3.50 (3H, m), 3.16 (6H, m), 3.01 (2H, m), 2.81 (6H, m), 1.64 (2H, m), 1.46 (4H, m), 1.32 (2H, m), 0.95 (3H, s), 0.91 (3H, s).

MS (Multimode+) 555.2 [(M-salt)+H]⁺

EXAMPLE 92

N-Cyclohexyl-N³-[2-(3,5-difluorophenyl)ethyl]-N-(2-{[2-(4-hydroxy-2-oxo-2,3-dihydro-1,3-benzothiazol-7-yl)ethyl]amino}ethyl)-β-alaninamide dihydrobromide salt i) Benzyl [2-(cyclohexyl{N-[2-(3,5-difluorophenyl)ethyl]-β-alanyl}amino)ethyl][2-(4-hydroxy-2-oxo-2,3-dihydro-1,3-benzothiazol-7-yl)ethyl]carbamate

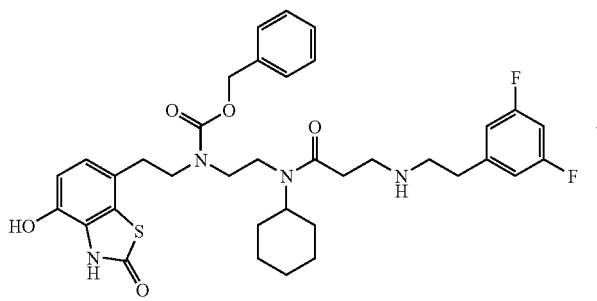

Benzyl {2-[acryloyl(cyclohexyl)amino]ethyl}[2-(4-hydroxy-2-oxo-2,3-dihydro-1,3-benzothiazol-7-yl)ethyl]carbamate prepared as in Example 12 step i) (0.33 g), triethylamine (0.176 mL) and 3,5-difluorophenethylamine hydrochloride (0.244 g) were stirred in ethanol (3 mL) at 60° C. for 44 h. The mixture was cooled to room temperature, quenched with water (30 mL), extracted with ethyl acetate (50 mL), the organic extracts washed with brine, dried (Na₂SO₄), filtered and evaporated in vacuo. The residue was purified by flash silica chromatography with 10% methanol/dichloromethane as eluent. The pure fractions were evaporated to dryness to afford the sub-title product (0.35 g) as a colourless gum.

MS: APCI (+ve): 681 [M+H]⁺ ii) N-Cyclohexyl-N³-[2-(3,5-difluorophenyl)ethyl]-N-(2-{[2-(4-hydroxy-2-oxo-2,3-dihydro-1,3-benzothiazol-7-yl)ethyl]amino}ethyl)-β-alaninamide dihydrobromide salt

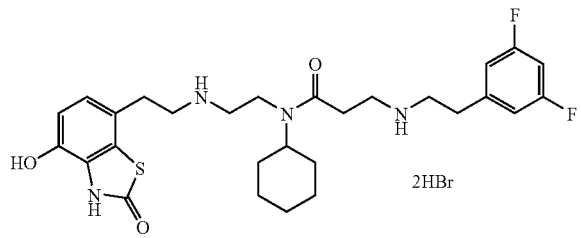

Hydrogen bromide/acetic acid (33%, 2 mL) was added to a solution of the carbamate of step i) (0.350 g) in acetic acid (2 mL) and the reaction was stirred for 1 h. The solution was diluted with t-butyl methyl ether (20 mL) and the resulting precipitate filtered off, washed with more t-butyl methyl ether (10 mL) and dried to afford a peach coloured solid. The solid was slurried in ethanol (7.5 mL), filtered off and dried to yield the title product (0.22 g) as a white solid.

$^1$H NMR $\delta_{(DMSO)}$ 10.07 (1H, s), 7.14 (1H, m), 7.07 (2H, m), 6.88 (1H, m), 6.75 (1H, m), 3.55 (1H, m), 3.48 (2H, m), 3.29 (2H, m), 3.15 (4H, m), 3.00 (4H, m), 2.83 (4H, m), 1.79 (2H, m), 1.70 (2H, m), 1.63 (1H, m), 1.56-1.23 (4H, m), 1.10 (1H, m)

EXAMPLE 93

N-Cyclohexyl-N³-[2-(2,3-difluorophenyl)ethyl]-N-(2-{[2-(4-hydroxy-2-oxo-2,3-dihydro-1,3-benzothiazol-7-yl)ethyl]amino}ethyl)-β-alaninamide dihydrobromide salt i) Benzyl [2-(cyclohexyl{N-[2-(2,3-difluorophenyl)ethyl]-β-alanyl}amino)ethyl][2-(4-hydroxy-2-oxo-2,3-dihydro-1,3-benzothiazol-7-yl)ethyl]carbamate

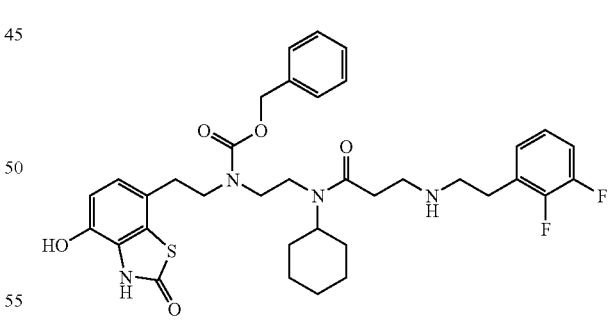

Benzyl 2-(N-cyclohexylacrylamido)ethyl(2-(4-hydroxy-2-oxo-2,3-dihydrobenzo[d]thiazol-7-yl)ethyl)carbamate prepared as in Example 12 step i) (0.33 g), 2,3-difluorophenethylamine hydrochloride (0.244 g) and triethylamine (0.176 mL) were dissolved in ethanol (3 mL) and heated at 60° C. for 48 h. The mixture was cooled to room temperature, quenched with water, extracted with ethyl acetate, washed with water and brine, dried (Na₂SO₄), filtered and evaporated in vacuo to afford the sub-title product (0.420 g) as a light brown gum.

MS: APCI (+ve): 681 [M+H]⁺ ii) N-Cyclohexyl-N³-[2-(2,3-difluorophenyl)ethyl]-N-(2-{[2-(4-hydroxy-2-oxo-2,3-dihydro-1,3-benzothiazol-7-yl)ethyl]amino}ethyl)-β-alaninamide dihydrobromide salt

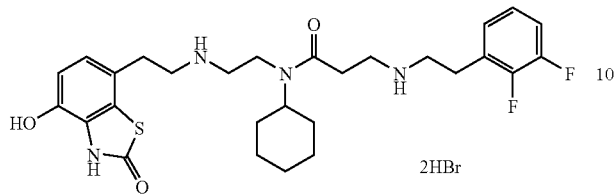

A solution of the carbamate from step (i) (0.4 g) in acetic acid (2 mL) was treated with hydrogen bromide/acetic acid (33%, 2 mL) and stirred for 1 h. Toluene (10 mL) was added, the mixture was evaporated in vacuo, the residue purified by reverse phase HPLC with 0.2% aqueous TFA/acetonitrile as eluent and the pure fractions evaporated in vacuo. The solid residue was dissolved in a mixture of ethanol (5 mL) and acetonitrile (15 mL) and treated with hydrobromic acid in aqueous acetonitrile (16%, 1.8 mL). A solid gradually precipitated and was filtered off, washed with acetonitrile and slurried in ethanol. The solid was filtered off, washed with a little ethanol and dried to afford the title product (0.036 g) as a white solid.

¹H NMR δ$_{(DMSO)}$ 10.07 (1H, s), 8.49 (4H, m), 7.36 (1H, m), 7.21 (2H, m), 6.88 (1H, m), 6.76 (1H, m), 3.52 (3H, m), 3.28-2.95 (6H, m), 3.14 (2H, m), 3.03 (4H, m), 2.82 (2H, m), 1.79 (2H, m), 1.70 (2H, m), 1.63 (1H, m), 1.47 (2H, m), 1.33 (2H, m), 1.09 (1H, m)

MS: APCI (+ve): 547 [M+H]⁺

EXAMPLE 94

N³-[2-(3,4-Dichlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide dihydrobromide salt i) Benzyl 3-chloro-3-oxopropyl(3,4-dichlorophenethyl)carbamate

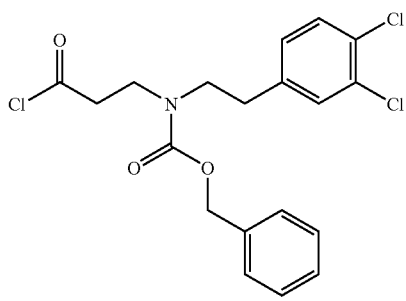

3-((Benzyloxycarbonyl)(3,4-dichlorophenethyl)amino)propanoic acid (0.5 g), prepared according to the procedure of Example 1 step iv), but using 2,3-dichlorophenethylamine instead of phenethylamine, was dissolved in dichloromethane (10 mL) and treated with oxalyl chloride (0.132 mL) and DMF (0.05 mL). The reaction was stirred at room temperature until gas evolution ceased, and the solvent was removed in vacuo to give an oil which was used in step ii) directly.

ii) Benzyl {2-[{N-[(benzyloxy)carbonyl]-N-[2-(3,4-dichlorophenyl)ethyl]-β-alanyl}(tetrahydro-2H-pyran-4-yl)amino]ethyl}[2-(4-hydroxy-2-oxo-2,3-dihydro-1,3-benzothiazol-7-yl)ethyl]carbamate

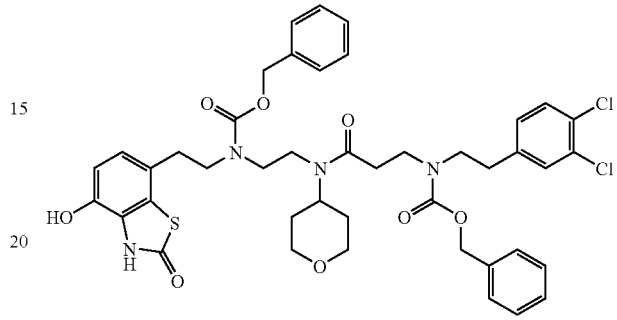

To an ice cooled suspension of benzyl 2-(4-hydroxy-2-oxo-2,3-dihydrobenzo[d]thiazol-7-yl)ethyl(2-(tetrahydro-2H-pyran-4-ylamino)ethyl)carbamate (2.5 g), as prepared as in Example 23 step i), in dichloromethane (40 mL) was added triethylamine (2.95 mL) followed by chlorotrimethylsilane (2.69 mL). The reaction was allowed to stir for 30 min before a solution of the acid chloride of step i) (2.198 g) in dichloromethane (20 mL) was added. The reaction was stirred for 2 h before the mixture was diluted with dichloromethane (200 mL), washed with water (150 mL) and saturated sodium hydrogen carbonate (150 mL), and the organic layer was dried over sodium sulphate, filtered and evaporated to afford crude product. This was purified by flash silica chromatography eluting with ethyl acetate. Pure fractions were evaporated to dryness to afford the sub-title product (3.10 g) as a off-white foam.

¹H NMR 90° C. δ$_{(DMSO)}$ 7.43 (1H, d), 7.39 (1H, s), 7.35-7.26 (10H, m), 7.13 (1H, d), 6.72 (1H, d), 6.67 (1H, d), 5.06-5.00 (4H, m), 3.84-3.78 (2H, m), 3.50-3.14 (13H, m), 2.82-2.77 (2H, m), 2.73-2.67 (2H, m), 2.58-2.53 (2H, m), 1.68-1.58 (2H, m), 1.44-1.36 (2H, m)

iii) N³-[2-(3,4-Dichlorophenyl)ethyl]-N-(2-{[2-(4-hydroxy-2-oxo-2,3-dihydro-1,3-benzothiazol-7-yl)ethyl]amino}ethyl)-N-(tetrahydro-2H-pyran-4-yl)-β-alaninamide dihydrobromide salt

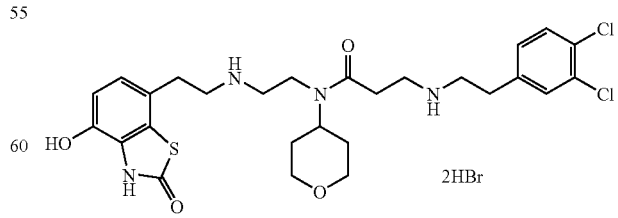

To a solution of product of step ii) (1 g) in acetic acid (5 mL) was added hydrogen bromide 33% solution in acetic acid (5 mL). The reaction was stirred at room temperature for 2.5 h. The reaction mixture was mixed with toluene and evaporated to give a foam. More toluene was added and evaporated to give a solid. The solid was recrystallised from ethanol to give a white solid which was dried overnight at 50° C. under vacuum to give the title product (370 mg).

$^1$H NMR $\delta_{(DMSO)}$ 11.81-11.65 (1H, m), 10.06 (1H, m), 8.81-8.38 (4H, m), 7.58-7.53 (2H, m), 7.30 (1H, dd), 6.89 (1H, d), 6.77 (1H, d), 3.95-3.90 (3H, m), 3.57 (2H, d), 3.46-3.37 (2H, m), 3.29-3.13 (6H, m), 3.10-3.01 (4H, m), 2.98-2.89 (4H, m), 1.84-1.61 (4H, m)

| CHNS | Requires | C: 43.62% | H: 4.88% | N: 7.54% | S: 4.31% |
|---|---|---|---|---|---|
| | Found | C: 42.64% | H: 4.77% | N: 7.59% | S: 4.30% |

EXAMPLE 95

N-Cycloheptyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide dihydromide salt i) Benzyl [2-(cycloheptyl{N-[2-(3-fluorophenyl)ethyl]-β-alanyl}amino)ethyl][2-(4-hydroxy-2-oxo-2,3-dihydro-1,3-benzothiazol-7-yl)ethyl]carbamate

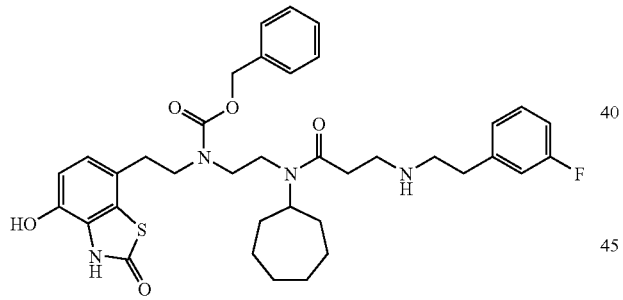

2-(3-Fluorophenyl)ethanamine (0.573 mL) was added to benzyl {2-[acryloyl(cycloheptyl)amino]ethyl}[2-(4-hydroxy-2-oxo-2,3-dihydro-1,3-benzothiazol-7-yl)ethyl]carbamate, prepared as in Example 23 step ii), (0.786 g) in ethanol (15 mL). The resulting solution was stirred at 50° C. for 32 h. The volatiles were removed in vacuo and the crude material was purified by flash silica chromatography, elution gradient 0.5:0.5:19 to 1:7:13 7M NH$_3$ in methanol:ethanol:ethyl acetate. Pure fractions were evaporated to dryness to afford the sub-title product (0.759 g) as a pale yellow foam.

$^1$H NMR 90° C. $\delta_{(DMSO)}$ δ 7.38-7.24 (6H, m), 7.03-6.98 (2H, m), 6.93 (1H, td), 6.74 (1H, d), 6.68 (1H, d), 5.07 (2H, s), 3.72-3.64 (1H, m), 3.44 (2H, t), 3.23-2.71 (14H, m), 1.61-1.36 (12H, m)

MS: APCI (+ve): 677 [M+H]$^+$ ii) N-Cycloheptyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide dihydromide salt

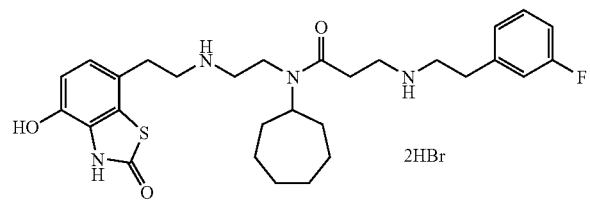

Hydrogen bromide (33% in acetic acid) (2.031 mL) was added to the product from step i) (0.759 g) in acetic acid (3 mL) at 0° C. The resulting solution was stirred at room temperature for 2 h, then t-butyl methyl ether (10 mL) was added and the mixture stirred for 10 min. A gummy solid formed, which was filtered off and triturated with t-butyl methyl ether (4×5 mL) to form a very pale orange solid (0.888 g), which was recrystallised from hot ethanol (~12 mL). White crystals were allowed to form over 4 h, which were filtered off and dried to give the title product (0.475 g).

$^1$H NMR 90° C. $\delta_{(DMSO)}$ 7.37 (1H, q), 7.14-7.10 (2H, m), 7.07-7.03 (1H, m), 6.88 (1H, d), 6.75 (1H, d), 3.74-3.68 (1H, m), 3.53-3.49 (2H, m), 3.28-2.84 (14H, m), 1.78-1.46 (12H, m)

EXAMPLE 96

N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide dihydrobromide salt i) Benzyl {3-[cyclohexyl(2,2-dimethoxyethyl)amino]-3-oxopropyl}[2-(3-fluorophenyl)ethyl]carbamate

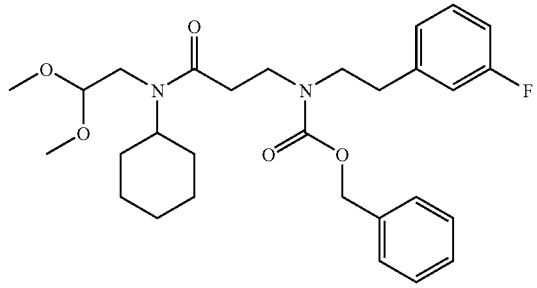

To a solution of N-[(benzyloxy)carbonyl]-N-[2-(3-fluorophenyl)ethyl]-β-alanine (5 g), prepared according to the procedure of Example 1 step iv) but using 3-fluorophenethylamine instead of phenethylamine, dissolved in dichloromethane (50 mL) with stirring under nitrogen was added dimethylformamide (2 drops) followed by oxalyl chloride (1.64 mL) dropwise over 10 min. The mixture was stirred at room temperature for 1 h, concentrated in vacuo and redissolved in dichloromethane (25 mL). The solution was added dropwise to a preformed mixture of N-(2,2-dimethoxyethyl)cyclohexanamine (2.71 g) and triethylamine (3.0 mL) in dichloromethane (25 mL) at 0° C. under nitrogen. The mixture was stirred at 0° C. for 1 h, then water (25 mL) was added and the layers were separated. The organic layer was washed with 2M hydrochloric acid, saturated aqueous sodium bicarbonate and brine before being dried (MgSO$_4$) filtered and concentrated to give the sub-title compound (7.45 g) as an oil.

$^1$H NMR $\delta_{(DMSO)}$ 7.35 (5H, s), 7.25-7.15 (1H, m), 7.02-6.76 (3H, m), 5.12 (2H, d), 4.62-4.52 (1H, m), 4.39-4.26 (0.5H, m), 4.23-4.09 (0.5H, m), 3.59-3.46 (4H, m), 3.38 (6H, s), 3.35-3.23 (2H, m), 2.92-2.45 (4H, m), 1.88-0.99 (10H, m)

MS: APCI (+ve): 515 [M+H]$^+$ ii) Benzyl {3-[cyclohexyl(2-{[2-(4-hydroxy-2-oxo-2,3-dihydro-1,3-benzothiazol-7-yl)ethyl]amino}ethyl)amino]-3-oxopropyl}[2-(3-fluorophenyl)ethyl]carbamate

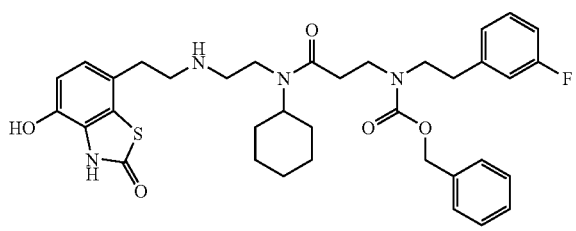

para-Toluenesulfonic acid monohydrate (10.4 g) was added to a solution of the product from step i) (9.4 g) in dichloromethane (94 mL). The mixture was stirred at room temperature for 40 min and a solution of saturated aqueous sodium bicarbonate (4.6 g) in water (100 mL) was added. The layers were separated and the organic phase was washed with saturated aqueous sodium bicarbonate (50 mL) and water (50 mL) before being dried (MgSO$_4$), filtered and concentrated. The resulting oil was redissolved in N-methylpyrrolidinone (30 mL) and added to a solution of 7-(2-aminoethyl)-4-hydroxy-1,3-benzothiazol-2(3H)-one hydrobromide (6.0 g) and triethylamine (2.9 mL) in N-methylpyrrolidinone (30 mL) and water (3 mL). Sodium triacetoxyborohydride (6.0 g) was added and the mixture was stirred at room temperature for 3 h before being poured into water (600 mL) and extracted with ethyl acetate (2×150 mL). The organic layer was washed with aqueous sodium chloride (100 mL). A solid precipitated from the organic layer, which was partially concentrated in vacuo, and the precipitate was collected by filtration and washed with ethyl acetate to give the sub-title compound (7.7 g) as a colourless solid.

$^1$H NMR $\delta_{(DMSO)}$ δ 7.41-7.24 (5H, m), 7.10-6.93 (3H, m), 6.86 (1H, d), 6.77 (1H, m), 5.05 (2H, d), 3.63-3.26 (8H, m), 3.13-3.01 (2H, m), 2.99-2.76 (6H, m), 2.62-2.52 (1H, m), 1.79-0.95 (10H, m)

MS: APCI (+ve): 663 [M+H]$^+$ iii) N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide dihydrobromide salt

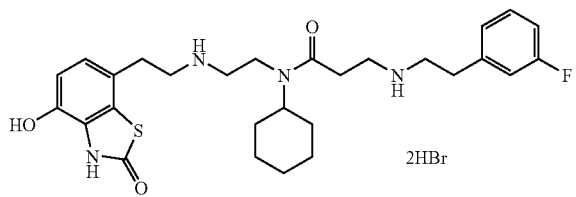

To a solution of the product from step ii) (1 g) in acetic acid (3 mL) stirred at room temperature was added hydrobromic acid in acetic acid (33%, 3 mL). The mixture was stirred for 80 min and then tert-butyl methyl ether (8 mL) was added. The mixture was stirred for 5 min and then filtered, washing with t-butyl methyl ether (8 mL). Purification by recrystallisation from hot ethanol (20 mL) gave the title compound (0.82 g) as a solid.

$^1$H NMR $\delta_{(DMSO)}$ 11.72 (1H, s), 10.08 (1H, s), 8.60 (4H, s), 7.39 (1H, q), 7.22-7.03 (3H, m), 6.88 (1H, d), 6.81-6.72 (1H, m), 3.65-3.47 (3H, m), 3.32-3.08 (6H, m), 3.07-2.95 (4H, m), 2.94-2.81 (4H, m), 1.76 (3H, t), 1.68-1.22 (5H, m), 1.19-1.02 (2H, m)

MS: APCI (+ve): 529 [M+H]$^+$

EXAMPLE 97

N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide di-D-mandelate salt A portion of the dihydrobromide from Example 96 was suspended in tetrahydrofuran and water (5:1), treated with a solution of saturated aqueous sodium bicarbonate (3 mol eq) in water, and the mixture stirred for 15 min. The tetrahydrofuran was removed in vacuo, sodium chloride was added, and the mixture was extracted with chloroform. The combined organic fractions were washed with water and brine, dried (Na$_2$SO$_4$), filtered and treated with a solution of D-mandelic acid (3 mol eq) in acetonitrile (40 mL). The mixture was stirred for 2 h, filtered, washed with acetonitrile and dried to give the title compound as a colourless solid.

¹H NMR δ(DMSO) 7.40 (4H, d), 7.38-7.14 (7H, m), 7.05 (3H, t), 6.82-6.67 (2H, m), 4.75-4.69 (2H, m), 4.10-3.97 (0.5H, m), 3.53-3.44 (0.5H, m), 3.35-3.22 (2H, m), 3.07-2.97 (4H, m), 2.92-2.73 (6H, m), 2.72-2.61 (4H, m), 1.78-1.69 (2H, m), 1.65-1.55 (2H, m), 1.52-1.17 (5H, m), 1.13-1.00 (1H, m)

MS: APCI (+ve): 529 [M+H]⁺

EXAMPLE 98

N-Cycloheptyl-N-(2-{[2-(4-hydroxy-2-oxo-2,3-dihydro-1,3-benzothiazol-7-yl)ethyl]amino}ethyl)-N³-(2-phenylethyl)-β-alaninamide dihydrobromide salt i) Benzyl {3-[(2-{[(benzyloxy)carbonyl][2-(4-hydroxy-2-oxo-2,3-dihydro-1,3-benzothiazol-7-yl)ethyl]amino}ethyl)(cycloheptyl)amino]-3-oxopropyl}(2-phenylethyl)carbamate

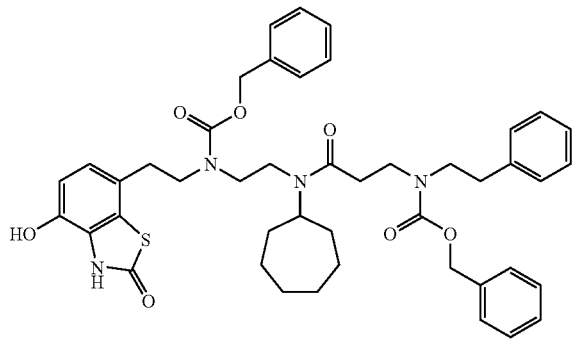

Chlorotrimethylsilane (1.323 mL) was added to a cooled (0° C.) solution of benzyl 2-(cycloheptylamino)ethyl(2-(4-hydroxy-2-oxo-2,3-dihydrobenzo[d]thiazol-7-yl)ethyl)carbamate, prepared as in Example 23 step i) (1.260 g) and triethylamine (1.81 mL) in dichloromethane (35 mL). The reaction mixture was stirred at room temperature for 2 h then a solution of benzyl 3-chloro-3-oxopropyl(phenethyl)carbamate, prepared as in Example 5 step ii) (0.991 g) in dichloromethane (10 mL) was added. The reaction mixture was stirred at room temperature for 4 h then diluted with ethyl acetate and washed with 2M hydrochloric acid (×2) and saturated sodium hydrogen carbonate. The organic layer was separated, washed with water and saturated brine, dried over sodium sulphate, filtered and evaporated. The crude product was purified by flash silica chromatography (Biotage), elution gradient 1 to 6% methanol in dichloromethane. Fractions containing product were evaporated to dryness to afford the product as a yellow foam (1.416 g). The material was used in the next step directly.

ii) N-Cycloheptyl-N-(2-{[2-(4-hydroxy-2-oxo-2,3-dihydro-1,3-benzothiazol-7-yl)ethyl]amino}ethyl)-N³-(2-phenylethyl)-β-alaninamide dihydrobromide salt

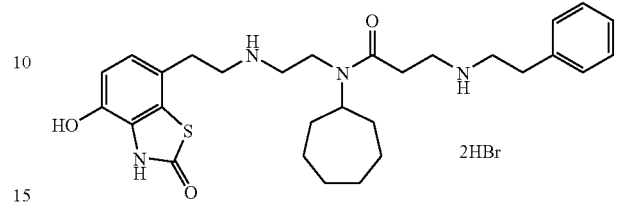

Hydrogen bromide (33% in acetic acid) (0.54 mL) was added to the product from step i) (0.238 g) in acetic acid (0.8 mL) at 0° C. The resulting solution was stirred at room temperature for 2 h then t-butyl methyl ether (3 mL) was added and the mixture stirred for 10 min. A gummy solid formed, which was filtered off and triturated with t-butyl methyl ether (4×3 mL) to form a pale orange solid (0.888 g). The solid was dried at 45° C. for 1 h then recrystallised from hot ethanol (~3 mL) to afford the title product as a white solid (0.040 g).

¹H NMR δ(DMSO) 11.74 (1H, s), 10.10-10.08 (1H, m), 8.72-8.39 (4H, m), 7.38-7.25 (5H, m), 6.91-6.86 (1H, m), 6.77-6.74 (1H, m), 3.73-3.65 (1H, m), 3.49-2.80 (16H, m), 1.80-1.46 (12H, m)

MS: APCI (+ve): 525 [M+H]⁺

EXAMPLE 99

N-Cycloheptyl-N-(2-{[2-(4-hydroxy-2-oxo-2,3-dihydro-1,3-benzothiazol-7-yl)ethyl]amino}ethyl)-N³-(2-phenylethyl)-β-alaninamide dibenzoate salt A portion of the dihydrobromide prepared according to Example 98 was suspended in tetrahydrofuran and water (5:1), treated with a solution of saturated aqueous sodium bicarbonate (3 mol eq) in water, and the mixture stirred for 30 min. The mixture was diluted with 2-methyl tetrahydrofuran and the aqueous layer separated. The organic layer was evaporated and the residue was dissolved in 2-methyl tetrahydrofuran, washed with water, dried over sodium sulphate and evaporated. The residual solid was slurried with acetonitrile for 24 h, and the solid free base collected by filtration.

The solid free base was dissolved in methanol and treated with benzoic acid (2.1 mol eq). The resulting solution was heated to 45° C. and diluted with acetonitrile whereupon an oil was precipitated. A seed of di-benzoate was added and the mixture was heated at 45° C. for ~1 h. A thick precipitate formed which was stirred at room temperature for 2 days. The solid was collected by filtration, washed with ice-cold MeCN/ 10% MeOH and dried in vacuo at 40° C. for 2 h to give the title compound as a colourless solid.

$^1$H NMR $\delta_{(DMSO)}$ 7.93 (4H, d), 7.53-49 (2H, m), 7.41 (4H, m), 7.29-7.22 (5H, m), 6.82 (2H, m), 6.71 (2H, m), 4.0 (0.5H, m), 3.65 (0.5H, m), 3.27 (2H, m), 2.98 (2H, m), 2.9-2.6 (6H, m), 2.51-2.49 (6H, m), 1.69-1.41 (6H, m)

MS: APCI (+ve): 525 [M+H]$^+$

EXAMPLE 100

N-Benzyl-4-[2-({3-[cycloheptyl(2-{[2-(4-hydroxy-2-oxo-2,3-dihydro-1,3-benzothiazol-7-yl)ethyl] amino}ethyl)amino]-3-oxopropyl}amino)ethyl]benzamide bis-trifluoroacetic acid salt

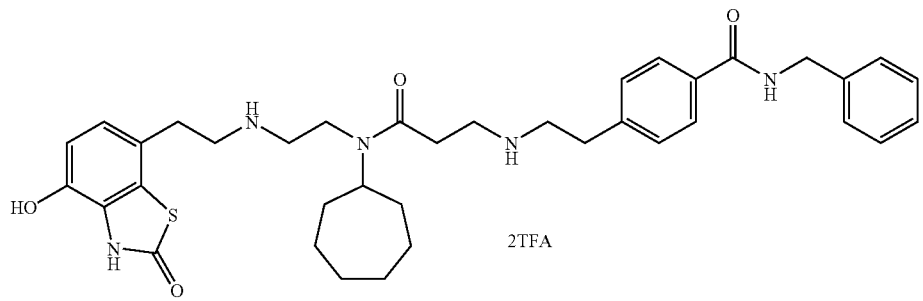

i) 4-(2-tert-Butoxycarbonylaminoethyl)benzoic acid

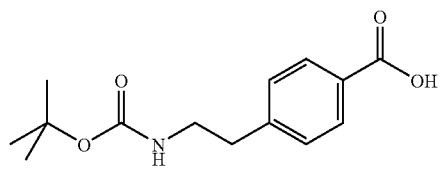

A solution of sodium hydroxide (0.398 g) in water (5 mL) was added to a stirred suspension of 4-(2-aminoethyl)-benzoic acid hydrochloride (0.822 g) in 1,4-dioxane (10 mL). After the mixture had become homogeneous it was cooled (0° C.) and Boc-anhydride (1.196 g) was added. The reaction mixture was stirred at room temperature for 18 h then partially concentrated in vacuo and diluted with ethyl acetate. 2M Aqueous hydrochloric acid was added until the solution was at pH 1 then the layers were separated and the aqueous layer extracted with further ethyl acetate. The combined organic extracts were washed with saturated aqueous sodium bicarbonate, water, saturated aqueous sodium chloride, than dried (Na$_2$SO$_4$) and the volatiles evaporated to afford a white solid (0.762 g) which was used in the next step without further purification.

$^1$H NMR $\delta_{(DMSO)}$ 7.85 (2H, d), 7.30 (2H, d), 6.89 (1H, t), 3.16 (2H, q), 2.76 (2H, t), 1.35 (9H, s).

ii) [2-(4-Benzylcarbamoylphenyl)ethyl]carbamic acid tert-butyl ester

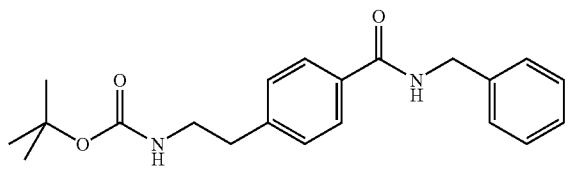

4-(2-tert-Butoxycarbonylaminoethyl)benzoic acid (0.307 g) was dissolved in methanol (5 mL) and treated with diethylisopropylamine (0.605 mL) and benzylamine (0.379 mL). The mixture was cooled (0° C.) then HATU (1.32 g) was added in portions. The reaction mixture was stirred for 48 h at room temperature, then partially concentrated in vacuo and partitioned between 2M aqueous hydrochloric acid and ethyl acetate. The organic layer was washed with further aqueous hydrochloric acid, saturated aqueous sodium bicarbonate, water, saturated aqueous sodium chloride, then dried (Na$_2$SO$_4$) and concentrated to afford a colourless oil (>0.41 g) which was used in the next step without further purification.

iii) 4-(2-Aminoethyl)-N-benzylbenzamide hydrochloride

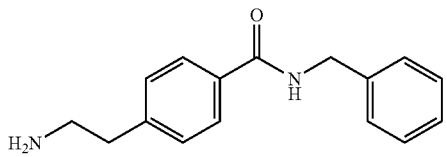

Methanolic hydrochloric acid was prepared by adding acetyl chloride (0.411 mL) to cooled (0° C.) methanol (5 mL) and stirring the solution for 1 h. It was then added to a cooled (0° C.) solution of [2-(4-benzylcarbamoylphenyl)ethyl]carbamic acid tert-butyl ester from step ii) (0.41 g) in methanol (5 mL) and the reaction mixture stirred for 1.5 h before concentration in vacuo to afford a pale yellow solid. The material was used directly in the next step.

iv) Benzyl {2-[[N-(2-{4-[(benzylamino)carbonyl]phenyl}ethyl)-β-alanyl](cycloheptyl)amino]ethyl}[2-(4-hydroxy-2-oxo-2,3-dihydro-1,3-benzothiazol-7-yl)ethyl]carbamate The product from step iv) (0.106 g) was dissolved in dichloromethane (1.5 mL) and cooled to 0° C. Hydrobromic acid in acetic acid (33%, 0.6 mL) was added dropwise. The reaction mixture was stirred for 2 h then concentrated and azeotroped with toluene (×3) and methanol (×3). The crude

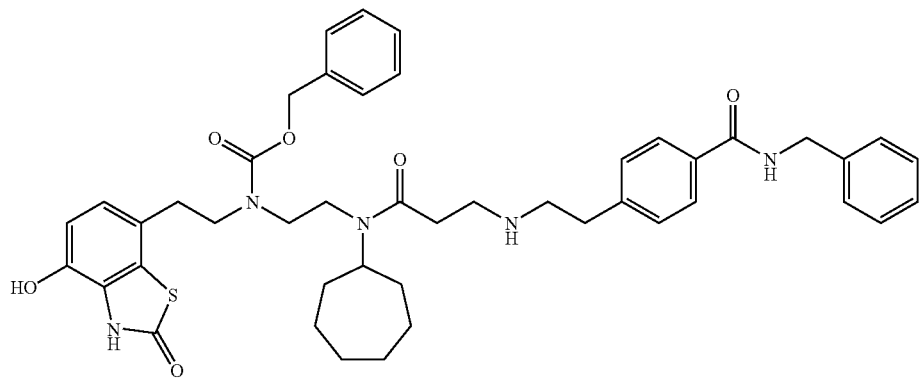

Triethylamine (0.9 mL) and ethanol (4 mL) were added to crude 4-(2-aminoethyl)-N-benzylbenzamide hydrochloride (0.336 g) then the volatiles were evaporated. The resulting solid and the acrylamide from Example 23 step ii) (0.15 g) were suspended in ethanol (4 mL) and triethylamine (0.156 mL) added. The reaction mixture was heated at 55° C. for 32 h then cooled and the volatiles evaporated. The crude mixture was purified firstly by an SCX cartridge and secondly by flash chromatography (Isolute, 1:3:16 to 1:7:12 7M $NH_3$ in methanol:ethanol:ethyl acetate) to afford the product as a yellow oil (42 mg).

MS: APCI (+ve): 792 [M+H]$^+$ v) N-Benzyl-4-[2-({3-[cycloheptyl(2-{[2-(4-hydroxy-2-oxo-2,3-dihydro-1,3-benzothiazol-7-yl)ethyl]amino}ethyl)amino]-3-oxopropyl}amino)ethyl]benzamide material was purified by reverse phase HPLC (75-5% of 0.2% aqueous TFA in acetonitrile) to afford the product as a white solid (0.027 g).

$^1$H NMR 90° C. $\delta_{(DMSO)}$ 8.70 (1H, t), 7.86 (2H, d), 7.37-7.20 (7H, m), 6.86 (1H, d), 6.75 (1H, d), 4.48 (2H, d), 3.72-3.67 (1H, m), 3.48 (2H, t), 3.29-2.82 (14H, m), 1.76-1.45 (12H, m)

MS: APCI (+ve): 658 [M+H]$^+$

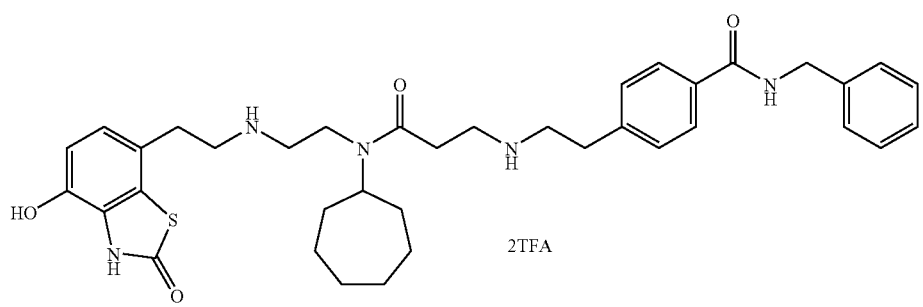

EXAMPLE 101

N-(2-{[2-(4-Hydroxy-2-oxo-2,3-dihydro-1,3-benzothiazol-7-yl)ethyl]amino}ethyl)-N-[(1R)-1-methylpentyl]-$N^3$-(2-phenylethyl)-β-alaninamide bis-trifluoroacetic acid salt

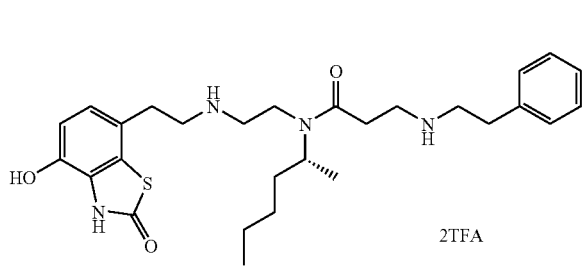

i) Benzyl [2-(4-hydroxy-2-oxo-2,3-dihydro-1,3-benzothiazol-7-yl)ethyl](2-{[(1R)-1-methylpentyl]amino}ethyl)carbamate

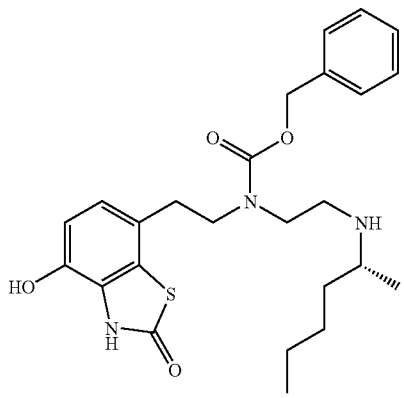

The aldehyde from Example 1 step ii) (0.5 g) and 1(R)-methylpentylamine (0.197 g) were dissolved in a mixture of THF (20 mL) and water (2 mL) and stirred for 30 min. Acetic acid (0.111 mL) was added, the mixture stirred for 15 min, then sodium cyanoborohydride (0.122 g) was added, and the mixture stirred for a further 20 h. The reaction was diluted with ethyl acetate (50 mL), washed with saturated sodium bicarbonate and brine, dried (Na2SO4), filtered and evaporated in vacuo. The residue was purified by flash column chromatography eluting with 10% (1M NH₃:methanol)/dichloromethane to give the sub-title compound (0.25 g), as a colourless gum.

¹H NMR δ$_{(DMSO)}$ 7.34 (5H, m), 6.73 (2H, m), 5.06 (2H, m), 3.43 (2H, t), 3.32 (2H, m), 3.09-2.77 (3H, m), 2.70 (2H, m), 2.43 (2H, m), 1.61-0.99 (7H, m), 0.87 (3H, m)

MS: APCI (+ve): 472 [M+H]⁺ ii) N-(2-{[2-(4-Hydroxy-2-oxo-2,3-dihydro-1,3-benzothiazol-7-yl)ethyl]amino}ethyl)-N-[(1R)-1-methylpentyl]-$N^3$-(2-phenylethyl)-β-alaninamide bis-trifluoroacetic acid salt

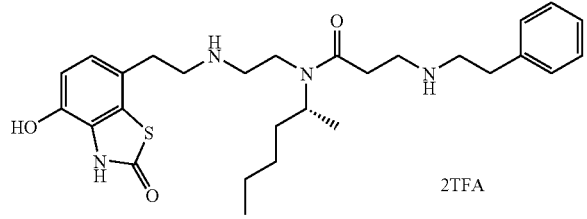

The amine from step i) (0.12 g) was dissolved in dichloromethane (5 mL), triethylamine (0.076 mL) added, followed by the acid chloride from Example 2 step v) (0.135 g) and stirred for 20 h. 1M NH₃/methanol (2 mL) was added and the mixture stirred for 30 min, then quenched with water, extracted with ethyl acetate, washed with brine, dried (Na2SO4), filtered and evaporated in vacuo. The residue was dissolved in acetic acid (1 mL), hydrobromic acid in acetic acid (33%, 1 mL) added and the mixture stirred for 1 h. Toluene was added, and the mixture evaporated in vacuo, redissolved in acetonitrile, toluene added and evaporated in vacuo once again. The residue was purified by reverse phase HPLC eluting with aqueous TFA/acetonitrile to give the title compound (0.07 g) as a white solid.

¹H NMR δ$_{(DMSO)}$ 10.14 (1H, s), 8.74-8.46 (4H, m), 7.34 (2H, m), 7.27 (3H, m), 6.86 (1H, m), 6.75 (1H, m), 3.80 (1H, m), 3.49 (2H, m), 3.36 (6H, m), 3.02 (2H, m), 2.93 (2H, m), 2.79 (4H, m), 1.47 (2H, m), 1.35-1.17 (4H, m), 1.15 (3H, d), 0.88 (3H, t)

MS: APCI (+ve): 513 [M+H]⁺

EXAMPLE 102

N-(2-{[2-(4-Hydroxy-2-oxo-2,3-dihydro-1,3-benzothiazol-7-yl)ethyl]amino}ethyl)-N-[(1S)-1-methylpentyl]-$N^3$-(2-phenylethyl)-β-alaninamide bis-trifluoroacetic acid salt

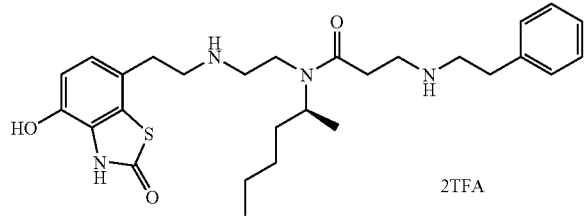

The title compound was prepared according to the procedure of Example 98, but using 1(S)-methylpentylamine in step i), to give the product as a white solid.

¹H NMR δ$_{(DMSO)}$ 10.17 (1H, s), 7.34 (2H, m), 7.27 (3H, m), 6.87 (1H, m), 6.76 (1H, m), 3.80 (1H, m), 3.49 (2H, m), 3.18 (6H, m), 3.03 (2H, m), 2.94 (2H, m), 2.80 (4H, m), 1.46 (2H, m), 1.33-1.15 (4H, m), 1.15 (3H, d), 0.88 (3H, t)

MS: APCI (+ve): 513 [M+H]⁺

EXAMPLE 103

N-Cyclohexyl-N³-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide bis-trifluoroacetic acid salt

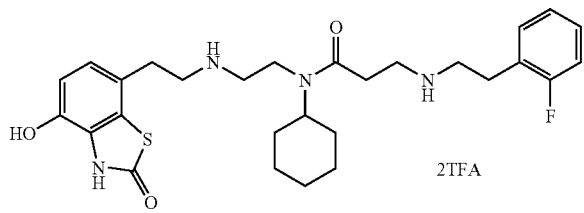

The title compound was prepared according to the procedure of Example 15, but using 2-fluorophenethylamine, to give a white solid.

¹H NMR δ$_{(DMSO)}$ 11.73 (1H, s)), 10.21-10.15 (1H, m), 8.98-8.62 (4H, m), 7.39-7.30 (2H, m), 7.24-7.16 (2H, m), 6.89-6.84 (1H, m), 6.78-6.74 (1H, m), 3.60-2.95 (13H, m), 2.87-2.77 (4H, m), 1.82-1.03 (10H, m)

MS: APCI (+ve): 529 [M+H]⁺

EXAMPLE 104

N-Cycloheptyl-N³-[2-(3-fluorophenyl)ethyl]-N-(2-{[2-(4-hydroxy-2-oxo-2,3-dihydro-1,3-benzothiazol-7-yl)ethyl]amino}propyl)-β-alaninamide bis-trifluoroacetic acid salt

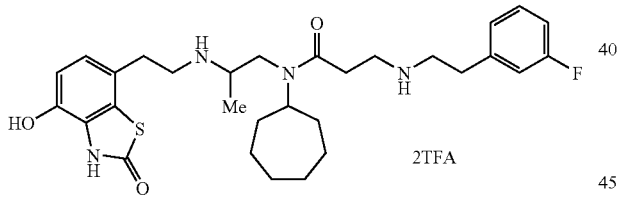

i) Benzyl [2-(4-hydroxy-2-oxo-2,3-dihydro-1,3-benzothiazol-7-yl)ethyl](1-methyl-2-oxoethyl)carbamate

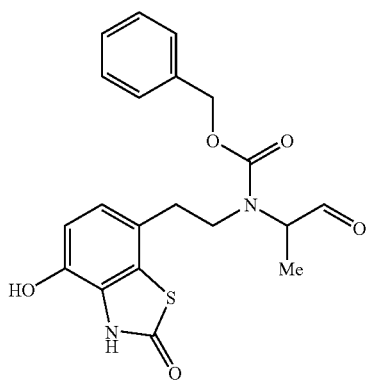

Sodium bicarbonate (1.16 g) was added to a solution of 7-(2-amino-ethyl)-4-hydroxy-3H-benzothiazol-2-one hydrobromide (4.0 g) in water (30 mL) and THF (60 mL), and the mixture was stirred for 15 min. Acetic acid (1.57 mL) was added, followed by 1,1-dimethoxyacetone (1.98 mL) and the mixture was stirred for 30 min. The reaction was then cooled in ice and sodium cyanoborohydride (1.73 g) was added in portions over 10 min. The reaction mixture was stirred for three days, then EtOAc (100 mL) and a solution of NaHCO3 (3.46 g) in water (50 mL) was added and the mixture stirred vigorously. Benzyl chloroformate (1.45 mL) was added and after 3 h a further portion of benzyl chloroformate (0.725 mL) was added. After 2 h the organic phase was separated, washed with water, then 0.1M HCl, water and brine. The resulting solution was evaporated and the residue was redissolved in acetone (75 mL), 2M HCl (50 mL) was added and the mixture was stirred for 2 days. The acetone was evaporated, and the aqueous was extracted into EtOAc. The organic phase was washed with brine, dried and evaporated affording an off-white foam (5 g). LC-MS showed the major component was a mixture of desired aldehyde and the corresponding hydrate (M+H 419/401). The crude aldehyde was used directly in the next step ii) Benzyl [2-(cycloheptylamino)-1-methylethyl][2-(4-hydroxy-2-oxo-2,3-dihydro-1,3-benzothiazol-7-yl)ethyl]carbamate

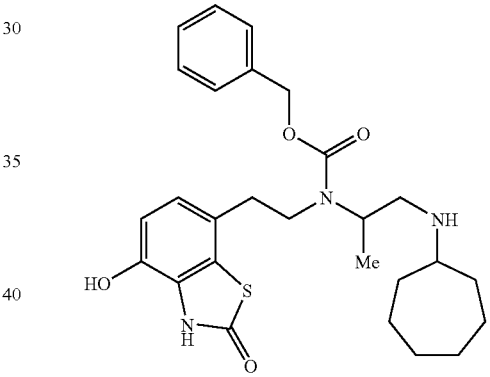

To a solution of benzyl [2-(4-hydroxy-2-oxo-2,3-dihydro-1,3-benzothiazol-7-yl)ethyl](1-methyl-2-oxoethyl)carbamate (2.5 g) in THF (60 mL) and water (10 mL) was added cycloheptylamine (1.59 mL). The reaction was left to stir for 30 min then acetic acid (0.714 mL) was added, and the reaction was stirred for another 30 min Sodium cyanoborohydride (0.784 g) was added and stirred RT overnight. Saturated NaHCO3 was added and the reaction was stirred for 15 min, then it was diluted with EtOAc (100 mL). The phases were separated, the aqueous was extracted with EtOAc, and the combined organics were washed with brine, dried and evaporated to afford an oil (5 g). The oil was taken up in MeOH and applied to a SCX cartridge (pre-wetted with MeOH), then washed with MeOH, and eluted with MeOH-10% 0.880 ammonia. Evaporation afforded a red foam which was dissolved in EtOAc, washed with 0.25M HCl, NaHCO3 solution, dried and evaporated affording the sub-title product as a yellow foam (460 mg)

¹H NMR δ$_{(DMSO)}$ 7.44-7.28 (m, 5H), 6.82-6.61 (m, 2H), 5.15-5.08 (m, 2H), 4.01-3.93 (m, 1H), 3.28-3.18 (m, 2H), 2.77-2.65 (m, 2H), 2.55-2.40 (m, 4H), 1.75-1.59 (m, 2H), 1.60-1.37 (m, 7H), 1.36-1.12 (m, 5H), 1.07-0.97 (m, 3H)

MS: APCI (+ve): 498 [M+H]⁺ iii) Benzyl {2-[acryloyl(cycloheptyl)amino]-1-methylethyl}[2-(4-hydroxy-2-oxo-2,3-dihydro-1,3-benzothiazol-7-yl)ethyl]carbamate

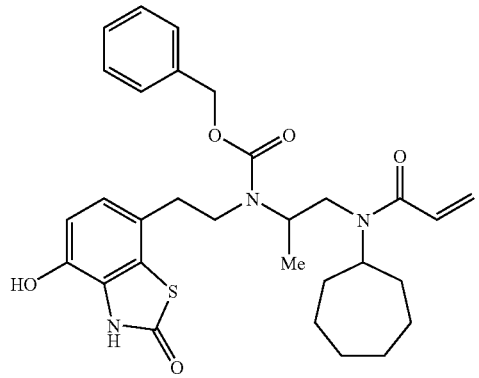

To a solution of Benzyl [2-(cycloheptylamino)-1-methylethyl][2-(4-hydroxy-2-oxo-2,3-dihydro-1,3-benzothiazol-7-yl)ethyl]carbamate (0.46 g) in CH2Cl2 (10 mL) was added triethylamine (0.773 mL) and trimethylsilyl chloride (0.586 mL) and the mixture was stirred for 1 h at room temperature. The reaction mixture was cooled in ice and acryloyl chloride (0.0976 mL) was added. The mixture was allowed to warm slowly to RT, diluted with CH2Cl2 and washed with 2M HCl and brine. Drying and evaporation afforded an orange foam (470 mg), which was used directly in the next step.

MS: APCI (+ve): 552 [M+H]$^+$ iv) N-Cycloheptyl-N$^3$-[2-(3-fluorophenyl)ethyl]-N-(2-{[2-(4-hydroxy-2-oxo-2,3-dihydro-1,3-benzothiazol-7-yl)ethyl]amino}propyl)-β-alaninamide bis-trifluoroacetic acid salt

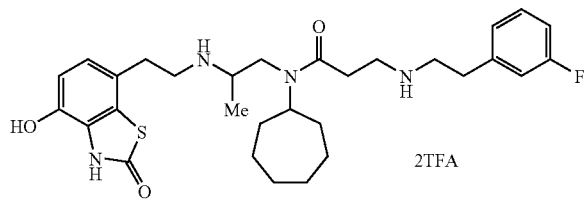

Benzyl {2-[acryloyl(cycloheptyl)amino]-1-methylethyl}[2-(4-hydroxy-2-oxo-2,3-dihydro-1,3-benzothiazol-7-yl)ethyl]carbamate (0.235 g) was dissolved in anhydrous ethanol (10 mL) and treated with the 3-fluorophenethylamine (0.166 mL) at 50° C. overnight. The reaction temperature was increased to 60° C., and the reaction was left for another 24 h. The solvent was partially evaporated to a smaller volume (~3 mL) and heating was continued at 60° C. for 3 h. The mixture was cooled and applied to an SCX cartridge, washed well with ethanol, and then eluted with MeOH/10% 0.880 ammonia. Evaporation afforded a brown oil (270 mg). The oil was dissolved in a mixture (2 mL) of 1:1 HBr—AcOH and AcOH under nitrogen in the dark at room temperature. After 1.5 h the reaction was diluted with toluene and evaporated. HPLC purification of the residual oil gave pure fractions which were evaporated, azeotroped with toluene, redissolved in CH2Cl2, evaporated and dried under high vacuum, to afford the title product as a clear foam (56 mg).

$^1$H NMR δ$_{(DMSO)}$ 11.73 (s, 1H), 10.16 (s, 1H), 8.78-8.43 (m, 4H), 7.42-7.35 (m, 1H), 7.28-7.21 (m, 1H), 7.21-7.04 (m, 2H), 6.88 (d, J=8.2 Hz, 1H), 6.76 (d, J=8.5 Hz, 1H), 1.20 (d, J=6.4 Hz, 3H), 3.74-2.75 (m, 16H), 1.86-1.38 (m, 12H)

MS: APCI (+ve): 557 [M+H]$^+$

EXAMPLE 105

N-Cyclohexyl-N-(2-{[2-(4-hydroxy-2-oxo-2,3-dihydro-1,3-benzothiazol-7-yl)ethyl]amino}propyl)-N$^3$-(2-phenylethyl)-β-alaninamide bis-trifluoroacetic acid salt

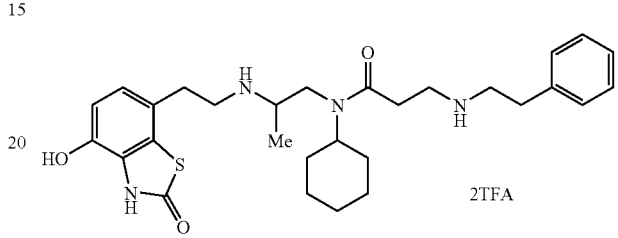

The title compound was prepared according to the procedure of Example 104, but using cyclohexylamine in step ii), and using phenethylamine in step iv) to afford the product as a colourless foam (0.034 g)

$^1$H NMR δ$_{(DMSO)}$ 11.73 (s, 1H), 10.16 (s, 1H), 8.73-8.43 (m, 4H), 7.38-7.30 (m, 2H), 7.30-7.22 (m, 2H), 7.20-7.11 (m, 1H), 6.88 (d, J=8.2 Hz, 1H), 6.76 (d, J=8.2 Hz, 1H), 4.17-3.66 (m, 3H), 3.61-3.49 (m, 2H), 3.46-3.30 (m, 2H), 3.29-3.03 (m, 6H), 2.99-2.71 (m, 6H), 1.86-1.68 (m, 3H), 1.67-1.55 (m, 2H), 1.52-1.40 (m, 2H), 1.22-1.06 (m, 3H)

MS: APCI (+ve): 525 [M+H]$^+$

Biological Assays

Adrenergic β2 Mediated cAMP Production

Cell Preparation

H292 cells were grown in 225 cm2 flasks incubator at 37° C., 5% CO$_2$ in RPMI medium containing, 10% (v/v) FBS (foetal bovine serum) and 2 mM L-glutamine.

Experimental Method

Adherent H292 cells were removed from tissue culture flasks by treatment with Accutase™ cell detachment solution for 15 minutes. Flasks were incubated for 15 minutes in a humidified incubator at 37° C., 5% CO$_2$. Detached cells were re-suspended in RPMI media (containing 10% (v/v) FBS and 2 mM L-glutamine) at 0.05×10$^6$ cells per mL. 5000 cells in 100 μL were added to each well of a tissue-culture-treated 96-well plate and the cells incubated overnight in a humidified incubator at 37° C., 5% CO$_2$. The culture media was removed and cells were washed twice with 100 μL assay buffer and replaced with 50 μL assay buffer (HBSS solution containing 10 mM HEPES pH 7.4 and 5 mM glucose). Cells were rested at room temperature for 20 minutes after which time 25 μL of rolipram (1.2 mM made up in assay buffer containing 2.4% (v/v) dimethylsulphoxide) was added. Cells were incubated with rolipram for 10 minutes after which time test compounds were added and the cells were incubated for 60 minutes at room temperature. The final rolipram concentration in the assay was 300 μM and final vehicle concentration was 1.6% (v/v) dimethylsulphoxide. The reaction was stopped by removing supernatants, washing once with 100 μL assay buffer and replacing with 50 μL lysis buffer. The cell monolayer was frozen at −80° C. for 30 minutes (or overnight).

AlphaScreen™ cAMP Detection

The concentration of cAMP (cyclic adenosine monophosphate) in the cell lysate was determined using AlphaScreen™ methodology. The frozen cell plate was thawed for 20 minutes on a plate shaker then 10 μL of the cell lysate was transferred to a 96-well white plate. 40 μL of mixed AlphaScreen™ detection beads pre-incubated with biotinylated cAMP, was added to each well and the plate incubated at room temperature for 10 hours in the dark. The AlphaScreen™ signal was measured using an EnVision spectrophotometer (Perkin-Elmer Inc.) with the recommended manufacturer's settings. cAMP concentrations were determined by reference to a calibration curve determined in the same experiment using standard cAMP concentrations. Concentration response curves for agonists were constructed and data was fitted to a four parameter logistic equation to determine both the $pEC_{50}$ and Intrinsic Activity. Intrinsic Activity was expressed as a fraction relative to the maximum activity determined for formoterol in each experiment. Results for compounds of the invention are to be found in Table 1.

Selectivity Assays

Adrenergic α1D

Membrane Preparation

Membranes were prepared from human embryonic kidney 293 (HEK293) cells expressing recombinant human $α1_D$ receptor. These were diluted in Assay Buffer (50 mM HEPES, 1 mM EDTA, 0.1% gelatin, pH 7.4) to provide a final concentration of membranes that gave a clear window between maximum and minimum specific binding.

Experimental Method

Assays were performed in U-bottomed 96-well polypropylene plates. 10 μL [$^3$H]-prazosin (0.3 nM final concentration) and 10 μL of test compound (10× final concentration) were added to each test well. For each assay plate 8 replicates were obtained for [$^3$H]-prazosin binding in the presence of 10 μL vehicle (10% (v/v) DMSO in Assay Buffer; defining maximum binding) or 10 μL BMY7378 (10 μM final concentration; defining non-specific binding (NSB)). Membranes were then added to achieve a final volume of 100 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-prazosin binding) were determined using serial dilutions typically in the range 0.1 nM to 10 μM. Data was fitted to a four parameter logistic equation to determine the compound potency, which was expressed as pIC50 (negative log molar concentration inducing 50% inhibition of [$^3$H]-prazosin binding). Results are shown in Table 1 below.

Adrenergic β1

Membrane Preparation

Membranes containing recombinant human adrenergic beta 1 receptors were obtained from Euroscreen. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 10 μL [$^{125}$I]-Iodocyanopindolol (0.036 nM final concentration) and 10 μL of test compound (10× final concentration) were added to each test well. For each assay plate 8 replicates were obtained for [$^{125}$I]-Iodocyanopindolol binding in the presence of 10 μL vehicle (10% (v/v) DMSO in Assay Buffer; defining maximum binding) or 10 μL Propranolol (10 μM final concentration; defining non-specific binding (NSB)). Membranes were then added to achieve a final volume of 100 μL. The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^{125}$I]-Iodocyanopindolol binding) were determined using serial dilutions typically in the range 0.1 nM to 10 μM. Data was fitted to a four parameter logistic equation to determine the compound potency, which was expressed as $pIC_{50}$ (negative log molar concentration inducing 50% inhibition of [$^{125}$I]-Iodocyanopindolol binding). Results are shown in Table 1 below.

Dopamine D2

Membrane Preparation

Membranes containing recombinant human Dopamine Subtype D2s receptors were obtained from Perkin Elmer. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 30 μL [$^3$H]-spiperone (0.16 nM final concentration) and 30 μL of test compound (10× final concentration) were added to each test well. For each assay plate 8 replicates were obtained for [$^3$H]-spiperone binding in the presence of 30 μL vehicle (10% (v/v) DMSO in Assay Buffer; defining maximum binding) or 30 μL Haloperidol (10 μM final concentration; defining non-specific binding (NSB)). Membranes were then added to achieve a final volume of 300 μL.

The plates were incubated for 2 hours at room temperature and then filtered onto PEI coated GF/B filter plates, pre-soaked for 1 hour in Assay Buffer, using a 96-well plate Tomtec cell harvester. Five washes with 250 μL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 μL) was added to each well. The plates were sealed (TopSeal A) and filter-bound radioactivity was measured with a scintillation counter (Top-Count, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-spiperone binding) were determined using serial dilutions typically in the range 0.1 nM to 10 μM. Data was fitted to a four parameter logistic equation to determine the compound potency, which was expressed as $pIC_{50}$ (negative log molar concentration inducing 50% inhibition of [$^3$H]-spiperone binding).

The results obtained for a representative selection of the compounds of the Examples are shown in Table 1 below.

Onset Assay

Dunkin-Hartley guinea-pigs (between 200 g and 300 g on delivery) were supplied by a designated breeding establishment. The guinea-pigs were killed by cervical dislocation and the trachea removed. The adherent connective tissue was removed and each trachea cut into four rings. The tissue rings were then attached to an isometric transducer. The tissues were washed and a force of 1 g was applied to each ring. In all experiments a paired curve design was used. A priming dose of 1 μM methacholine was applied to the tissues. The tissues were then washed (three times, one minute between washes), the resting tension of 1 g was reapplied and the tissues were allowed to rest for 1 hour to equilibrate. Tissues were then contracted with 1 μM methacholine and once a steady response was obtained a cumulative concentration response curve to isoprenaline ($10^{-9}$ M-$10^{-5}$ M) was constructed. The tissues were then washed (three times, one minute between washes) and left to rest for an hour. At the end of the resting period the tissues were contracted with 1 μM methacholine and a $p[A]_{50}$ concentration of test compound added. Once the tissue had reached maximum relaxation, a 30×$p[A]_{50}$ concentration of test compound was added. Once the tissue response had reached a plateau, 10 μM sotalol was added to the bath to confirm that the relaxation was $\beta_2$ mediated Data were collected using the ADInstruments chart4forwindows software, which measured the maximum tension generated at each concentration of agonist.

For each concentration of the isoprenaline cumulative concentration curve, the response was calculated as % relaxation of the methacholine-induced contraction. A curve was plotted of $\log_{10}$ [agonist] (M) versus percentage inhibition of the methacholine-induced contraction. These data were then fitted to a non-linear regression curve fit. For each experiment, E/[A] curve data were fitted using a 4-parameter logistic function of the form:

$$E = \beta + \frac{(\beta - \alpha) \cdot [A]^m}{[A]^m + [A]_{50}^m}$$

E and [A] are the pharmacological effect (% relaxation) and concentration of the agonist respectively; α, β, $[A]_{50}$ and m are the asymptote, baseline, location and slope parameters, respectively. The $p[A]_{50}$ and IA of each isoprenaline curve was determined from this fit, to determine if the tissue was viable for generating an onset time for the test compounds.

For each $p[A]_{50}$ concentration of the test compound, the response was calculated as % relaxation of the methacholine-induced contraction. The results were plotted % relaxation against time and the time taken to reach a 90% relaxation value was calculated and recorded.

The addition of a 30×$p[A]_{50}$ concentration enabled determination of the maximum compound effect within the individual tissue. Hence, the % of the maximum compound effect at the $p[A]_{50}$ concentration was calculated and recorded.

Pharmacokinetics in the Rat

A dose solution of the test compound was prepared using a suitable dose vehicle. The concentration of the compound in the dose solution was assayed by diluting an aliquot to a nominal concentration of 50 μg·ml$^{-1}$ and calibrating against duplicate injections of a standard solution and a QC standard at this concentration. Compounds were administered intravenously as a bolus into a caudal vein to groups of three 250-350 g rats (approximately 1 ml·kg$^{-1}$). For the oral dose, a separate group of 2 or 3 animals were dosed by oral gavage (3 ml·kg$^{-1}$). Delivered doses were estimated by weight loss. Food was not usually withdrawn from animals prior to dosing, although this effect was investigated if necessary.

Blood samples (0.25 ml) were taken into 1 ml syringes from the caudal vein, transferred to EDTA tubes and plasma was prepared by centrifugation (5 min at 13000 rpm) soon after sample collection, before storage at −20° C. Typical sampling times were 2, 4, 8, 15, 30, 60, 120, 180, 240, 300 (min) or until the terminal t1/2 was accurately described.

The concentration of the analyte(s) were determined in plasma by quantitative mass spectrometry. Standard and quality control stock solutions were prepared at a concentration 1 mg/ml in methanol. A range of standard and QC stocks produced by serial dilution were added to control rat plasma (50 μl). The range of concentrations covered the range of levels of analyte present in the rat samples. Standards, QCs and samples underwent liquid extraction using 50 μl of organic solvent and 100 μl of organic solvent containing an internal standard, chosen to closely resemble the analyte. The samples were then mixed by repeated inversion, stored at −20° C. for at least 1 h, and centrifuged at 3500 rpm in a centrifuge for 20 minutes. Aliquots (120 μl) of each sample were transferred for analysis using LC-MSMS. Standard and quality control samples covering the range of concentrations found in the test samples were within 25% of the nominal concentration.

Pharmacokinetic data analysis was achieved using WinNonlin. A standard non-compartmental analysis was used to estimate the parameters such as Tmax, Cmax, Lambda_z, t1/2_Lambda_z, AUCall, AUCINF(observed), Cl(observed), Vss(observed).

TABLE 1

| Example No. | β2 pEC50 | β2 Int Act | α1 bind pIC50 | β1 bind p IC50 | D2 bind pIC50 |
|---|---|---|---|---|---|
| 1 | 7.7 | 0.78 | 6.6 | 5.0 | 6.4 |
| 2 | 8.5 | 1.04 | 6.9 | 5.3 | 6.6 |

TABLE 1-continued
| Example No. | β2 pEC50 | β2 Int Act | α1 bind pIC50 | β1 bind p IC50 | D2 bind pIC50 |
|---|---|---|---|---|---|
| 3 | 7.4 | 0.34 | 6.6 | 5.0 | 6.1 |
| 4 | 9.0 | 0.79 | 6.7 | 5.6 | 5.7 |
| 5 | 8.6 | 0.83 | 7.0 | 5.3 | 6.4 |
| 6 | 8.7 | 0.89 | 6.9 | 6.1 | 6.7 |
| 7 | 8.4 | 0.68 | 6.6 | 5.5 | 6.5 |
| 8 | 8.0 | 0.73 | 6.3 | 5.3 | 6.4 |
| 9 | 8.1 | 0.65 | 6.0 | 5.3 | 6.6 |
| 10 | 8.3 | 0.69 | 6.6 | 5.0 | 6.1 |
| 11 | 7.8 | 0.84 | 6.3 | 5.1 | 6.3 |
| 12 | 8.6 | 0.87 | 6.7 | 5.5 | 7.3 |
| 13 | 8.3 | 0.71 | 6.5 | 5.5 | 6.9 |
| 14 | 8.4 | 0.84 | 6.8 | 5.1 | 6.3 |
| 15 | 8.6 | 0.85 | 6.7 | 5.2 | 6.4 |
| 16 | 8.4 | 0.91 | 7.0 | 5.1 | 6.2 |
| 17 | 8.8 | 0.90 | 7.3 | 5.5 | 6.8 |
| 18 | 8.4 | 0.89 | 6.7 | 5.0 | 6.1 |
| 19 | 7.4 | 0.70 | 6.4 | 5.0 | 6.0 |
| 20 | 8.0 | 0.97 | 6.6 | 5.0 | 6.1 |
| 21 | 7.5 | 0.85 | 6.6 | 5.0 | 5.4 |
| 22 | 8.6 | 0.96 | 6.6 | 5.4 | 5.1 |
| 23 | 9.0 | 0.85 | 7.2 | 5.4 | 6.6 |
| 24 | 8.1 | 0.77 | 6.2 | 5.7 | 6.1 |
| 25 | 8.1 | 1.05 | 6.6 | 5.3 | 5.6 |
| 26 | 8.1 | 0.83 | 6.3 | 5.3 | 6.0 |
| 27 | 8.0 | 0.95 | 6.6 | 5.3 | 5.5 |
| 28 | 8.0 | 0.87 | 6.5 | 5.2 | 6.4 |
| 29 | 8.4 | 0.97 | 7.0 | 5.5 | 6.6 |
| 30 | 8.3 | 0.96 | 6.7 | 5.5 | 6.5 |
| 31 | 8.0 | 0.92 | 6.7 | 5.2 | 6.6 |
| 32 | 7.1 | 0.67 | 6.4 | 5.1 | 6.4 |
| 33 | 7.8 | 0.78 | 7.0 | 5.0 | 6.2 |
| 34 | 8.7 | 0.75 | 6.7 | 5.1 | 6.4 |
| 35 | 8.4 | 0.91 | 6.8 | 5.4 | 6.5 |
| 36 | 8.6 | 0.84 | 6.8 | 5.5 | 6.7 |
| 37 | 9.0 | 0.91 | 6.7 | 5.4 | 6.4 |
| 38 | 7.2 | 0.42 | 6.1 | 5.3 | 6.1 |
| 39 | 6.6 | 0.58 | 6.2 | 5.0 | 5.9 |
| 40 | 7.2 | 0.64 | 6.1 | 5.0 | 6.1 |
| 41 | 7.5 | 0.99 | 7.9 | 5.8 | 6.7 |
| 42 | 7.8 | 0.82 | 7.2 | 5.9 | 7.0 |
| 43 | 8.0 | 0.67 | 6.8 | 5.3 | 6.7 |
| 44 | 8.2 | 0.73 | 6.5 | 5.3 | 6.9 |
| 45 | 7.6 | 0.55 | 6.7 | 5.9 | 6.6 |
| 46 | 8.5 | 0.78 | 6.8 | 5.8 | 7.4 |
| 47 | 8.5 | 0.73 | 6.3 | 5.9 | 6.8 |
| 48 | 8.0 | 0.55 | 6.2 | 5.6 | 7.0 |
| 49 | 8.1 | 0.59 | 6.2 | 5.8 | |
| 50 | 8.9 | 0.91 | 7.1 | 6.1 | 7.5 |
| 51 | 8.3 | 0.59 | 6.5 | 5.6 | 7.6 |
| 52 | 8.5 | 0.92 | 7.0 | 5.8 | 7.4 |
| 53 | 8.0 | 0.74 | 6.9 | 5.4 | 7.1 |
| 54 | 8.0 | 0.69 | 6.5 | 5.6 | 7.3 |
| 55 | 8.0 | 0.81 | 7.3 | 5.6 | 7.7 |
| 56 | 8.3 | 0.86 | 6.6 | 5.5 | 7.5 |
| 57 | 7.7 | 0.72 | 7.3 | 5.6 | 7.5 |
| 58 | 8.4 | 0.84 | 6.6 | 5.3 | 6.8 |
| 59 | 8.3 | 0.85 | 7.0 | 6.1 | 6.4 |
| 60 | 7.7 | 0.76 | 6.5 | 5.7 | 6.1 |
| 61 | 8.0 | 0.79 | 6.5 | 5.6 | 6.1 |
| 62 | 8.2 | 0.87 | 7.2 | 6.4 | 6.4 |
| 63 | 7.1 | 0.93 | 6.8 | 5.6 | 6.7 |
| 64 | 6.5 | 0.70 | 7.1 | 5.2 | 6.7 |
| 65 | 7.9 | 0.59 | 7.0 | 6.0 | 6.4 |
| 66 | 7.9 | 0.59 | 6.6 | 5.8 | 6.2 |
| 67 | 7.7 | 0.70 | 6.7 | 6.0 | 6.8 |
| 68 | 8.0 | 0.68 | 6.7 | 5.4 | 7.3 |
| 69 | 8.7 | 0.82 | 6.8 | 5.2 | 7.0 |
| 70 | 8.3 | 0.84 | 6.9 | 5.0 | 6.7 |
| 71 | 9.4 | 0.97 | 6.7 | 5.4 | 7.0 |
| 72 | 8.4 | 0.89 | 6.4 | 5.5 | 6.9 |
| 73 | 8.3 | 0.85 | 6.4 | 5.1 | 6.7 |
| 74 | 7.9 | 0.79 | 6.6 | 5.5 | 6.3 |
| 75 | 8.0 | 0.91 | 6.6 | 6.2 | 6.4 |
| 76 | 8.2 | 0.68 | 6.8 | 5.4 | 6.7 |
| 77 | 6.8 | 0.54 | 6.6 | 5.2 | 6.8 |
| 78 | 8.5 | 0.91 | 6.6 | 5.4 | 6.5 |
| 79 | 8.6 | 0.84 | 7.2 | 5.5 | 6.8 |
| 80 | 6.9 | 0.86 | 5.9 | 5.0 | 6.4 |
| 81 | 8.6 | 0.89 | 6.7 | 5.2 | 6.5 |
| 82 | 7.1 | 0.86 | 6.6 | 5.6 | 7.3 |
| 83 | 8.4 | 0.71 | 7.2 | 5.3 | 7.2 |
| 84 | 7.7 | 0.89 | 7.0 | 6.0 | 7.1 |
| 85 | 8.2 | 0.65 | 7.3 | 5.6 | 7.1 |
| 86 | 7.4 | 0.43 | 6.6 | 5.6 | 6.7 |
| 87 | 8.5 | 0.72 | 6.6 | 6.1 | 7.4 |
| 88 | 7.6 | 0.37 | 6.6 | 5.2 | 7.1 |
| 89 | 8.9 | 0.9 | 7.3 | 5.5 | 7.1 |
| 90 | 8.4 | 0.71 | 7.2 | 6.7 | 7.1 |
| 91 | 8.4 | 0.75 | 6.9 | 5.4 | 7.4 |
| 92 | 8.5 | 0.91 | 6.6 | 5.4 | 6.5 |
| 93 | 8.6 | 0.89 | 6.7 | 5.2 | 6.5 |
| 94 | 8.1 | 0.77 | 6.2 | 5.7 | 6.1 |
| 95 | 8.6 | 0.84 | 6.8 | 5.5 | 6.7 |
| 96 | 8.6 | 0.85 | 6.7 | 5.2 | 6.4 |
| 98 | 8.8 | 0.8 | 7.2 | 5.7 | 6.8 |
| 100 | 8.2 | 0.81 | 6.6 | 5.9 | 7.5 |
| 101 | 8.6 | 0.98 | 7.3 | 5.4 | 7.5 |
| 102 | 7.1 | 0.23 | 7 | 5.9 | 7.1 |
| 103 | 8.8 | 0.67 | 7.3 | 6.2 | 7.2 |
| 104 | 8.3 | 0.81 | 7 | 6.1 | 7.2 |
| 105 | 8.2 | 0.86 | 7.1 | 5.8 | 6.5 |
Route A
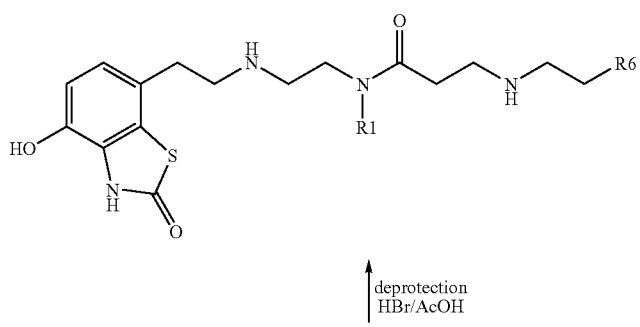
↑ deprotection
HBr/AcOH 123 124
-continued
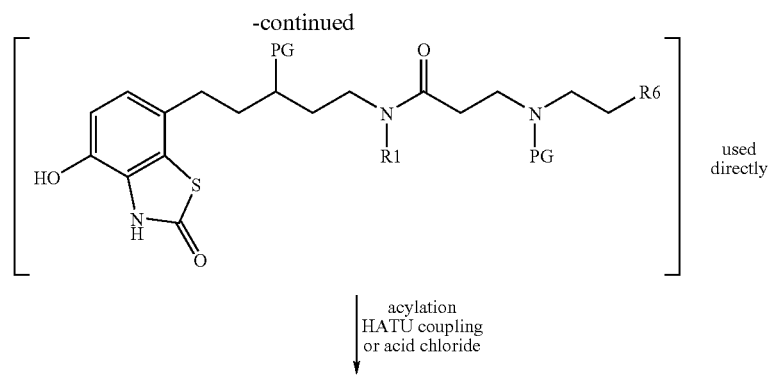
used directly
↓ acylation
HATU coupling
or acid chloride
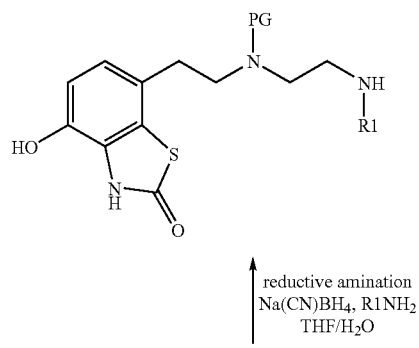
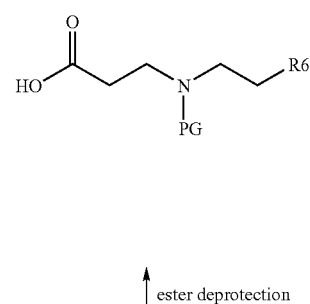
↑ reductive amination
Na(CN)BH$_4$, R1NH$_2$
THF/H$_2$O
↑ ester deprotection
TFA/DCM R = tBu
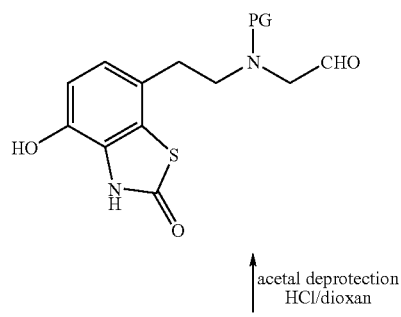
used directly
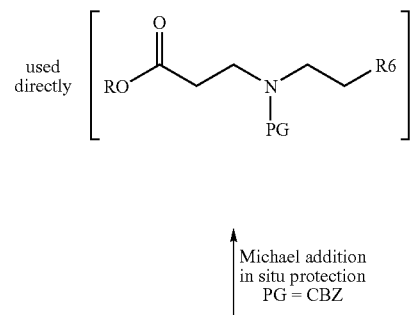
↑ acetal deprotection
HCl/dioxan
↑ Michael addition
in situ protection
PG = CBZ

125 126
-continued
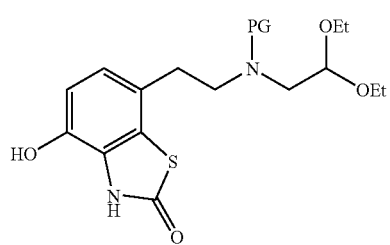
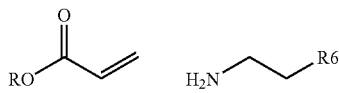
reductive amination
Na(CN)BH₄
in situ protection
PG = CBZ
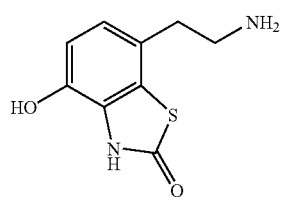
Route B
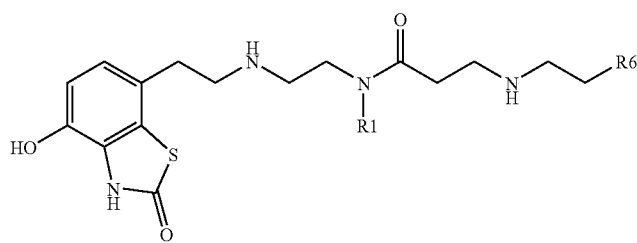
deprotection
HBr/AcOH
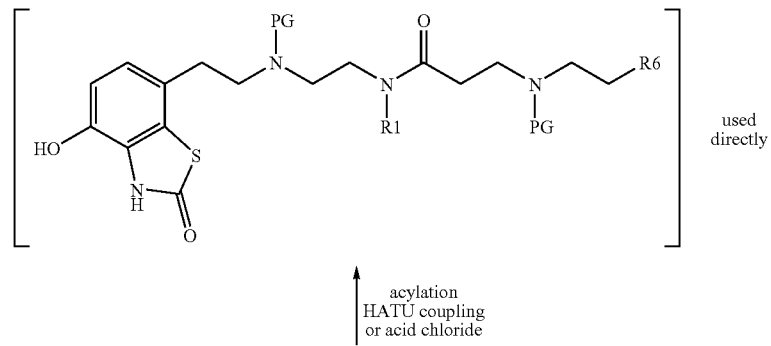
used directly
acylation
HATU coupling
or acid chloride 127
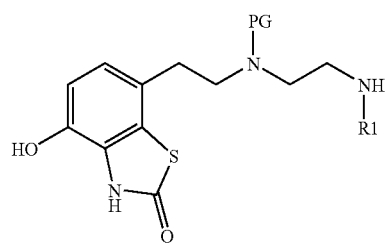
↑ reductive amination
Na(CN)BH₄,
THF/H₂O
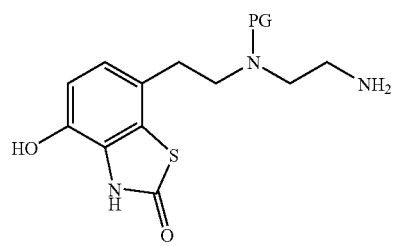
↑ Boc deprotection
HCl/dioxan
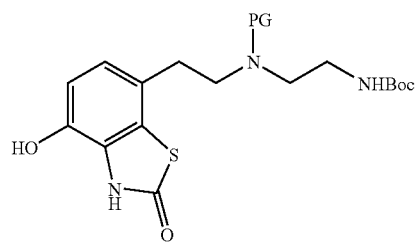
↑ reductive amination
Na(CN)BH₄ THF/H20
in situ protection
PG = CBZ
128
-continued
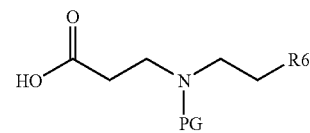
↑ ester deprotection
HCl/dioxan, R = tBu
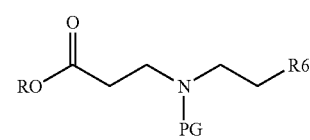
↑ Michael addition
in situ protection
PG = CBZ
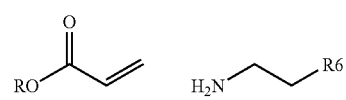

Route C
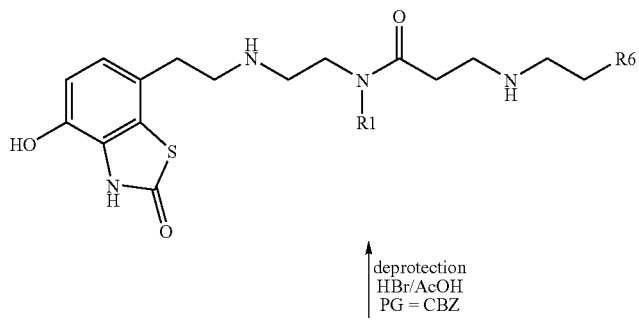
↑ deprotection
HBr/AcOH
PG = CBZ
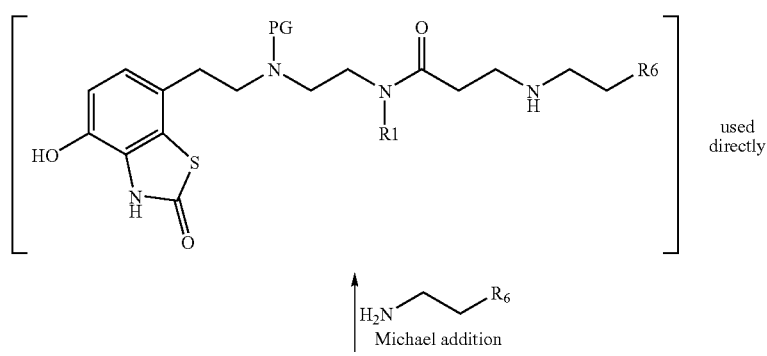
used directly
↑ Michael addition
$H_2N$―CH$_2$CH$_2$―R6
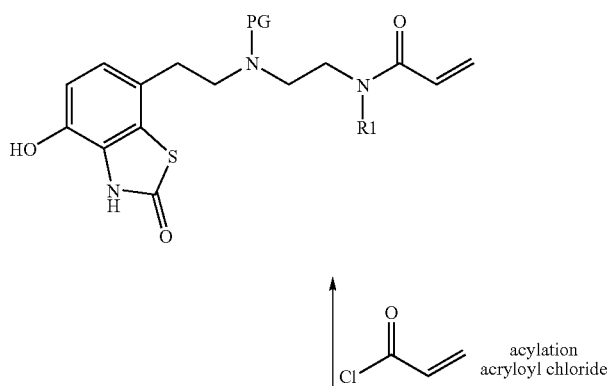
↑ acylation
acryloyl chloride
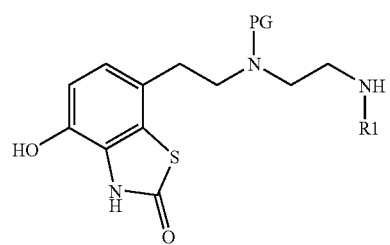

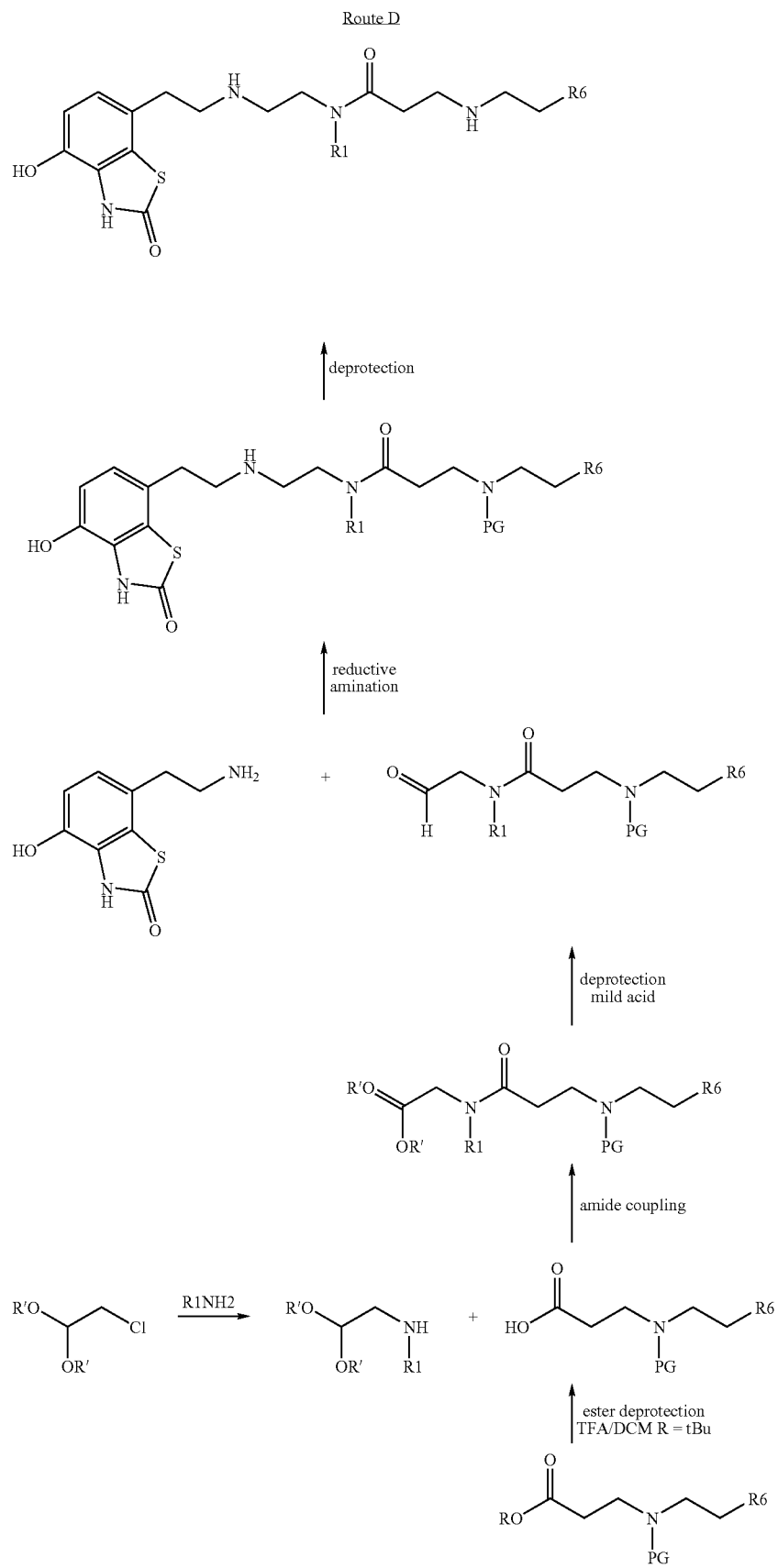

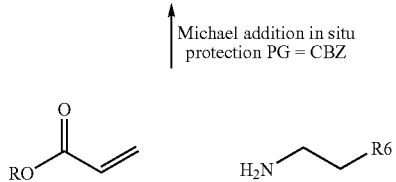

The invention claimed is:

1. A compound N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide, or a pharmaceutically acceptable salt thereof.

2. A compound as claimed in claim 1 in the form of a pharmaceutically acceptable salt, wherein the salt is an acid addition salt which is selected from the group consisting of hydrochloride, hydrobromide, sulphate, phosphate, acetate, fumarate, maleate, tartrate, lactate, citrate, pyruvate, succinate, oxalate, methanesulphonate, and p-toluenesulphonate.

3. A compound as claimed in claim 1 which is the compound N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide.

* * * * *

UNITED STATES PATENT AND TRADEMARK OFFICE
CERTIFICATE OF CORRECTION

PATENT NO. : 7,700,782 B2 Page 1 of 1
APPLICATION NO. : 11/959679
DATED : April 20, 2010
INVENTOR(S) : Stephen Connolly, Alexander Humphries and Premji Meghani It is certified that error appears in the above-identified patent and that said Letters Patent is hereby corrected as shown below:

Title Page, item (74), column 2 (Attorney, Agent, or Firm), line 1, "Sigh" should read -- Fish --.

Signed and Sealed this

Twenty-second Day of June, 2010

David J. Kappos
*Director of the United States Patent and Trademark Office*